United States Patent
Nagasaka et al.

(10) Patent No.: US 10,870,038 B2
(45) Date of Patent: Dec. 22, 2020

(54) ACTIVITY RECORDING DATA PROCESSING APPARATUS

(71) Applicant: CASIO COMPUTER CO., LTD., Tokyo (JP)

(72) Inventors: Tomoaki Nagasaka, Koganei (JP); Masashi Ueda, Tachikawa (JP)

(73) Assignee: CASIO COMPUTER CO., LTD., Tokyo (JP)

( * ) Notice: Subject to any disclaimer, the term of this patent is extended or adjusted under 35 U.S.C. 154(b) by 256 days.

(21) Appl. No.: 16/040,445

(22) Filed: Jul. 19, 2018

(65) Prior Publication Data

US 2019/0038937 A1 Feb. 7, 2019

(30) Foreign Application Priority Data

Aug. 3, 2017 (JP) ................................. 2017-150670

(51) Int. Cl.
*A63B 24/00* (2006.01)
*G01C 22/00* (2006.01)
(Continued)

(52) U.S. Cl.
CPC ........ *A63B 24/0062* (2013.01); *A61B 5/0022* (2013.01); *A61B 5/6804* (2013.01); *A63B 24/0003* (2013.01); *A63B 24/0021* (2013.01); *G01C 22/002* (2013.01); *G06Q 10/0639* (2013.01); *G16H 10/60* (2018.01); *A61B 5/4866* (2013.01); *A63B 2024/0025* (2013.01); (Continued)

(58) Field of Classification Search
CPC ............ A63B 24/0062; A63B 24/0003; A63B 24/0021; A63B 2220/12; A63B 2220/30; A63B 2220/40; A63B 2220/72; A63B 2220/73; A63B 2230/06; A63B 2230/75; G01C 22/002; G01S 19/19; G01S 19/48; G06Q 10/0639
See application file for complete search history.

(56) References Cited

U.S. PATENT DOCUMENTS 7,350,787 B2 4/2008 Voss
7,647,196 B2 1/2010 Kahn et al.
(Continued)

FOREIGN PATENT DOCUMENTS

| CN | 105536205 A | 5/2016 |
|---|---|---|
| JP | H03154820 A | 7/1991 |

(Continued)

OTHER PUBLICATIONS

Japanese Office Action dated Oct. 1, 2019 (and English translation thereof) issued in Japanese Patent Application No. 2017-150670.
(Continued)

*Primary Examiner* — Manuel L Barbee
(74) *Attorney, Agent, or Firm* — Holtz, Holtz & Volek PC

(57) ABSTRACT

An activity recording data processing apparatus is provided. This apparatus includes an operation unit configured to acquire data obtained for a series of activity and action estimation information on the series of activity, the action estimation information being associated with the data; extract partial data of the data based on the action estimation information; and perform clustering of the extracted partial data.

13 Claims, 32 Drawing Sheets

(51) Int. Cl.
*G06Q 10/06* (2012.01)
*G16H 10/60* (2018.01)
*A61B 5/00* (2006.01)
*G01S 19/19* (2010.01)

(52) U.S. Cl.
CPC ....... *A63B 2220/12* (2013.01); *A63B 2220/30* (2013.01); *A63B 2220/40* (2013.01); *A63B 2220/62* (2013.01); *A63B 2220/72* (2013.01); *A63B 2220/73* (2013.01); *A63B 2225/50* (2013.01); *A63B 2230/06* (2013.01); *A63B 2230/75* (2013.01); *G01S 19/19* (2013.01)

(56) References Cited

U.S. PATENT DOCUMENTS

| | | | |
|---|---|---|---|
| 9,936,912 | B2 | 4/2018 | Roovers et al. |
| 2002/0180166 | A1 | 12/2002 | Voss |
| 2005/0093739 | A1 | 5/2005 | Dilellio |
| 2008/0272560 | A1 | 11/2008 | Voss |
| 2009/0043531 | A1 | 2/2009 | Kahn et al. |
| 2012/0116550 | A1* | 5/2012 | Hoffman ............... G06F 1/1626 700/91 |
| 2012/0317064 | A1 | 12/2012 | Hagiwara et al. |
| 2013/0063647 | A1 | 3/2013 | Nishikawa |
| 2013/0196688 | A1 | 8/2013 | Lu et al. |
| 2013/0197857 | A1 | 8/2013 | Lu et al. |
| 2014/0031703 | A1 | 1/2014 | Rayner et al. |
| 2014/0195103 | A1 | 7/2014 | Nassef |
| 2014/0228988 | A1 | 8/2014 | Hoffman et al. |
| 2015/0130153 | A1 | 5/2015 | Chen et al. |
| 2015/0251053 | A1 | 9/2015 | Hoffman et al. |
| 2015/0258380 | A1 | 9/2015 | Hoffman et al. |
| 2015/0345952 | A1 | 12/2015 | Chang et al. |
| 2015/0374307 | A1 | 12/2015 | Nagasaka |
| 2016/0058372 | A1 | 3/2016 | Raghuram et al. |
| 2016/0067547 | A1* | 3/2016 | Anthony ............. G01P 15/0891 702/141 |
| 2016/0107064 | A1 | 4/2016 | Hoffman et al. |
| 2017/0007166 | A1 | 1/2017 | Roovers et al. |
| 2017/0036064 | A1 | 2/2017 | Hoffman et al. |
| 2017/0050080 | A1 | 2/2017 | Mizuochi |
| 2017/0056727 | A1 | 3/2017 | Hoffman et al. |
| 2017/0074666 | A1 | 3/2017 | Kobayashi et al. |
| 2017/0176187 | A1 | 6/2017 | Ishihama |
| 2017/0327184 | A1 | 11/2017 | Contello et al. |
| 2017/0333753 | A1 | 11/2017 | Hoffman et al. |
| 2018/0093132 | A1 | 4/2018 | Hoffman et al. |
| 2018/0111022 | A1 | 4/2018 | Hoffman et al. |
| 2018/0180442 | A1 | 6/2018 | Uchida |

FOREIGN PATENT DOCUMENTS

| | | |
|---|---|---|
| JP | H10318777 A | 12/1998 |
| JP | 2004282406 A | 10/2004 |
| JP | 2006084312 A | 3/2006 |
| JP | 2007160076 A | 6/2007 |
| JP | 2008086479 A | 4/2008 |
| JP | 2009134590 A | 6/2009 |
| JP | 2009288022 A | 12/2009 |
| JP | 2013003643 A | 1/2013 |
| JP | 2013006497 A | 1/2013 |
| JP | 2013095306 A | 5/2013 |
| JP | 2013543156 A | 11/2013 |
| JP | 2015093671 A | 5/2015 |
| JP | 2015184159 A | 10/2015 |
| JP | 2016006611 A | 1/2016 |
| JP | 2016010562 A | 1/2016 |
| JP | 2016088386 A | 5/2016 |
| JP | 2016119624 A | 6/2016 |
| JP | 2016158780 A | 9/2016 |
| JP | 2016179718 A | 10/2016 |
| JP | 2017116443 A | 6/2017 |
| WO | 2009021147 A1 | 2/2009 |
| WO | 2012021507 A2 | 2/2012 |
| WO | 2015146047 A1 | 10/2015 |

OTHER PUBLICATIONS

Office Action (Non-Final Rejection) dated Apr. 1, 2020 issued in related U.S. Appl. No. 16/040,458.
Related U.S. Appl. No. 16/040,458, filed Jul. 19, 2018, First Named Inventor: Tomoaki Nagasaka, Title: Track Estimation Device.
Related U.S. Appl. No. 16/040,472, filed Jul. 19, 2018, First Named Inventor: Tomoaki Nagasaka, Title: Activity State Analyzer to Analyze Activity State During Cycling.
Chinese Office Action (and English language translation thereof) dated Mar. 9, 2020 issued in Chinese Application No. 201810875511.6.
Extended European Search Report (EESR) dated Dec. 19, 2018 issued in European Application No. 18184551.2.
Notice of Allowance dated Sep. 15, 2020 issued in related U.S. Appl. No. 16/040,458.
Office Action (Non-Final Rejection) dated Oct. 7, 2020 issued in related U.S. Appl. No. 16/040,472.

* cited by examiner

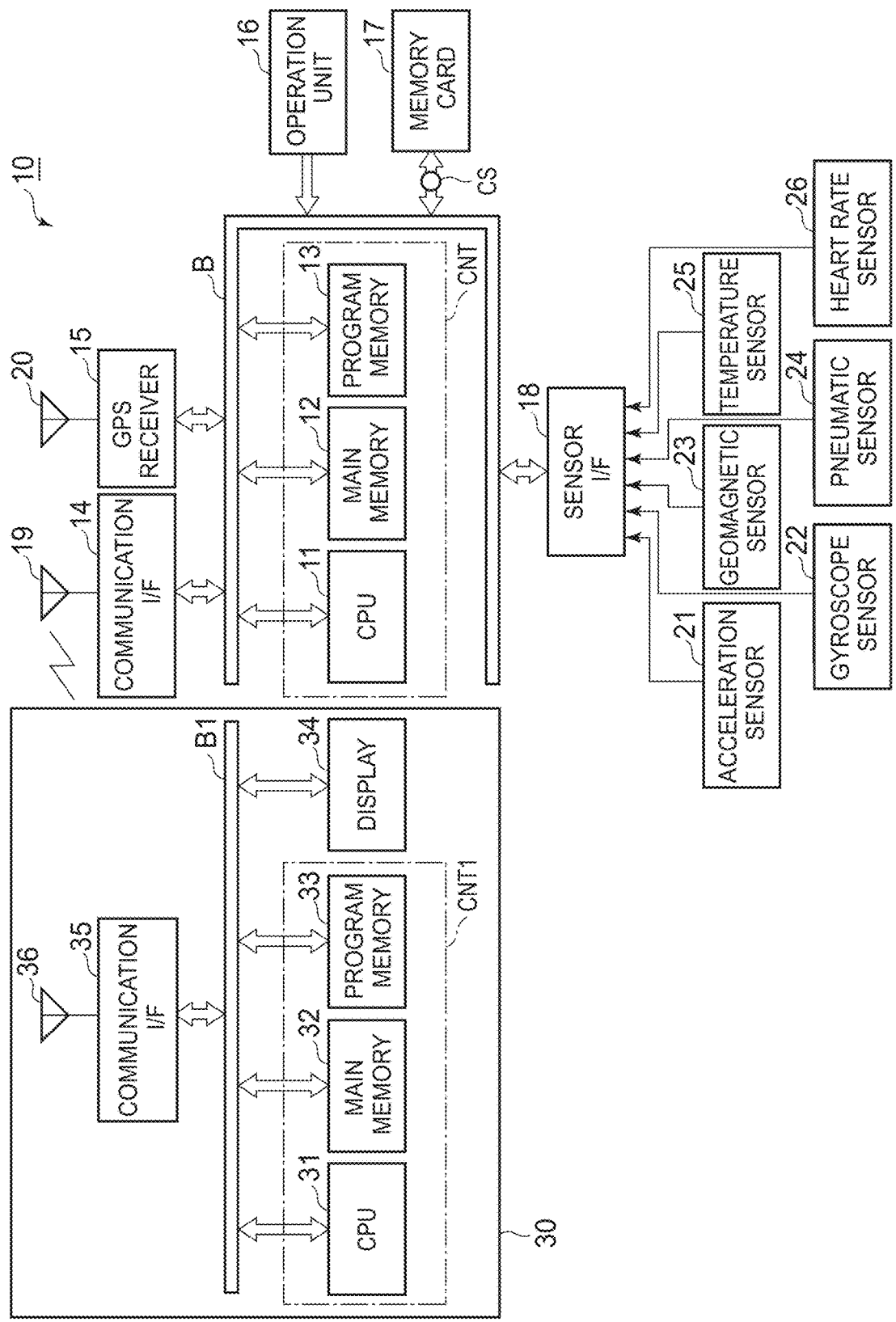

INPUT SIGNAL

CORRELATION COEFFICIENT

XV. LOCAL MAXIMUM OF HIGH-FREQUENCY WAVES DUE TO NOISE

FOR SMOOTHLY PAVED ROAD SURFACE

FOR ROUGH ROAD SURFACE

INFLUENCES FROM DISTURBANCE ARE SMALL

INFLUENCES FROM DISTURBANCE ARE LARGE

FIG. 27A
SEATED/STANDING
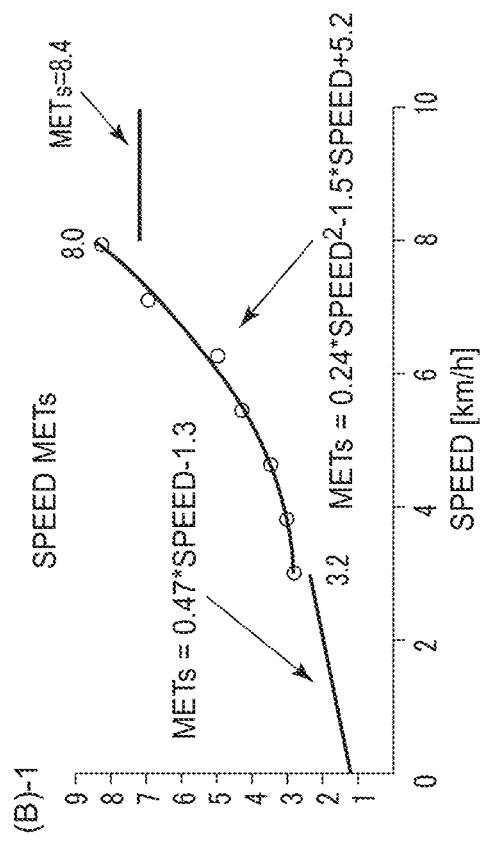
(A)-1: SPEED METs, METs=15.8, 36.76, METs = 0.47*SPEED-1.63, METs=1.8, 7.23
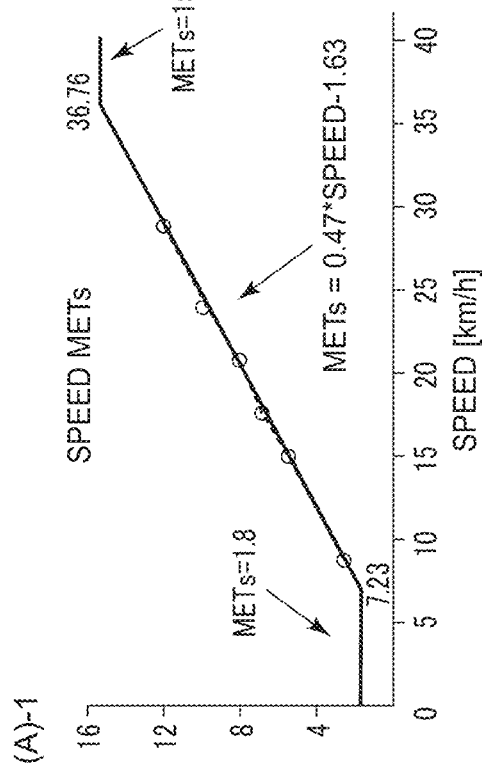
(A)-2: GRADIENT METs, METs = 0.55*GRADIENT
FIG. 27B
WALKING
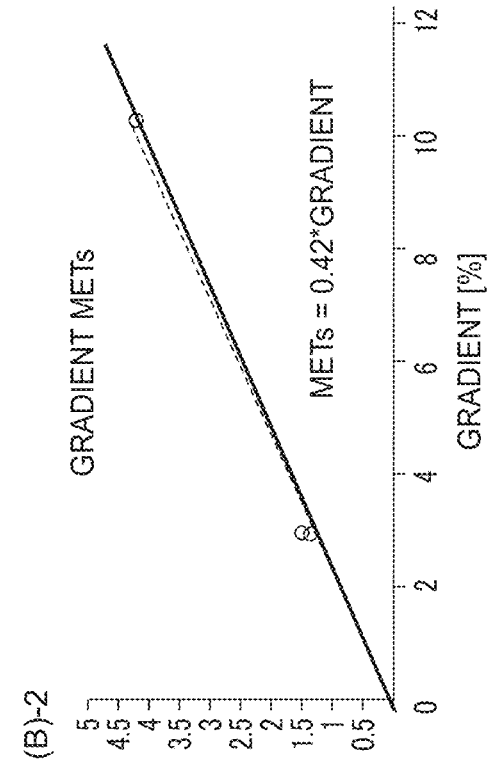
(B)-1: SPEED METs, METs=8.4, 8.0, METs = 0.24*SPEED²-1.5*SPEED+5.2, METs = 0.47*SPEED-1.3, 3.2
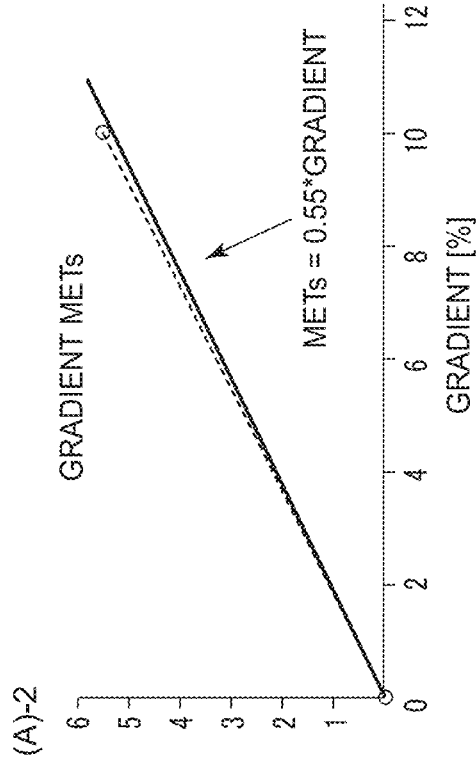
(B)-2: GRADIENT METs, METs = 0.42*GRADIENT

FIG. 30

| ACTIVITY | ITEM | TARGET ACTION | MINIMUM DIVIDING WIDTH |
|---|---|---|---|
| CYCLING<br><br>ACTION CATEGORY:<br>SEATED<br>STANDING<br>INERTIAL RUNNING<br>WALKING<br>STOP | SPEED | SEATED,STANDING,INERTIAL RUNNING | 2km/h |
| | FORWARD-TILTING ANGLE | SEATED,STANDING,INERTIAL RUNNING | 2deg |
| | GEAR VALUE | SEATED,STANDING | 0.3m/rev |
| | CADENCE | SEATED,STANDING,WALKING | 2rpm |
| | ALTITUDE | SEATED,STANDING,INERTIAL RUNNING,WALKING,STOP | 5m |
| | TEMPERATURE | SEATED,STANDING,INERTIAL RUNNING,WALKING,STOP | 1°C |
| | GRADIENT | SEATED,STANDING,INERTIAL RUNNING | 1% |
| | LATERAL-TILTING ANGLE | SEATED,STANDING,INERTIAL RUNNING | 1deg |
| TREKKING<br><br>ACTION CATEGORY:<br>WALKING<br>RUNNING<br>VEHICLES<br>STOP | SPEED | WALKING, RUNNING | 0.5km/h |
| | ALTITUDE | WALKING, RUNNING,VEHICLES,STOP | 5m |
| | TEMPERATURE | WALKING, RUNNING,VEHICLES,STOP | 1°C |
| | SLOPE ANGLE | WALKING, RUNNING | 1° |

ACTIVITY RECORDING DATA PROCESSING APPARATUS

CROSS-REFERENCE TO RELATED APPLICATIONS

This application is based upon and claims the benefit of priority under 35 USC 119 of Japanese Patent Application No. 2017-150670 filed on Aug. 3, 2017, the entire disclosure of which, including the description, claims, drawings, and abstract, is incorporated herein by reference in its entirety.

FIELD OF THE INVENTION

The present invention relates to an activity recording data processing apparatus.

BACKGROUND OF THE INVENTION

Conventionally devices called cycle computers or cyclo-computers (the term coined by combining "cycle" and "microcomputer") have been used as a data logger for cycling to record various types of data during cycling.

A cycle computer of this kind includes a GPS (Global Positioning System) receiver and various types of sensors, such as a speed sensor and a cadence sensor, and so can record the travelling track during the cycling or data from the various types of sensors.

In general it is important to process data acquired and analyzed by such a device to be an appropriate form in accordance with the purpose. For instance, JP-T-2013-543156 discloses a technique of dividing the data on work-out acquired by a mobile device based on a threshold set by a user, and color-coding the divided data with a plurality of colors as needed to present the data to the user visually.

SUMMARY OF THE INVENTION

JP-T-2013-543156 color-codes the data acquired during workout. Such color-coding of the data during various types of activity is not uniform, and various processing is performed depending on the purpose or the characteristics of data.

The present invention aims to provide an activity recording data processing apparatus, a method for processing activity recording data, and a program for processing activity recording data so as to allow data during various types of activity to be processed in accordance with the purpose and the characteristics of the data.

An activity recording data processing apparatus according to one aspect of the present invention includes a processor; and a storage unit configured to store a program that the processor executes, wherein the processor implements processing including the following processing in accordance with the program stored in the storage unit: acquisition processing of acquiring data obtained for a series of activity and action estimation information on the series of activity, the action estimation information being associated with the data; extraction processing of extracting partial data of the data based on the action estimation information; and clustering processing of performing clustering of the partial data.

BRIEF DESCRIPTION OF THE SEVERAL VIEWS OF THE DRAWING

FIG. 2B is a block diagram showing the functional configuration of an electronic circuit of a wearable terminal and an external device according to one embodiment in another aspect of the present invention.

FIGS. 11A1-11B2 show an example of the correction between local extrema (S222) for the output from the gyroscope sensor in FIG. 10 according to the embodiment.

FIGS. 27A and 27B show an example of characteristics of METs values during seated, standing and walking according to the embodiment.

FIG. 30 shows an example of the look-up table used for clustering according to the embodiment.

DETAILED DESCRIPTION OF THE INVENTION

Figure 1B:
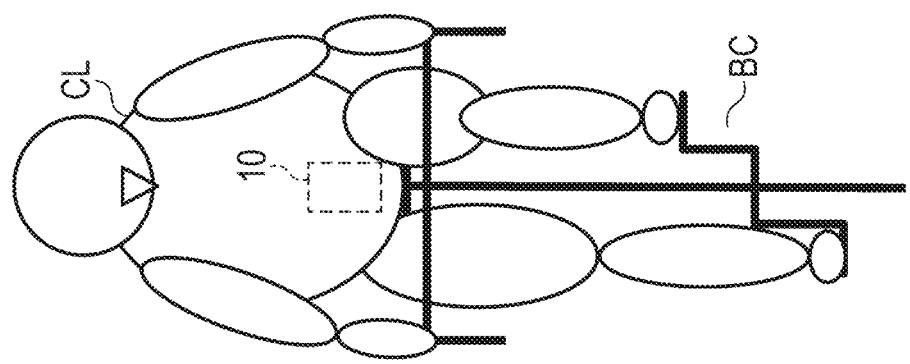
FIGS. 1A and 1B show an example of the wearable device in use during cycling according to one embodiment of the present invention.

Referring to the drawings, the following describes one embodiment of the present invention in details when the present invention is applied to a wearable device.

The present embodiment describes the case where the present invention is applied to a wearable device dedicated to outdoor sports particularly, such as cycling, trekking, and trail running.

Figure 1A:
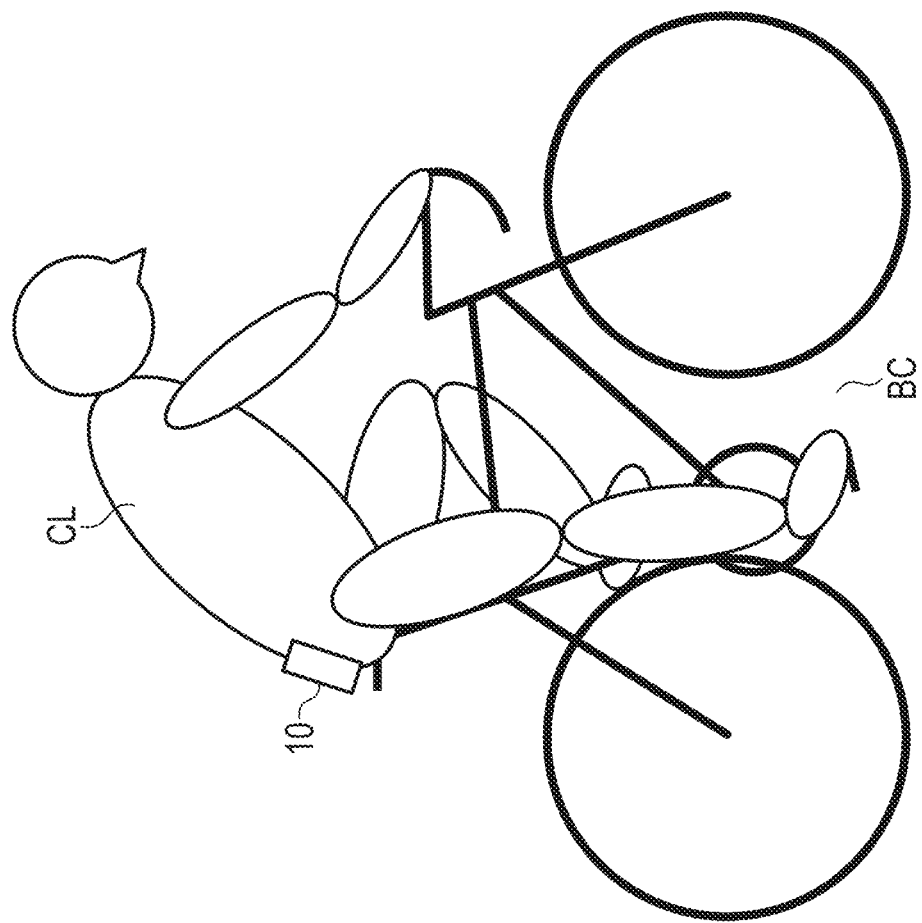

FIGS. 1A and 1B show an example of a cyclist CL riding on a bicycle BC for cycling while wearing a wearable device 10. The cyclist CL wears the wearable device 10 at a center of the lower back by securing the wearable device at a belt of a cycling pant, for example, with a clip as an accessory of the body of the wearable device 10.

Figure 2A:
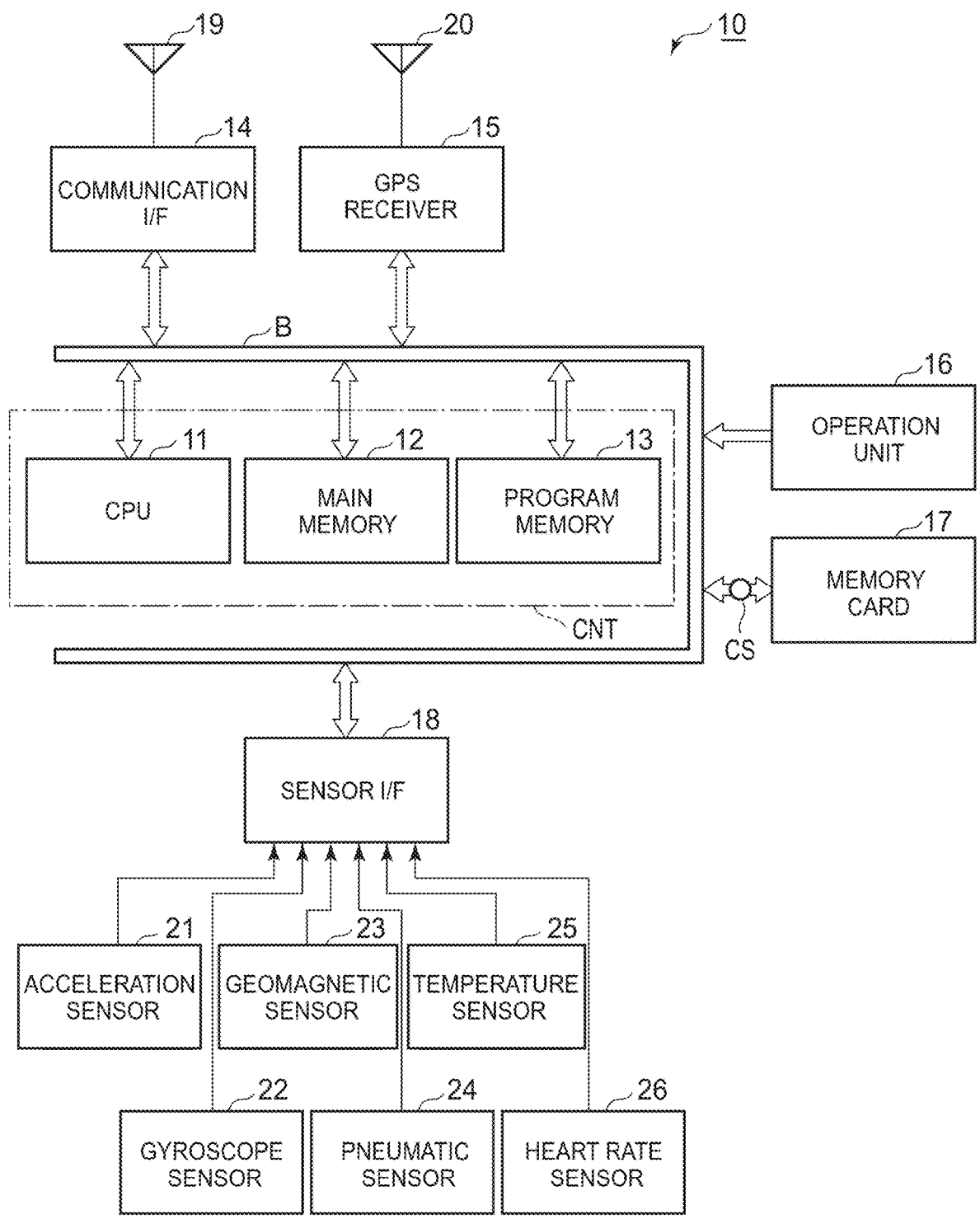
FIG. 2A is a block diagram showing the functional configuration of an electronic circuit of a wearable terminal according to one embodiment in one aspect of the present invention.

FIG. 2A is a block diagram of the functional configuration of an electronic circuit of the wearable device 10 in one aspect of the present invention. In this drawing, this wearable device 10 operates mainly with a controller CNT including a CPU 11, a main memory 12 and a program memory 13.

The CPU 11 reads an operation program and various types of fixed data stored in the program memory 13 including a non-volatile memory, such as a flash memory, and decompresses and stores the program or the data into the main memory 12 including a SRAM or the like. Then the CPU 11 executes the operation program sequentially to control the operations described later in an integrated manner. Processors other than the CPU, e.g., ASIC (Application Specification Integrated Circuit) or FPGA (Field Programmable Gate Array) may be used for this purpose.

To this CPU 11, the main memory 12, and the program memory 13, a communication interface (I/F) 14, a GPS receiver 15, an operation unit 16, a memory card 17 and a sensor interface (I/F) 18 are connected via a bus B.

The communication interface 14 is a circuit to exchange data with a not-illustrated external device, such as a smartphone, a personal computer (PC), or a digital camera via an antenna 19. The data is exchanged based on wireless LAN techniques complying with the standard of IEEE802.11a/11b/11g/11n and near field communication techniques complying with Bluetooth (registered trademark) or Bluetooth (registered trademark) LE (Low Energy), for example.

The GPS receiver 15 receives radio waves coming from a plurality of GPS satellites (not illustrated) via a GPS antenna 20, and calculates the absolute three-dimensional coordinate position (latitude/longitude/altitude) of the current position and the current time.

These GPS antenna 20 and GPS receiver 15 may be of a type that can be used with a satellite positioning system other than the GPS, such as GLONASS (GLObal NAvigation Satellite System) or Quasi-Zenith Satellite System (QZSS) that is a Japanese regional navigational satellite system. In that case, the GPS antenna and the GPS receiver may receive radio waves coming from such a satellite as well, and may calculate the absolute three-dimensional coordinates of the current position and the current time more precisely.

In that case, when the following description refers to GPS positioning for the operation, the operation includes the positioning with such a satellite positioning system other than the GPS as well.

The operation unit 16 receives a user's operation with a power key, a setting key to set activity, and other keys to instruct starting/ending of the measurement of this wearable device 10, and transmits a signal of the operated key to the CPU 11.

The memory card 17 is detachably attached to this wearable device 10 via a card slot CS. If wireless connection to an external device fails, for example, the memory card can record various types of data detected by the wearable device 10.

The sensor interface 18 connects an acceleration sensor 21, a gyroscope sensor 22, a geomagnetic sensor 23, a pneumatic sensor 24, a temperature sensor 25, and a heart rate sensor 26, for example. The sensor interface receives an output of the detection by each sensor and digitizes it, and sends the digitized data to the CPU 11.

The acceleration sensor 21 detects the acceleration along each of the three axes that are orthogonal to each other to detect the posture (including the direction of the acceleration of gravity) of the member who wears this wearable device 10 and the direction of external force applied.

The gyroscope sensor 22 includes a vibrating gyroscope to detect angular velocity along each of the three axes that are orthogonal to each other. The gyroscope sensor detects the changing rate in posture of the wearable device 10. The gyroscope sensor may be an angular-velocity sensor other than the vibrating gyroscope.

The geomagnetic sensor 23 includes a magnetoresistance effect device (MR sensor) to detect the geomagnetic intensity relative to the magnetic north direction along each of three axes that are orthogonal to each other. The geomagnetic sensor detects the bearing of this wearable device 10 during the movement, including the magnetic north direction.

In some environments, such as indoors or in a tunnel, the absolute value of the current position of the wearable device cannot be detected with the GPS antenna 20 and the GPS receiver 15. Then the outputs of the detection by these acceleration sensor 21, gyroscope sensor 22 and geomagnetic sensor 23 may be combined, which can obtain the track of the action by the user in such an environment as well with consideration given to the bearing based on the autonomous navigation (dead reckoning (DR)) in the three-dimensional space.

The pneumatic sensor 24 detects atmospheric pressure to detect a change in the atmospheric pressure. The detection may be combined with information on the altitude obtained from the output of the GPS receiver 15 to estimate the altitude, if GPS positioning fails in the future.

The temperature sensor 25 detects temperatures.

The heart rate sensor 26 receives a detection signal from a device (not illustrated) to detect electric potentials of the heart that is attached to the left chest of the cyclist CL wearing this wearable device 10, and detects the heart rate of the cyclist CL.

FIG. 2B is a block diagram of the functional configuration of an electronic circuit of the wearable device 10 and an external device 30 in another aspect of the present invention. In this drawing, since the wearable device 10 is the same as that in FIG. 2A, the description is omitted.

The external device 30 may be an electronic device, such as a smartphone or a PC. The external device 30 operates mainly with a controller CNT 1 including a CPU 31, a main memory 32 and a program memory 33.

The CPU 31 reads an operation program and various types of fixed data stored in the program memory 33 including a non-volatile memory, such as a flash memory, and decompresses and stores the program or the data into the main memory 32 including a SRAM or the like. Then the CPU 31 executes the operation program sequentially to control the operations described later in an integrated manner. Processors other than the CPU, e.g., ASIC (Application Specification Integrated Circuit) or FPGA (Field Programmable Gate Array) may be used for this purpose.

To this CPU 31, the main memory 32, the program memory 33 and a display 34, a communication interface (I/F) 35 is connected via a bus B1. The communication interface 35 is a circuit to exchange data with the wearable device 10 via an antenna 36. The data is exchanged based on near field communication techniques as stated above, for example. That is, the communication interface 14 of the wearable device 10 exchanges data with the communication interface 35 of the external device 30 via the antennas 19 and 36.

The following describes the operation of the present embodiment.

The following describes a series of processing when the cyclist CL wearing the wearable device 10 sets the operating mode at "cycling" before cycling to start the measurement and ends the measurement at the timing when the cycling ends, and after the cycling, analyzes the route passed through during the cycling.

For instance, the wearable device 10 of FIG. 2A can execute a series of processing from the measurement to the analysis. The wearable device 10 of FIG. 2B can execute a part of a series of processing from the measurement to the analysis, and the external device 30, such as a smartphone or a PC, executes the remaining processing.

The following describes the case where the wearable device 10 of FIG. 2A executes a series of processing from the measurement to the analysis.

Figure 3:
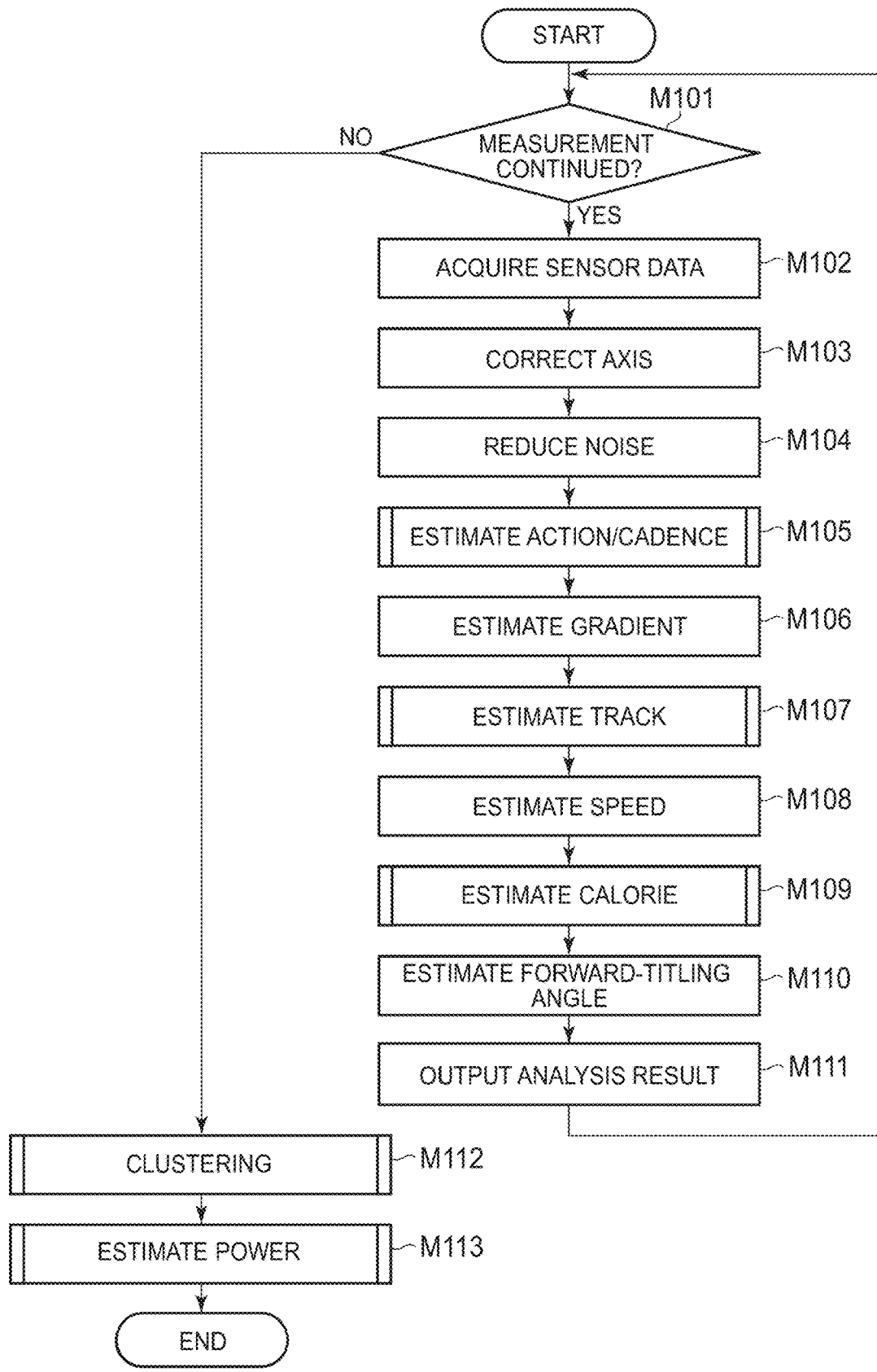
FIG. 3 is a flowchart to show the processing of a main routine according to the embodiment.

FIG. 3 is a flowchart to show the processing of a main routine executed by the CPU 11. At the beginning of the processing, the CPU 11 starts the processing in response to the user's operation of a start/end key of the operation unit 16. The CPU 11 confirms the measurement operation going on (Yes at Step M101), and acquires detection data from each of the acceleration sensor 21, the gyroscope sensor 22, the geomagnetic sensor 23, the pneumatic sensor 24, the temperature sensor 25, and the heart rate sensor 26 via the sensor interface 18 (Step M102).

The measurement operation by these various types of sensors is performed at predetermined time intervals (this is defined as an analysis cycle), e.g., at the frequency of once a second. Then the CPU 11 records the sensor data soon on the memory card 17, and basically executes the following operation based on the sensor data of the past five seconds.

Firstly the CPU 11 executes the processing to correct axis based on the output from the acceleration sensor 21, the gyroscope sensor 22 and the geomagnetic sensor 23 (Step M103).

Figure 4A:
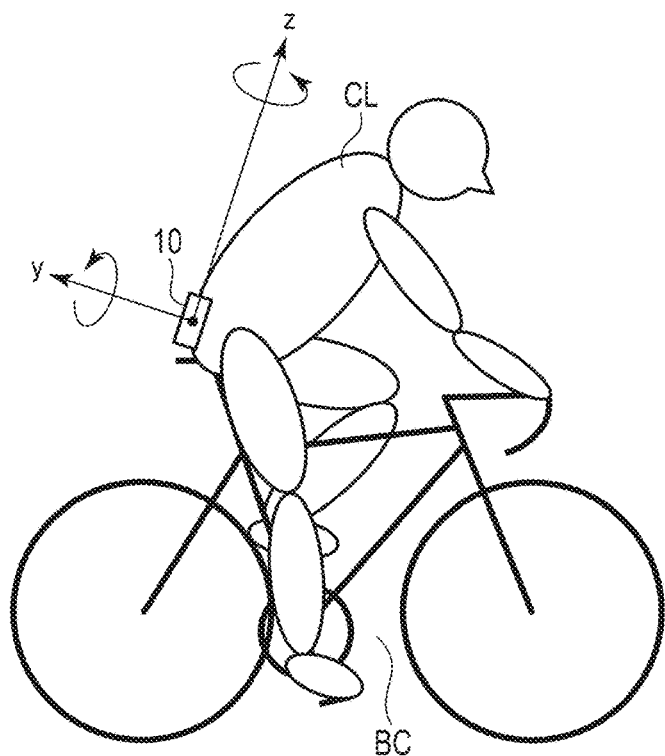
FIGS. 4A, 4B-1 and 4B-2 explain the processing of the axis correction according to the embodiment.

FIGS. 4A, 4B-1 and 4B-2 explain the processing of this axis correction. FIG. 4A shows y-axis direction and z-axis direction before the axis correction. More specifically as shown in FIG. 4A, z-axis direction, which has to be parallel to the vertical direction, and y-axis direction, which has to be parallel to the travelling direction of the cyclist CL, are inclined by the inclining angle of the lower back of the cyclist CL wearing the wearable device 10.

Figures 1, 4B:
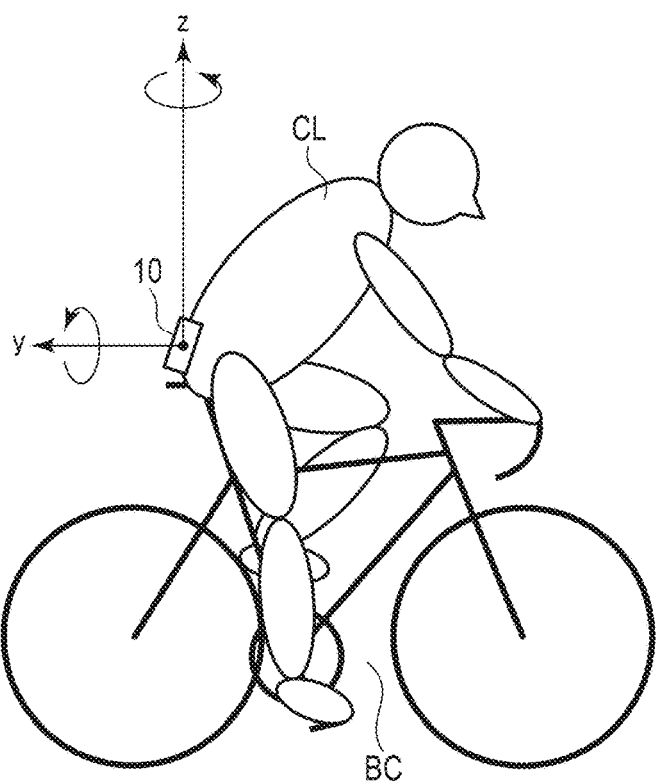
Figures 2, 4B:
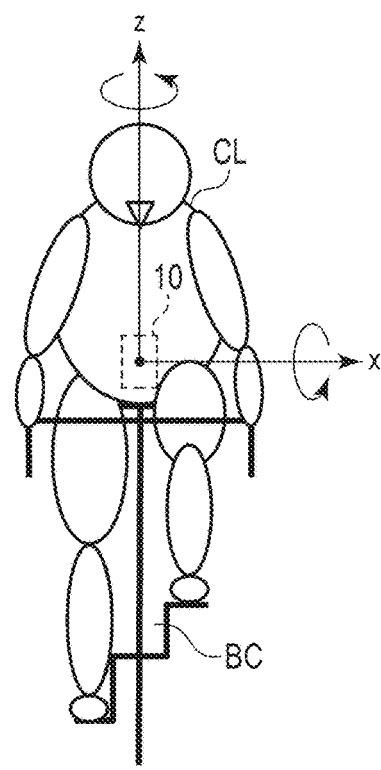

Therefore the CPU 11 corrects the detection data of the acceleration sensor 21 based on the direction of the acceleration of gravity obtained from the acceleration sensor 21. The correction is made so that, as shown in FIG. 4B-1 and FIG. 4B-2, the antigravity direction is the positive direction in z-axis, the opposite direction of the travelling direction of the cyclist CL is the positive direction in y-axis, and the left direction orthogonal to the travelling direction of the cyclist CL is the positive direction in x-axis. Note here that the x-axis direction and the y-axis direction are set so that the direction where the cyclist CL faces is the front face.

In this way, the axes shown in FIG. 4A that are detected from various types of sensors are corrected as in FIGS. 4B-1 and 4B-2. In the present embodiment, the axes are defined as in FIGS. 4B-1 and 4B-2.

Additionally the detection data of the gyroscope sensor 22 is corrected so that the angular velocity rotating clockwise from the origin is positive angular velocity relative to the positive directions of x-, y-, and z-axes.

After this axis correction, the CPU 11 executes low-pass filter processing and outlier-removing processing of the data of these sensors to reduce the noise component (Step M104).

Based on the sensor data subjected to such axis correction and noise-component reduction processing, the CPU 11 estimates the action and the cadence of the cyclist CL (Step M105).

Note here that action estimation means estimation of a continuous action by the cyclist CL for a certain duration during cycling based on the data detected by various type of sensors. The present embodiment classifies the action into any one of the following five types by the action estimation: that is, seated: the cyclist is pedaling while sitting on the saddle of the bicycle BC, standing: the cyclist is pedaling while standing up from the saddle, inertial running: the bicycle BC travels by an inertial force while the cyclist is not pedaling, walking: the cyclist is dismounted from the bicycle BC and is walking (including walking while pushing the bicycle BC forward), and stop: actions other than the above. This is mainly assumed as a stopping state.

Cadence estimation means estimations on three actions of the above, including seated, standing and walking so as to estimate the rotating speed of the crank pedal of the bicycle BC (for seated and standing) or the number of steps (for walking) per unit time (typically one minute).

Figure 5:
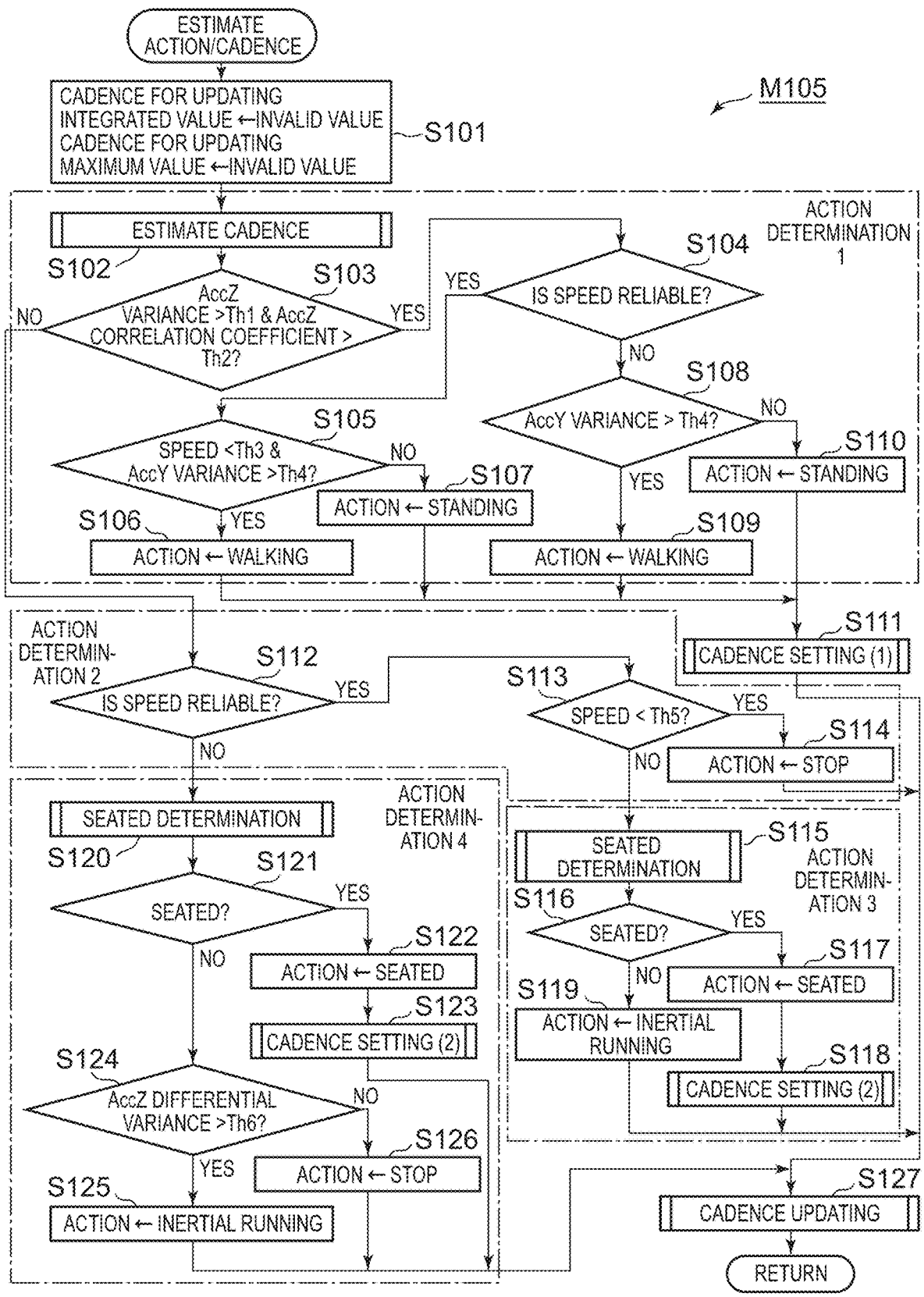
FIG. 5 is a flowchart of a subroutine to show the action/cadence estimation (M105) in FIG. 3 according to the embodiment.

FIG. 5 is a flowchart of a subroutine to show the action/cadence estimation at Step M105 as stated above in details. At the beginning of this processing, the CPU 11 sets, for initial setting, an invalid value for both of the values of cadence for updating the integrated value and of cadence for updating the maximum value (Step S101).

Next the CPU 11 executes action determination 1 from Steps S102 to S110. In this action determination 1, the CPU 11 determines whether the action is "standing or walking" or other actions. More specifically during standing and walking, the lower back of the cyclist CL moves up and down periodically. Therefore the output AccZ of the acceleration sensor 21 in the z-axis direction has noticeable periodicity. This determination is therefore made based on the output AccZ.

At the beginning of this processing, the CPU 11 executes cadence estimation described later in details so as to calculate an autocorrelation coefficient of the output AccZ of the acceleration sensor 21 in the z-axis direction (Step S102).

Next the CPU 11 determines whether the output AccZ of the acceleration sensor 21 in the z-axis direction has variance larger than a first threshold Th1, e.g., 1.4, and whether the autocorrelation coefficient of the output AccZ of the acceleration sensor 21 in the z-axis direction is larger than a second threshold Th2, e.g., 0.47. Based on the result of the determination, the CPU 11 removes small amplitude, such as vibrations from the road surface, as noise, and executes the action determination 1 (Step S103).

At this Step S103, when the CPU 11 determines that the action is standing or walking because the output AccZ of the acceleration sensor 21 in the z-axis direction has variance larger than the first threshold Th1 and the autocorrelation coefficient of the output AccZ is larger than the second threshold Th2 (Yes at Step S103), the CPU 11 determines whether information on the travelling speed is reliable or not (Step S104). When the GPS positioning information is reliable, the CPU 11 determines that information on the travelling speed is reliable, which will be described later in details.

When the CPU 11 determines that the information on the travelling speed is reliable because such information is stably obtained (Yes at Step S104), the CPU 11 next determines whether the speed is smaller than a third threshold Th3, e.g., 2.4 [m/sec.] and whether the output AccY of the acceleration sensor 21 in the y-axis direction has variance larger than a fourth threshold Th4, e.g., 2.0 (Step S105). That is, if the travelling speed is smaller than a certain value and the acceleration in the travelling direction has large variance, the action is determined as walking because there is impact (brake shock) especially at the landing of the foot.

When the CPU 11 determines that the travelling speed is smaller than the certain value and the acceleration in the travelling direction has large variance because the travelling speed is smaller than the third threshold Th3 and the output AccY of the acceleration sensor 21 in the y-axis direction has variance larger than the fourth threshold Th4 (Yes at Step S105), the CPU 11 determines that the action at this time is walking (Step S106) and ends the action determination 1.

At this Step S105, when the CPU 11 determines that the travelling speed is the certain value or larger or the acceleration in the travelling direction has small variance because the travelling speed is the third threshold Th3 or larger or the output AccY of the acceleration sensor 21 in the y-axis direction has variance of the fourth threshold Th4 or smaller (No at Step S105), the CPU 11 determines that the action at this time is standing (Step S107) and ends the action determination 1.

At Step S104 as stated above, when the CPU 11 determines that the information on the travelling speed is not reliable because such information cannot be obtained stably (No at Step S104), the CPU 11 next determines only whether the output AccY of the acceleration sensor 21 in the y-axis direction has variance larger than the fourth threshold Th4, e.g., 2.0 (Step S108). That is, if the acceleration in the travelling direction has large variance, the action is determined as walking because there is impact (brake shock) especially at the landing of the foot.

When the CPU 11 determines that the acceleration in the travelling direction has large variance because the output AccY of the acceleration sensor 21 in the y-axis direction has variance larger than the fourth threshold Th4 (Yes at Step S108), the CPU 11 determines that the action at this time is walking (Step S109) and ends the action determination 1.

At this Step S108, when the CPU 11 determines that the acceleration in the travelling direction has small variance because the output AccY of the acceleration sensor 21 in the y-axis direction has variance of the fourth threshold Th4 or smaller (No at Step S108), the CPU 11 determines that the action at this time is standing (Step S110) and ends the action determination 1.

After the action determination at these steps S106, S107, S109 and S110, the CPU 11 sets a first cadence value corresponding to standing or walking (cadence setting (1)) (Step S111). This setting of the first cadence value is described later in details.

At Step S103, when the CPU 11 determines that the action is neither standing nor walking because the output AccZ of the acceleration sensor 21 in the z-axis direction has variance of the first threshold Th1 or smaller or the autocorrelation coefficient of the output AccZ is the second threshold Th2 or smaller (No at Step S103), the CPU 11 determines whether information on the travelling speed is reliable or not (Step S112). When the GPS positioning information is reliable, the CPU 11 determines that information on the travelling speed is reliable, which will be described later in details.

When the CPU 11 determines that the information on the travelling speed is reliable because such information is stably obtained (Yes at Step S112), the CPU 11 next determines whether the action is stop or not. This determination is made based on whether the speed is smaller or not than a fifth threshold Th5, e.g., 0.64 [m/sec.] (Step S113).

When the CPU 11 determines that the travelling speed is smaller than the fifth threshold Th5 (Yes at S113), the CPU 11 determines that the action at this time is stop (Step S114) and ends the action determination 2.

When a reliable travelling speed is smaller than a certain value, the CPU 11 may erroneously determine an unexpected action of the cyclist CL during stopping, such as doing exercise after stopping the bicycle BC, as seated or inertial running. The above processing avoids such an erroneous determination as much as possible.

When the CPU 11 determines at Step S113 that the travelling speed is the fifth threshold Th5 or larger (No at Step S113), the CPU 11 shifts to action determination 3 at Steps S115 to S119 to make a determination between inertial running and seated.

In this action determination 3, the CPU 11 executes seated determination as follows (Step S115).

Figure 6:
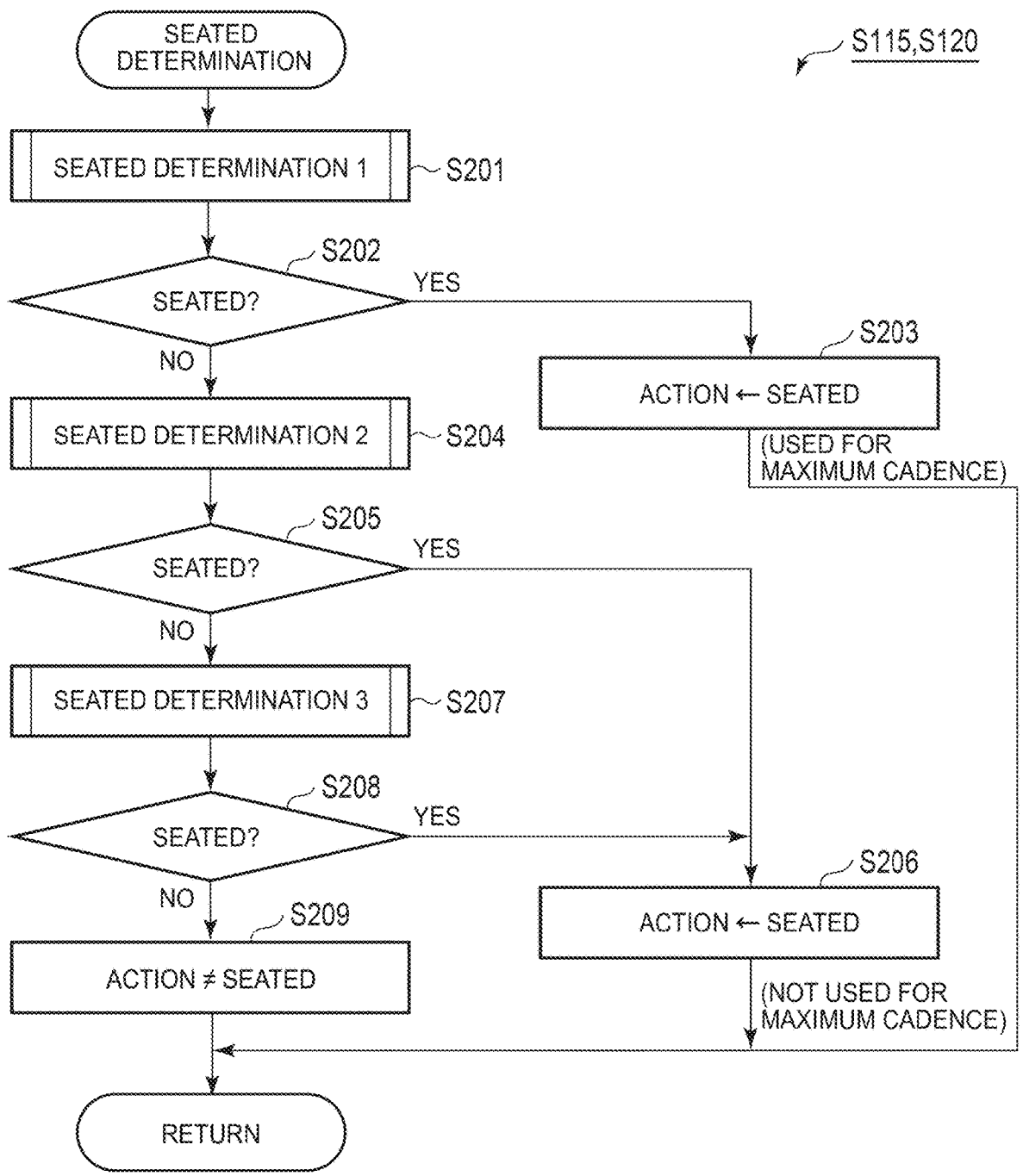
FIG. 6 is a flowchart to show a subroutine of the seated determination (S115, S120) in FIG. 5 according to the embodiment.

FIG. 6 is a flowchart to show a subroutine of the seated determination in details. Firstly the CPU 11 performs seated determination 1. In this determination, the CPU 11 determines whether the action is seated or not (Step S201). This determination is made based on whether the output GyrY in the y-axis direction and the output GyrZ in the z-axis direction of the gyroscope sensor 22 have periodicity or not, which are the features of seated.

Figure 7:
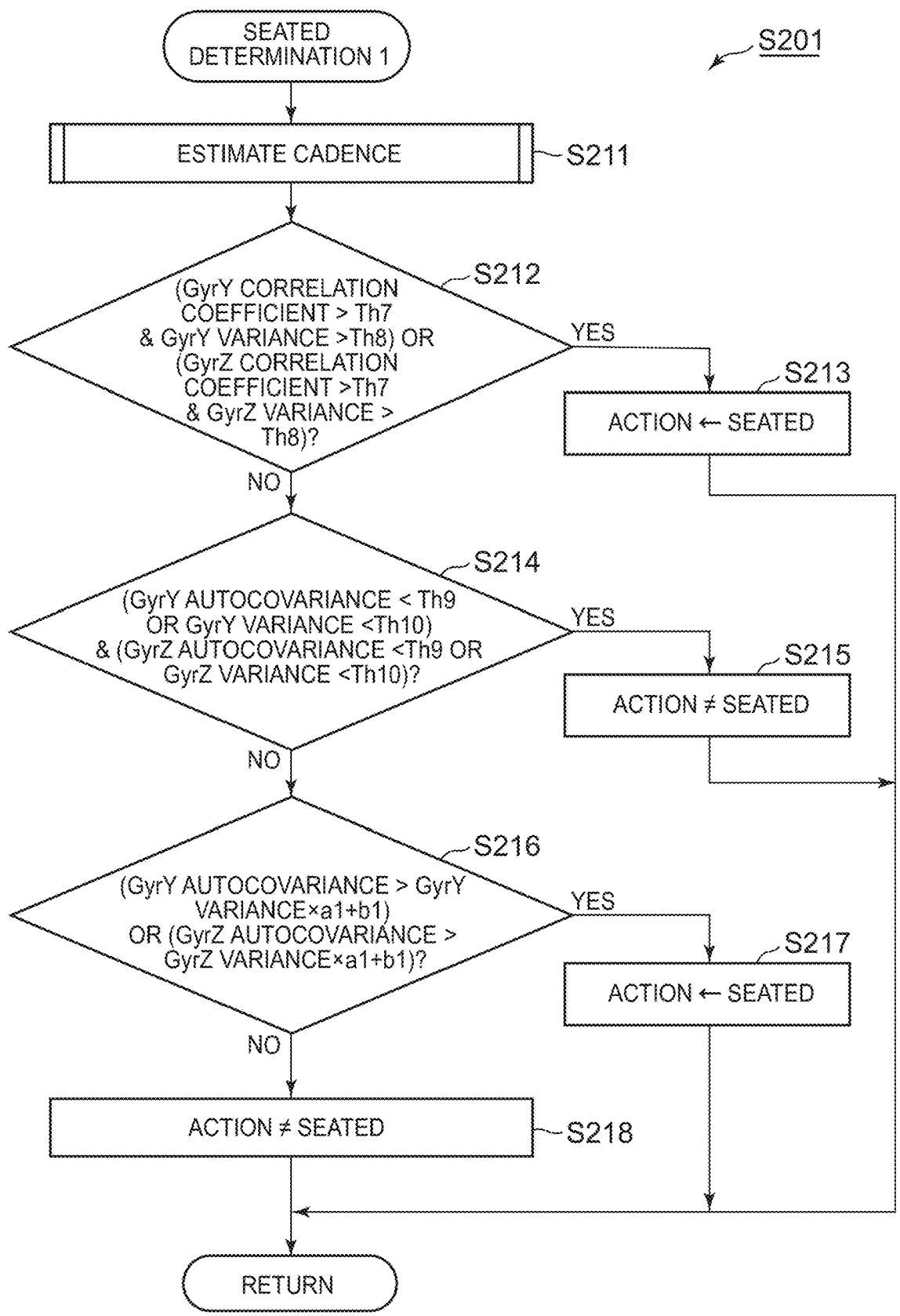
FIG. 7 is a flowchart to show a subroutine of the seated determination 1 (S201) in FIG. 6 in details according to the embodiment.

FIG. 7 is a flowchart to show a subroutine of this seated determination 1 in details. The output GyrY in the y-axis direction and the output GyrZ in the z-axis direction of the gyroscope sensor 22 are used for this determination because the rotary movement of the lower back of the cyclist CL during pedaling often appears in any one of the y-axis direction and the z-axis direction or in both of the directions, although there are differences between individuals.

The following describes how to detect the periodicity of the output GyrY in the y-axis direction and the output GyrZ in the z-axis direction of the gyroscope sensor 22.

Figure 8A:
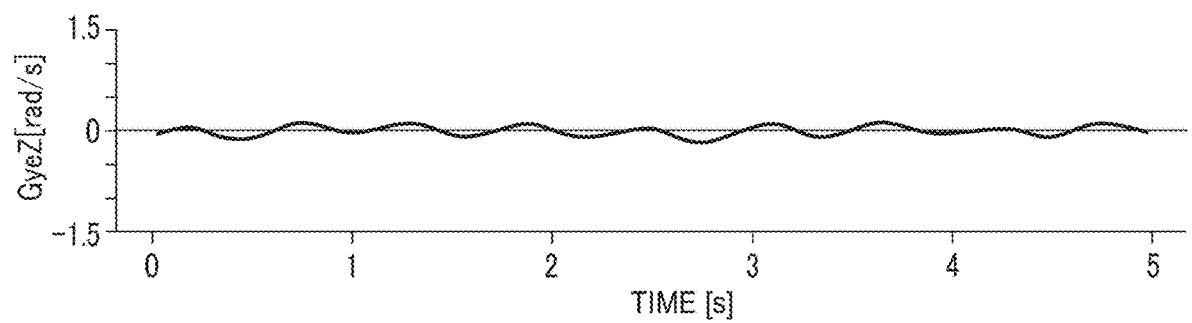
FIGS. 8A-8C show an example about how the output GyrY in the y-axis direction of the gyroscope sensor 22 varies among three cyclists CL during seated according to the embodiment.
Figure 8B:
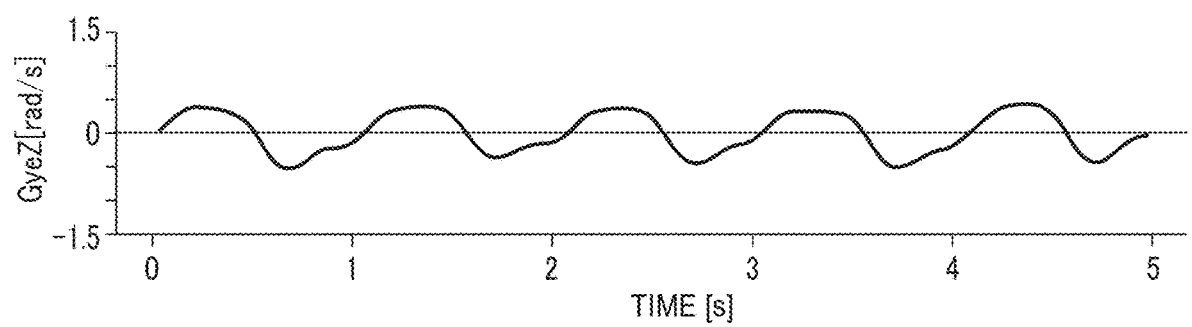
Figure 8C:
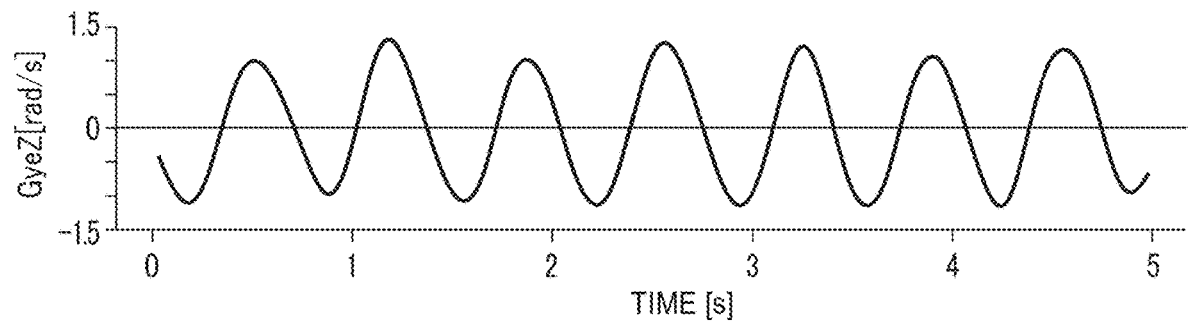

FIGS. 8A-8C show an example about how the output GyrZ in the z-axis direction of the gyroscope sensor 22 for three cyclists CL, including CL-A, CL-B and CL-C, changes during seated. In this way, there are large differences in movement between individuals during seated operation. Therefore a seated determination is not enough if its periodicity is simply determined based on independent thresholds of the variance and of the autocorrelation coefficient.

Figure 9:
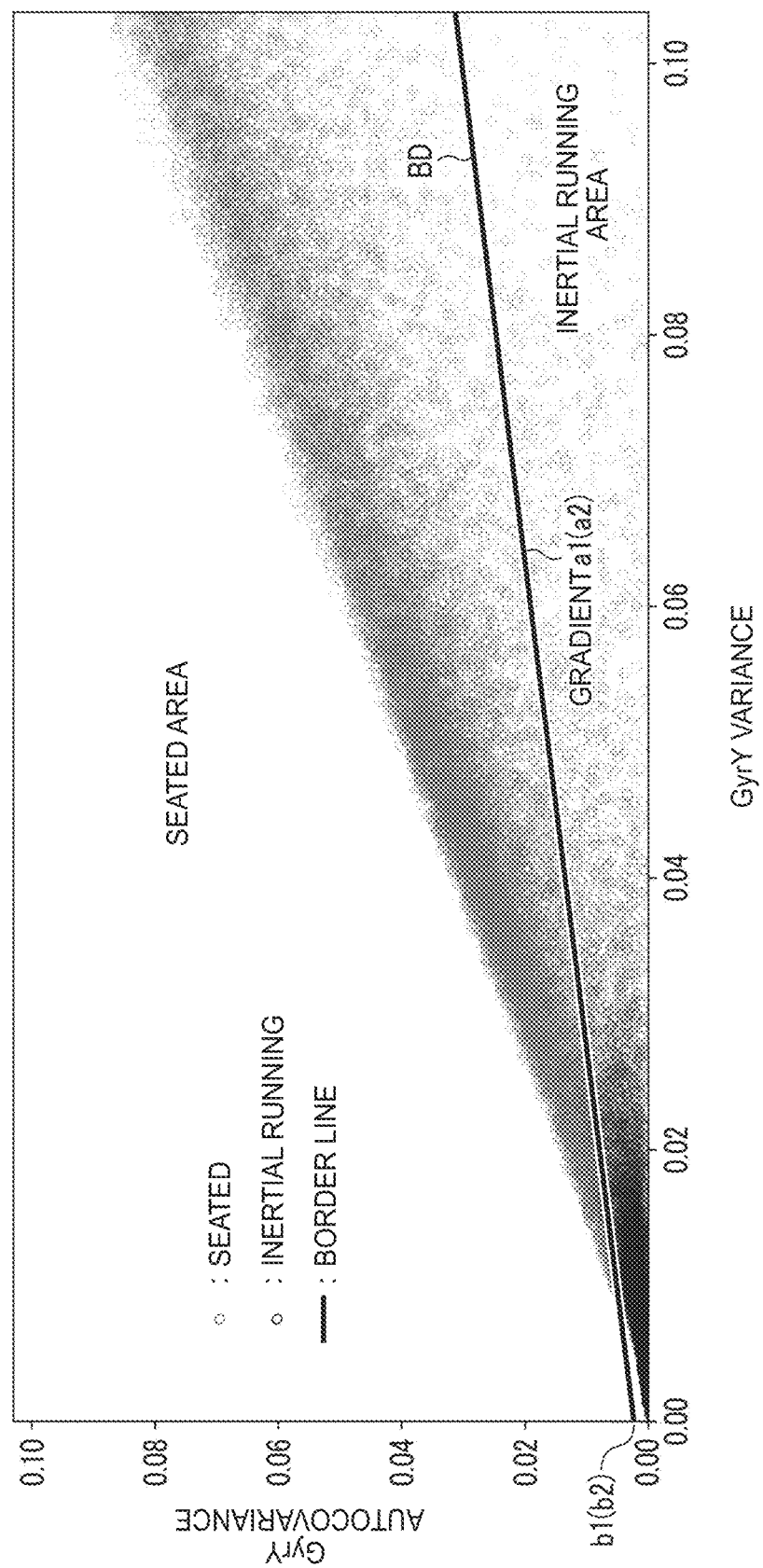
FIG. 9 shows an example of linear separation using a border line BD between variance and autocovariance according to the embodiment.

As shown in FIG. 9, the periodicity therefore is determined by linear separation using a border line BD between variance and autocovariance.

Such autocovariance is used instead of the autocorrelation coefficient because the autocorrelation coefficient is obtained by dividing autocovariance by variance. This can avoid double influences of the variance.

Thereby even when the motion of the lower back of the cyclist CL is small (which means that the variance is small) during seated operation, a determination may be made whether there is autocovariance or not, which corresponds to the variance, whereby the periodicity can be detected.

As shown in FIG. 9, another condition may be added to this linear separation. That is, if the variance is too small beyond a certain limit, this also is determined as not seated.

In FIG. 7 to show the specific processing, the CPU 11 firstly executes cadence estimation described later (Step S211).

Next the CPU 11 determines whether the autocorrelation coefficient of the output GyrY in the y-axis direction of the gyroscope sensor 22 is larger than a seventh threshold Th7, e.g., 0.51 and whether this output GyrY has variance larger than an eighth threshold Th8, e.g., 0.01, or determines whether the autocorrelation coefficient of the output GyrZ in the z-axis direction of the gyroscope sensor 22 is larger than the seventh threshold Th7 and whether this output GyrZ has variance larger than the eighth threshold Th8. The CPU 11 makes a determination of at least any one of them (Step S212).

In this determination at Step S212, the seventh threshold Th7 and the eighth threshold Th8 are set somewhat large. This is to extract the output GyrY in the y-axis direction and the GyrZ in the z-axis direction of the gyroscope sensor 22 having sufficiently large amplitude and having clear periodicity, which can determine that the action is clearly a seated operation.

When the CPU 11 determines that this condition is satisfied (Yes at S212), the CPU 11 determines that the action is seated (Step S213).

When the CPU 11 determines that the condition at Step S212 is not satisfied (No at Step S212), then the CPU 11 determines whether the autocovariance of the output GyrY in the y-axis direction of the gyroscope sensor 22 is smaller than a ninth threshold Th9, e.g., 0.0016 or whether this output GyrY has variance smaller than a tenth threshold Th10, e.g., 0.0047 and determines whether the autocovariance of the output GyrZ in the z-axis direction of the gyroscope sensor 22 is smaller than the ninth threshold Th9 and whether this output GyrZ has variance smaller than the tenth threshold Th10 (Step S214).

In this determination at Step S214, the output GyrY in the y-axis direction and the output GyrZ in the z-axis direction of the gyroscope sensor 22 having very small amplitude and having clearly low periodicity are extracted, whereby the CPU 11 can identify the case where the action is clearly not seated. To this end, the ninth threshold Th9 and the tenth threshold Th10 are set somewhat small.

When the CPU 11 determines that this condition is satisfied (Yes at Step S214), the CPU 11 determines that the action is not seated (Step S215).

When the CPU 11 determines that the condition at Step S214 is not satisfied (No at Step S214), then the CPU 11 determines whether the autocovariance of the output GyrY in the y-axis direction of the gyroscope sensor 22 is larger than the value obtained by multiplying the variance of the output GyrY by the gradient a1 of the border line BD in FIG. 9, e.g., 0.3113 and adding the value of contact (intercept) b1, e.g., 0.0018, or determines whether the autocovariance of the output GyrZ in the z-axis direction of the gyroscope sensor 22 is larger than the value obtained by multiplying the variance of the output GyrZ by the gradient a1 of the border line BD in FIG. 9 and adding the value of contact (intercept) b1. The CPU 11 makes a determination of at least one of them (Step S216).

As described above, since there are large differences between individuals in pedaling during the seated operation, it is difficult to evaluate the presence or not of the periodicity simply by setting a threshold for the variance. For instance, while the movement of one cyclist (FIG. 8C) is large and has periodicity, the movement of another cyclist (FIG. 8B or FIG. 8A) is intermediate or small but still having periodicity. Therefore it may be difficult to determine the periodicity of the movement simply by setting one threshold for variance as in Step S212 or Step S214. To solve this, at Step S216, seated determination is made by evaluating the autocovariance and the variance through regression of these two values instead of evaluating the correlation coefficient and the variance separately.

Seated determination is made by linear separation using the border line BD shown in FIG. 9. When the CPU 11 determines that the condition at Step S216 is satisfied (Yes at S216), the CPU 11 determines that the action is seated (Step S217). The determination at Step S216 enables seated determination when the variance is so small that the action is not determined as seated at Steps S212 and S214.

When the CPU 11 determines that the condition at Step S216 is not satisfied (No at Step S216), the CPU 11 determines that the action is not seated (Step S218).

After the seated determination 1 in FIG. 7 as stated above, the CPU 11 returns to the processing of FIG. 6. Then the CPU 11 determines whether the seated determination 1 determines the action as seated or not (Step S202).

When the CPU 11 determines that the action is seated (Yes at Step S202), then the CPU 11 determines again that the action is seated (Step S203) and that this determination is reliable. The CPU 11 then uses the cadence obtained during the cadence determination to calculate a maximum cadence value.

When the CPU 11 determines at Step S202 that the action is not seated (No at Step S202), the CPU 11 subsequently executes seated determination 2 (Step S204).

Figure 10:
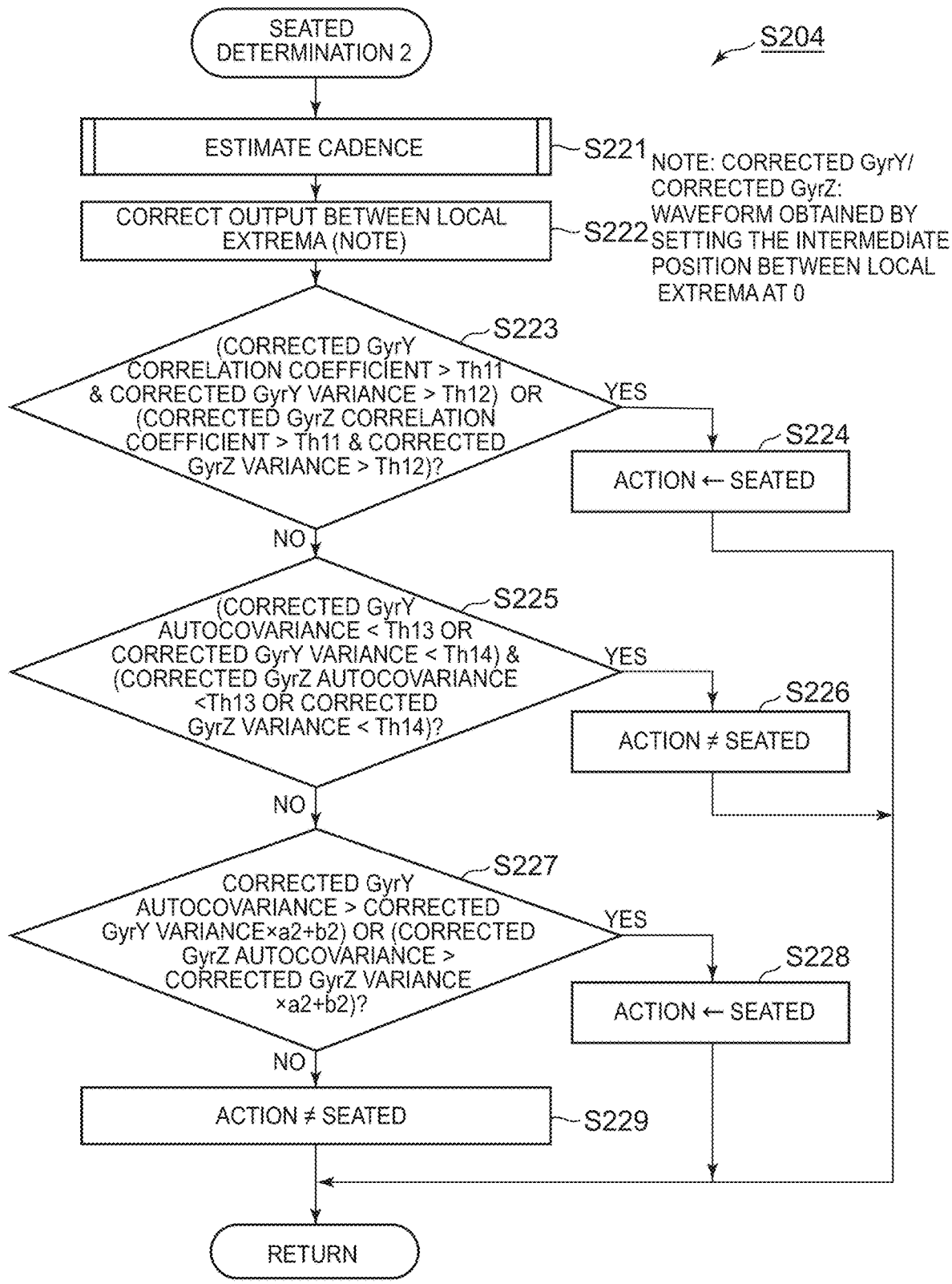
FIG. 10 is a flowchart to show a subroutine of the seated determination 2 (S204) in FIG. 6 in details according to the embodiment.

FIG. 10 is a flowchart to show a subroutine of this seated determination 2 in details. The CPU 11 firstly executes cadence estimation described later (Step S221).

After that the CPU 11 corrects the output GyrY in the y-axis direction and the output GyrZ in the z-axis direction of the gyroscope sensor 22 between their local maxima and local minima (Step S222).

Figures 1, 11A:
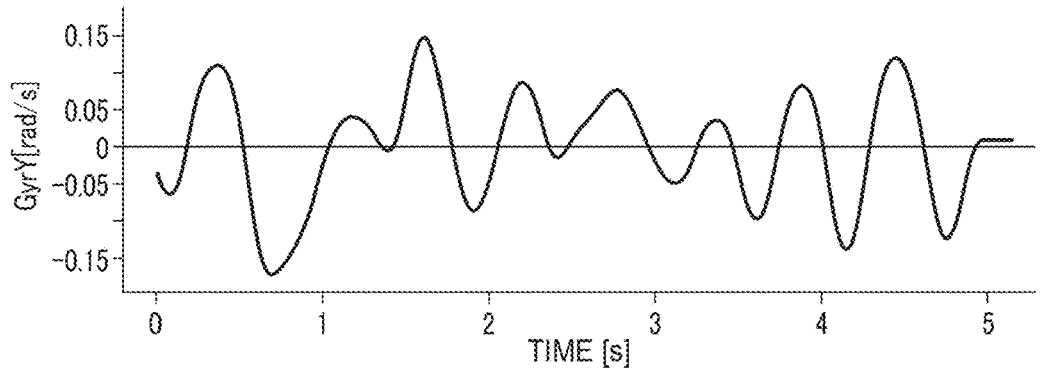
Figures 2, 11A:
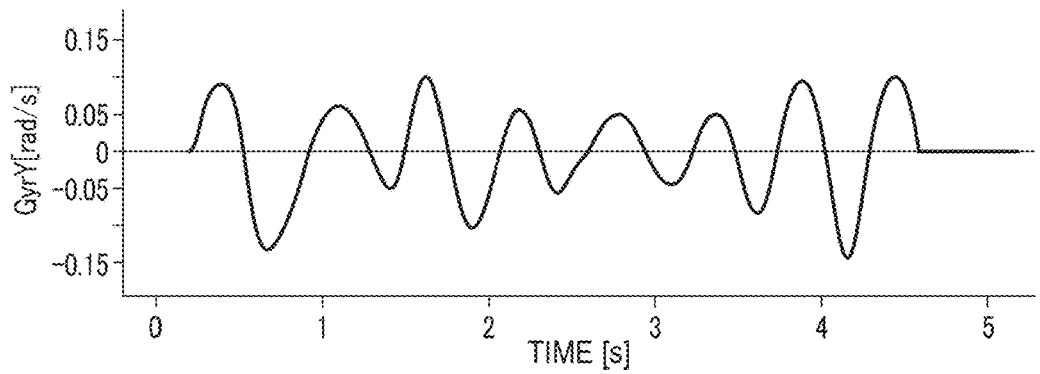

FIG. 11A-1 shows an example of the output GyrY in the y-axis direction of the gyroscope sensor 22 during seated before correction, and FIG. 11A-2 shows a result of the correction to set the middle position between the local extremum of the output GyrY in the y-axis direction at 0 (zero). FIG. 11A-1 shows the periodicity to some extent in the output GyrY in the y-axis direction of the gyroscope sensor 22. If this is directly used for the determination of seated as described later, the action is not determined as seated in some cases. To avoid this, the value at the middle position between local maxima and local minima of the output GyrY in the y-axis direction of the gyroscope sensor 22 is brought to 0 (zero) at Step S222. FIG. 11A-2 shows a successful example. In this way, when the output GyrY in the y-axis direction of the gyroscope sensor 22 is irregular and has small amplitude as well, the action can be determined as seated correctly by stabilizing the output for seated determination.

Figures 1, 11B:
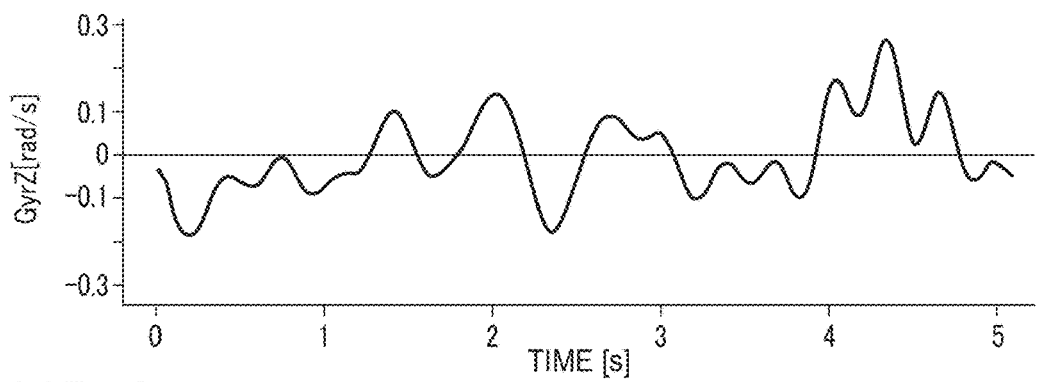
Figures 2, 11B:
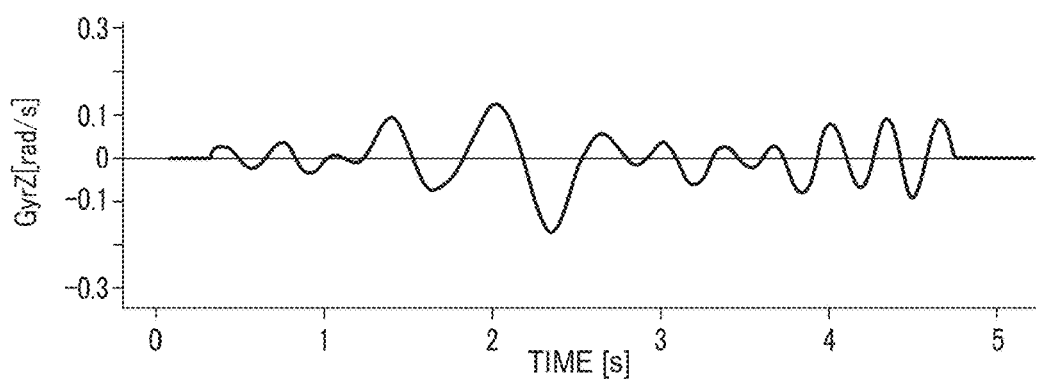

On the contrary, FIG. 11B-1 shows an example of the output GyrZ in the z-axis direction of the gyroscope sensor 22 during seated before correction, and FIG. 11B-2 shows a result of the correction to set the middle position between the local extrema of the output GyrZ in the z-axis direction at 0 (zero). FIG. 11B-2 shows an example of failure, and shows the example where this determines that the output GyrZ in the z-axis direction of the gyroscope sensor 22 has periodicity including the noise, and so fails to determine the action as seated correctly.

After this correction between local extrema, the CPU 11 determines whether the autocorrelation coefficient of the output GyrY in the y-axis direction of the gyroscope sensor 22 is larger than an eleventh threshold Th11, e.g., 0.49 and whether this output GyrY has variance larger than a twelve threshold Th12, e.g., 0.018, or determines whether the autocorrelation coefficient of the output GyrZ in the z-axis direction of the gyroscope sensor 22 is larger than the eleventh threshold Th11 and whether this output GyrZ has variance larger than the twelfth threshold Th12. The CPU 11 makes a determination of at least any one of them (Step S223).

In the determination at Step S223, the eleventh threshold Th11 and the twelfth threshold Th12 are set somewhat large. This is to extract the output GyrY in the y-axis direction and the GyrZ in the z-axis direction of the gyroscope sensor 22 having sufficiently large amplitude and having clear periodicity, which can determine that the action is clearly a seated operation.

When the CPU 11 determines that this condition is satisfied (Yes at S223), the CPU 11 determines that the action is seated (Step S224).

When the CPU 11 determines that the condition at Step S223 is not satisfied (No at Step S223), then the CPU 11 determines whether the autocovariance of the output GyrY in the y-axis direction of the gyroscope sensor 22 is smaller than a thirteenth threshold Th13, e.g., 0.00017 or whether this output GyrY has variance smaller than a fourteenth threshold Th14, 0.002 and determines whether the autocovariance of the output GyrZ in the z-axis direction of the gyroscope sensor 22 is smaller than the thirteenth threshold Th13 and whether this output GyrZ has variance smaller than the fourteenth threshold Th14 (Step S225).

In this determination at Step S225, the output GyrY in the y-axis direction and the output GyrZ in the z-axis direction of the gyroscope sensor 22 having very small amplitude and having clearly low periodicity are extracted, whereby the CPU 11 can identify the case where the action is clearly not seated. To this end, the thirteenth threshold Th13 and the fourteenth threshold Th14 are set somewhat small.

When the CPU 11 determines that this condition is satisfied (Yes at Step S225), the CPU 11 determines that the action is not seated (Step S226).

When the CPU 11 determines that the condition at Step S225 is not satisfied (No at Step S225), then the CPU 11 determines whether the autocovariance of the output GyrY in the y-axis direction of the gyroscope sensor 22 is larger than the value obtained by multiplying the variance of the output GyrY by the gradient a2 of the border line BD in FIG. 9, e.g., 0.5065 and adding the value of contact (intercept) b2, e.g., 0.00041, or determines whether the autocovariance of the output GyrZ in the z-axis direction of the gyroscope sensor 22 is larger than the value obtained by multiplying the variance of the output GyrZ by the gradient a2 of the border line BD in FIG. 9 and adding the value of contact (intercept) b2. The CPU 11 makes a determination of at least one of them (Step S227).

Seated determination is made by linear separation using the border line BD shown in FIG. 9. When the CPU 11 determines that the condition at Step S227 is satisfied (Yes at S227), the CPU 11 determines that the action is seated (Step S228). The determination at Step S227 enables seated determination when the variance is so small that the action is not determined as seated at Steps S223 and S225.

When the CPU 11 determines that the condition at Step S227 is not satisfied (No at Step S227), the CPU 11 determines that the action is not seated (Step S229).

The correction between local extrema at Step S222 equals to the processing to emphasize the noise. Therefore seated determination 2 at S204 should not be performed prior to the seated determination 1 at Step S201. Seated termination 2 is performed after seated determination 1 to determine the action as seated that has not been determined as such in the seated determination 1. If seated termination 2 is performed first, the cadence cannot be calculated correctly as described later. Therefore the CPU 11 performs seated determination 2 after seated determination 1.

After the seated determination 2 in FIG. 10 as stated above, the CPU 11 returns to the processing of FIG. 6. Then the CPU 11 determines whether the seated determination 2 determines the action as seated or not (Step S205).

When the CPU 11 determines that the action is seated (Yes at Step S205), then the CPU 11 determines again that the action is seated (Step S206) and that the reliability of this determination is low. The CPU 11 then does not use the cadence obtained during the cadence determination to calculate a maximum cadence.

When the CPU 11 determines at Step S205 that the action is not seated (No at Step S205), the CPU 11 subsequently executes seated determination 3 (Step S207). In this seated determination 3, the CPU 11 performs the seated determination based on the output AccY in the y-axis direction of the acceleration sensor 21. That is, the seated determination 3 is targeted for a cyclist who is pedaling so slowly that the angular velocity is hardly detected.

Figure 12:
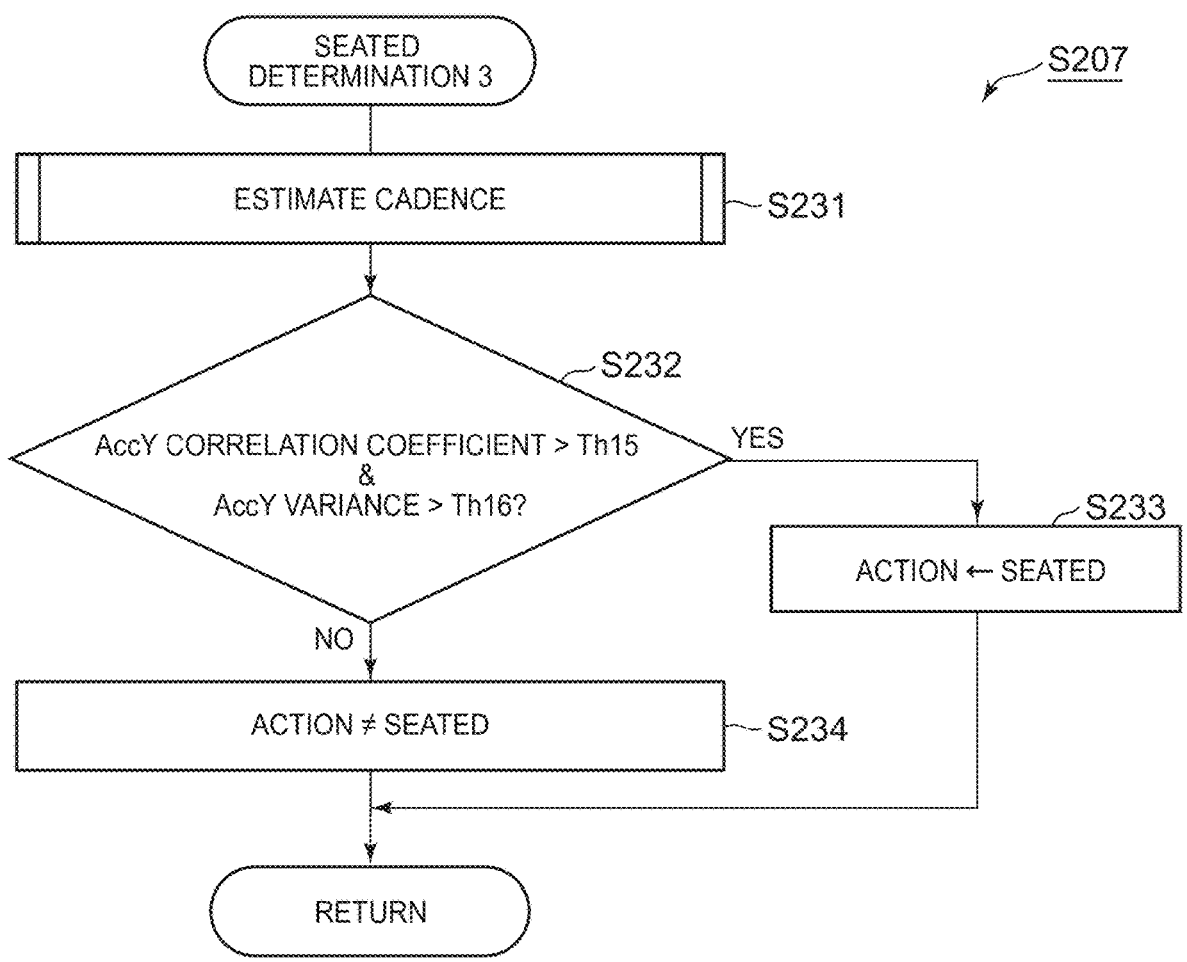
FIG. 12 is a flowchart to show a subroutine of the seated determination 3 (S207) in FIG. 6 in details according to the embodiment.

FIG. 12 is a flowchart to show a subroutine of this seated determination 3 in details. The CPU 11 firstly executes cadence estimation described later (Step S231).

After that the CPU 11 determines whether the autocorrelation coefficient of the output AccY of the acceleration sensor 21 in the y-axis direction is larger than a fifteenth threshold Th15, e.g., 0.65, and whether the output AccY has variance larger than a sixteenth threshold Th16, e.g., 0.071 (Step S232).

When the CPU 11 determines that the condition at Step S232 is satisfied (Yes at S232), the CPU 11 determines that the action is seated (Step S233).

When the CPU 11 determines that the condition at Step S232 is not satisfied (No at Step S232), the CPU 11 determines that the action is not seated (Step S234).

The processing at Step S232 makes a determination as stated above because, even when the outputs GyrY and GyrZ of the gyroscope sensor 22 in the y- and z-axis directions do not have periodicity because of seated having a large gear-value described later and low cadence, for example, the propulsion force during pedaling can be found based on the output AccY of the acceleration sensor 21 in the y-axis direction.

Therefore when the autocorrelation coefficient of the output AccY of the acceleration sensor 21 in the y-axis direction is larger than the fifteenth threshold Th15 and the output AccY has variance larger than the sixteenth threshold Th16, the CPU 11 determines the action as seated.

For instance, if a gear value of a bicycle BC is large and a cyclist CL is pedaling the bicycle BC with their physical ability, seated determinations 1 and 2 may fail to determine it as seated. In that case, seated determination 3 can determine it as seated based on the autocorrelation coefficient and variance of the output AccY of the acceleration sensor 21 in the y-axis direction.

Figure 13A:
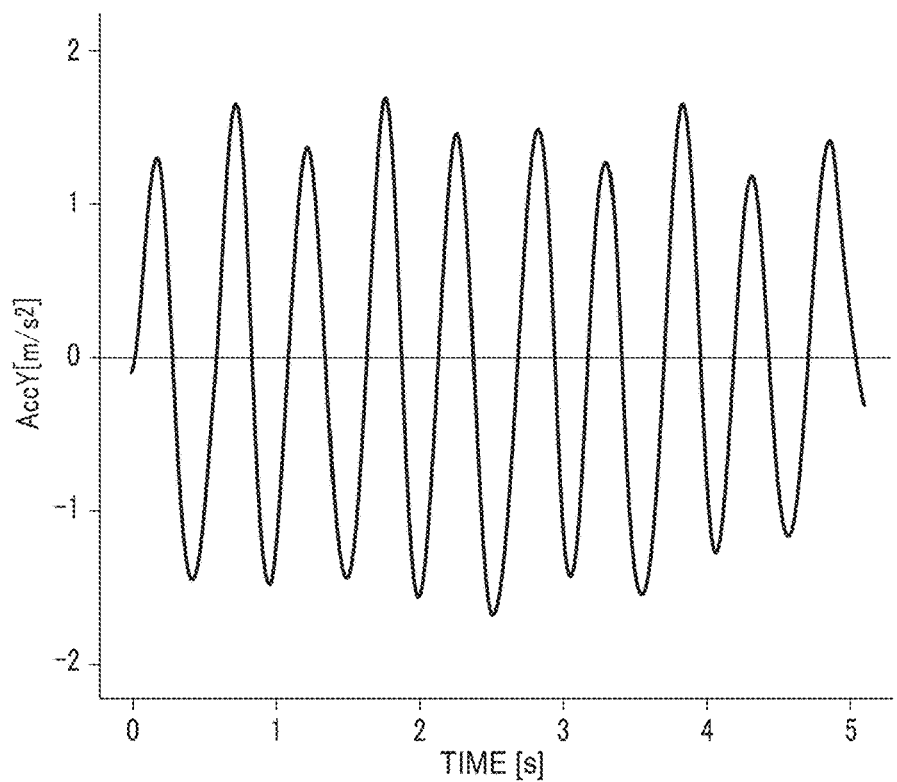
FIGS. 13A and 13B show an example of the detection waveform of the output AccY of the acceleration sensor in the y-axis direction according to the embodiment.
Figure 13B:
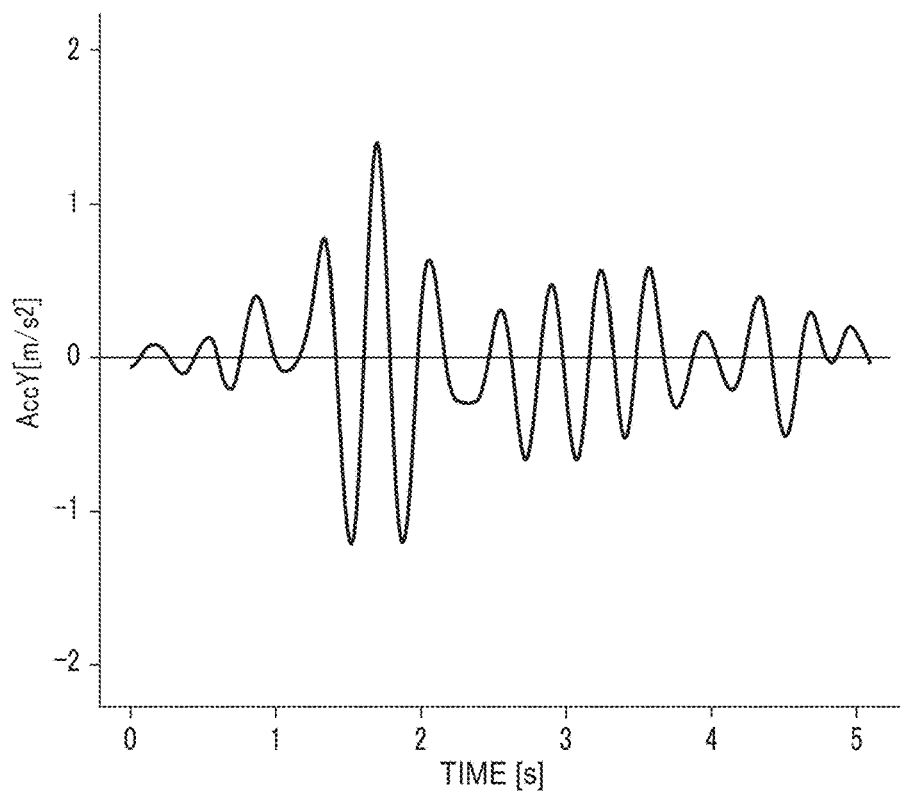

FIGS. 13A and 13B show an example of the detection waveform of the output AccY of the acceleration sensor 21 in the y-axis direction. FIG. 13A shows an example where the periodicity can be successfully detected from the output AccY of the acceleration sensor 21 in the y-axis direction.

On the contrary, FIG. 13B shows an example of a failure where the output AccY of the acceleration sensor 21 in the y-axis direction includes noise overlapped and the periodicity is detected from the waveform including such noise.

When cadence is calculated, which is described later, the CPU 11 calculates the cadence while distinguishing these methods of seated determination. That is, the CPU 11 considers seated determination 1 as a stable detection method for seated and seated determinations 2 and 3 as a slightly instable detection method for seated.

After the seated determination 3 in FIG. 12 as stated above, the CPU 11 returns to the processing of FIG. 6. Then the CPU 11 determines whether the seated determination 3 determines the action as seated or not (Step S208).

When the CPU 11 determines that the action is seated (Yes at Step S208), then the CPU 11 determines again that the action is seated (Step S206) and that the reliability of this determination is low. The CPU 11 then does not use the cadence obtained during the cadence determination to calculate a maximum cadence.

When the CPU 11 determines at Step S208 that the action is not seated (No at Step S208), the CPU 11 determines the action as not seated (Step S209). Then the CPU 11 ends the subroutine in FIG. 6 and returns to the processing of FIG. 5.

After the seated determination at Step S115 in FIG. 5, the CPU 11 determines whether the action is determined as seated or not based on the result of the seated determination (Step S116).

When it is determined that the action is seated (Yes at S116), the CPU 11 determines again that the action is seated (Step S117). After that the CPU 11 executes the processing of cadence setting (2) described later (Step S118) and ends the action determination 3.

When the CPU 11 determines at Step S116 that the action is not seated because the detected data does not have periodicity (No at S116), the CPU 11 determines the action as inertial running (Step S119). Then the CPU 11 ends the action determination 3.

When the CPU 11 determines at Step S112 of the action determination 2 that the speed is not reliable (No at Step S112), the CPU 11 executes action determination 4 at Steps S120 to S126. In this action determination 4, the CPU 11 determines the action as any one of "seated", "inertial running" and "stop". Since information on the travelling speed obtained from the output of the GPS receiver 15 is determined as not reliable in the action determination 2 and the information on the travelling speed estimated from dead reckoning also may not be reliable because of an error or the like, the CPU 11 performs seated determination prior to determination for stop in the action determination 4.

In this action determination 4, the CPU 11 executes seated determination similar to step S115 as stated above prior to determination for stop (Step S120).

After this seated determination, the CPU 11 determines whether the action is determined as seated or not based on the result of the seated determination (Step S121).

When it is determined that the action is seated (Yes at S121), the CPU 11 determines again that the action is seated (Step S122). After that the CPU 11 executes the processing of cadence setting (2) described later (Step S123) and ends the action determination 4.

At this Step S121, when the CPU 11 determines that the action is not seated (No at Step S121), the CPU 11 then determines whether small vibrations on the road surface can be detected or not (Step S124). This determination is made based on whether the derivation of the output AccZ of the acceleration sensor 21 in the z-axis direction has variance larger than a sixth threshold Th6, e.g., 0.19.

When the CPU 11 determines that small vibrations on the road surface can be detected because the derivation of the output AccZ of the acceleration sensor 21 in the z-axis direction has variance larger than the sixth threshold Th6 (Yes at Step S124), the CPU 11 determines that the action is inertial running (Step S125) and ends the action determination 4.

Since information on the travelling speed obtained from the output of the GPS receiver 15 is determined as not reliable in the action determination 2 as stated above, the action determination 4 cannot use the information on the travelling speed. Therefore the CPU 11 cannot make a determination on stop based on the speed as in at Step S113. Then at Step S124, in order to determine the remaining action (inertial running or stop) not based on the speed, the CPU 11 uses the variance of the derivation of the output AccZ of the acceleration sensor 21 in the z-axis direction, i.e., whether small vibrations from the road surface are detected or not.

At Step S124, when the CPU 11 determines that small vibrations from the road surface cannot be detected (No at Step S124) because the derivation of the output AccZ of the acceleration sensor 21 in the z-axis direction has variance of the sixth threshold Th6 or smaller, the CPU 11 determines that the action is stop (Step S126) and ends action determination 4.

Next, the following describes the cadence estimation at Step S102 in FIG. 5, at Step S211 in FIG. 7, at Step S221 in FIG. 10 and at Step S231 in FIG. 12 in details.

Cadence is a value indicating the number of rotations of a crank pedal during pedaling by a cyclist CL with a bicycle BC, and the value changes continually as stated above. Cadence typically is represented in the units [rpm] as the latest number of rotations per minute.

A maximum cadence is a maximum value of the cadence during the entire route, and is typically used as one of the indexes for the ability of cycling.

The integrated number of rotations is the total number of rotations during pedaling along the entire route, which corresponds to the number of steps during walking.

In the present embodiment, when the action is standing, seated or walking, such an action is considered to have periodicity and cadence is calculated therefor.

When the action is inertial running or stop, cadence is not calculated because such an action does not have periodicity.

Figure 14:
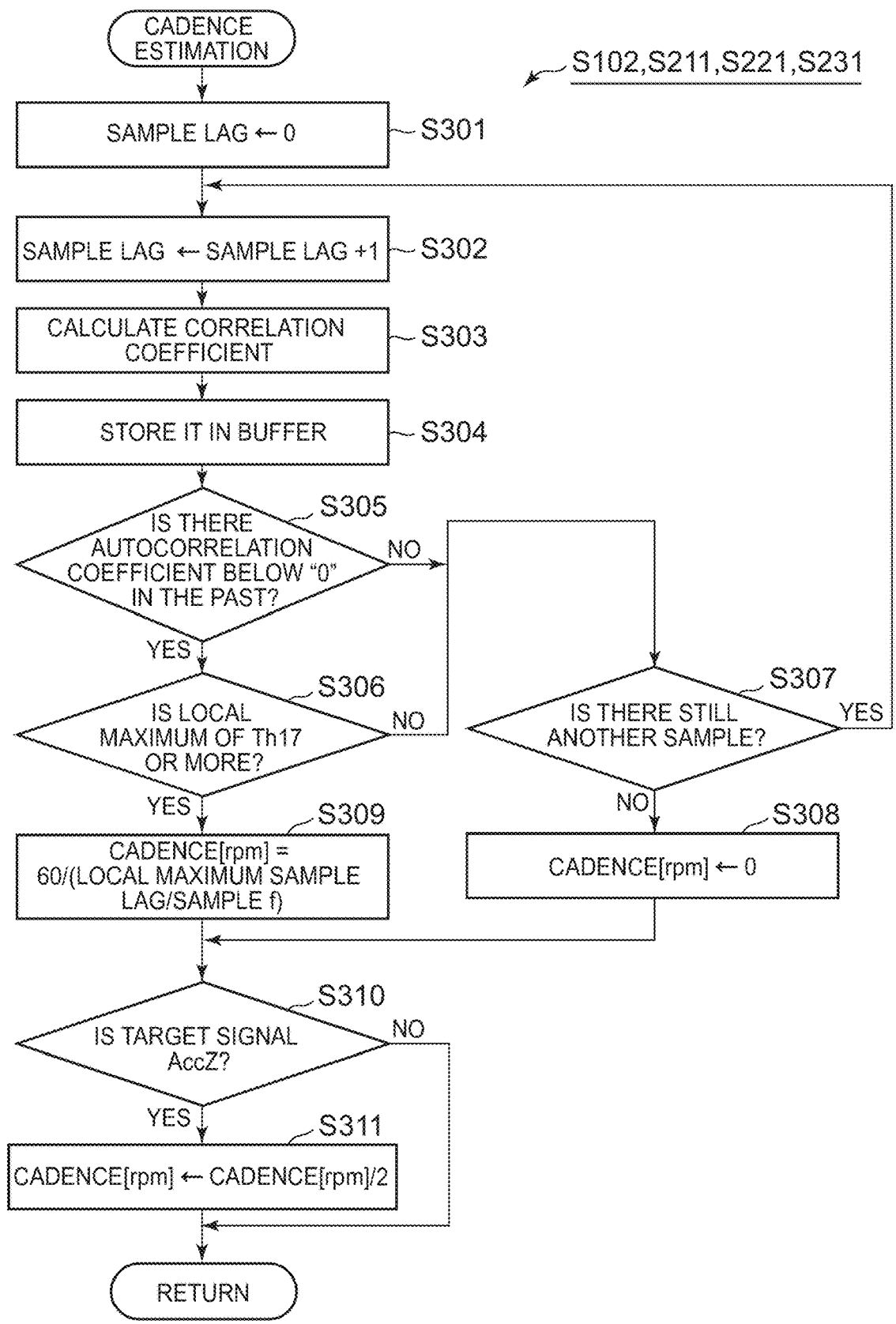
FIG. 14 is a flowchart to show a subroutine of the cadence estimation (S102, S211, S221, S231) in FIG. 5, FIG. 7, FIG. 10 and FIG. 12 in details according to the embodiment.

FIG. 14 is a flowchart of a subroutine of cadence estimation common to these actions. At the beginning, the CPU 11 sets an initial value "0" at a sample lag (Step S301).

Next the CPU 11 updates the value of the sample lag to be "+1" (Step S302). The CPU 11 calculates the autocorrelation coefficient based on the updated sample lag (Step S303), and stores the calculated autocorrelation coefficient in a buffer in the main memory 12 (Step S304).

Next the CPU 11 determines whether there is an autocorrelation coefficient below "0" in the past (Step S305).

When the CPU 11 determines that there is an autocorrelation coefficient below "0" (Yes at Step S305), the CPU 11 next determines whether the value is a local maximum of the seventeenth threshold Th17, e.g., 0.2 or more (Step S306).

When the CPU 11 determines at Step S305 that there is no autocorrelation coefficient below "0" (No at Step S305) and when the CPU 11 determines at Step S306 that the value of the autocorrelation coefficient is smaller than seventeenth threshold Th17 (No at Step S306), then the CPU 11 does not use the autocorrelation coefficient, and determines whether there is still another sample (Step S307).

When the CPU 11 determines that there is still another sample (Yes at Step S307), the CPU 11 returns to the processing from Step S302 as stated above, and repeats a similar operation.

In this way, the CPU 11 updates a sample lag sequentially, and searches for a sample lag having the autocorrelation coefficient that is a local maximum while sequentially scanning from "0".

When the CPU 11 determines at Step S306 that the calculated autocorrelation coefficient is a local maximum of the seventeenth threshold Th17 or more (Yes at Step S306), the CPU 11 divides the sample lag as the local maximum by the sampling frequency (sample f) to obtain a quotient, and further divides the quotient by the constant 60 [sec.] to obtain the cadence value [rpm] (Step S309).

When the CPU 11 determines at Step S307 that there is no more samples (No at Step S307), the CPU 11 sets a fixed value 0 (zero) [rpm] as the cadence value because the cadence cannot be calculated (Step S308).

After obtaining the cadence value at Step S309 or Step S308, the CPU 11 determines whether the action is walking or not (Step S310). This determination is made based on whether the signal as target is the output AccZ of the acceleration sensor 21 in the z-axis direction or not.

Only when the CPU 11 determines that the action is walking because the signal as target is the output AccZ of the acceleration sensor 21 in the z-axis direction (Yes at Step S310), the CPU 11 updates the calculated cadence value [rpm] to be ½ (Step S311) due to matching with the number of rotations of the crank pedal, and ends the cadence estimation.

When the CPU 11 determines at Step S310 that the action is not walking because the signal as target is not the output AccZ of the acceleration sensor 21 in the z-axis direction (No at Step S310), the CPU 11 does not execute the processing at Step S311 and ends the cadence estimation.

At Step S306 as stated above, determination is made based on the seventeenth threshold Th17 about whether the local maximum is to be used or not for the autocorrelation coefficient of a sample lag. This is to remove the influences from the local maxima of high-frequency waves as shown in FIGS. 15A and 15B.

Figure 15A:
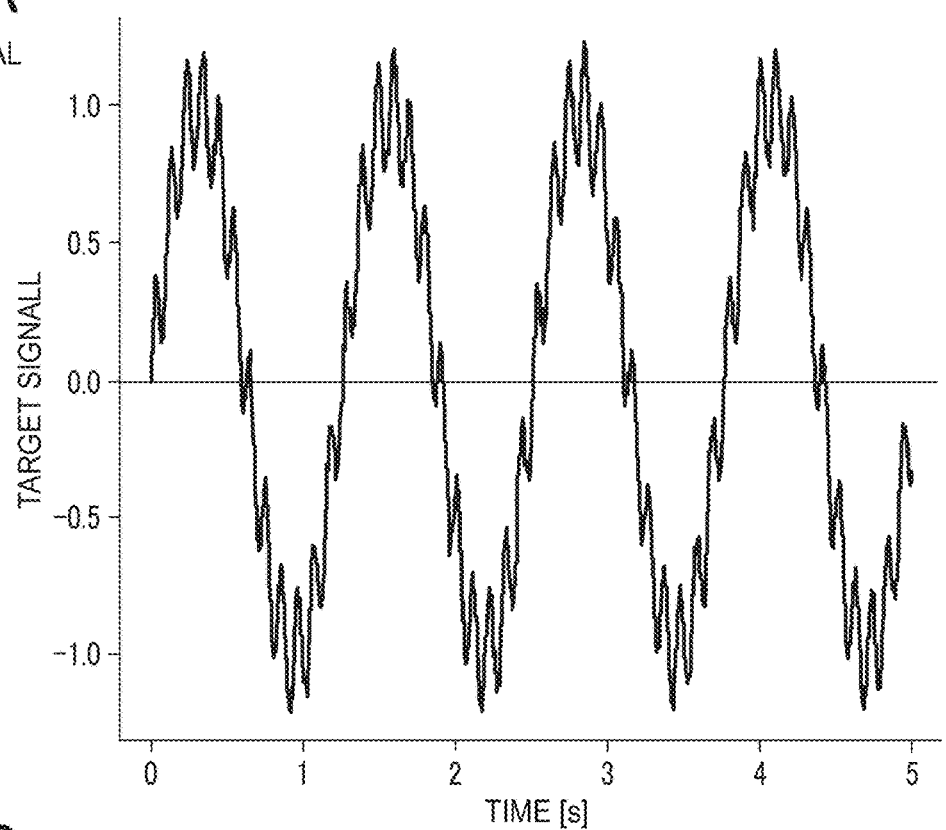
FIGS. 15A and 15B show an example of the local maxima of high-frequency waves due to noise that appears in the autocorrelation coefficient according to the embodiment.
Figure 15B:
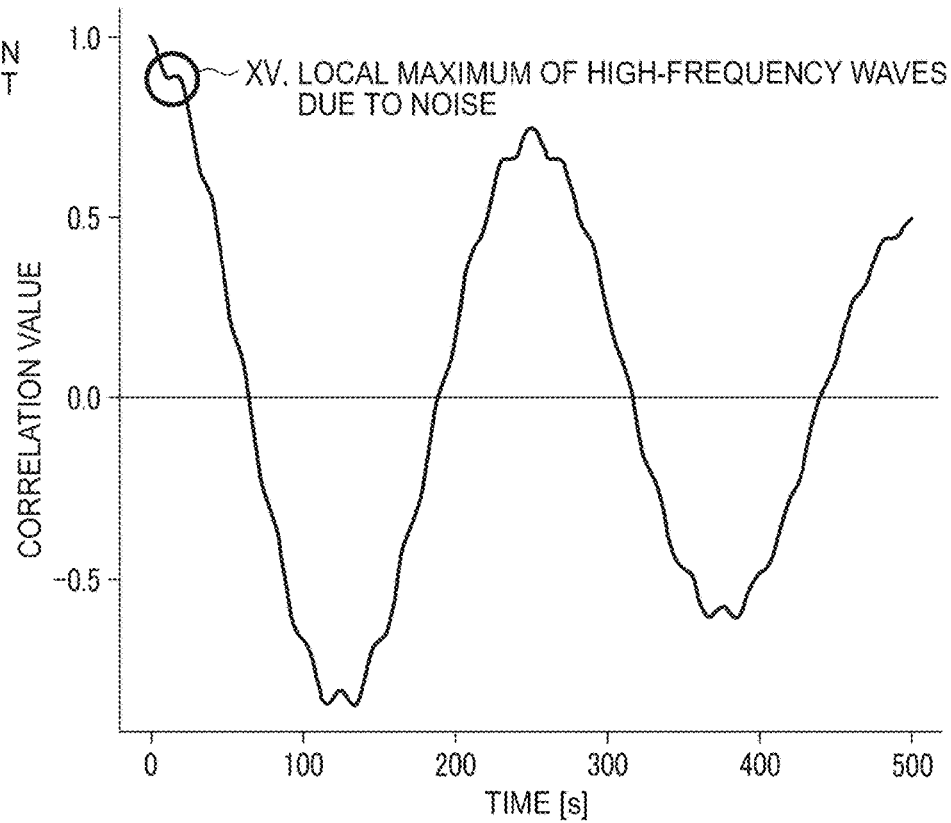

FIG. 15A shows an example of the waveform of an input signal as a target. FIG. 15B shows the result of calculated autocorrelation coefficient from this input signal. As indicated at XV part in FIG. 15B, a local maximum of high-frequency waves due to noise may appear in the waveform. A determination at Step S305 is made not to use such a case.

Next the following describes how to calculate cadence for each action.

For the integrated number of rotations and the maximum cadence, different cadence values are used. This is because the integrated number of rotations does not generate a large error for the final integrated value in total even when it has a small error in estimation at each time. On the contrary, if a large cadence value is output at a certain time, the maximum cadence value cannot be corrected later. Therefore a stable cadence value has to be used for the maximum cadence.

Firstly the following describes how to calculate cadence when the action is walking or standing.

Figure 16:
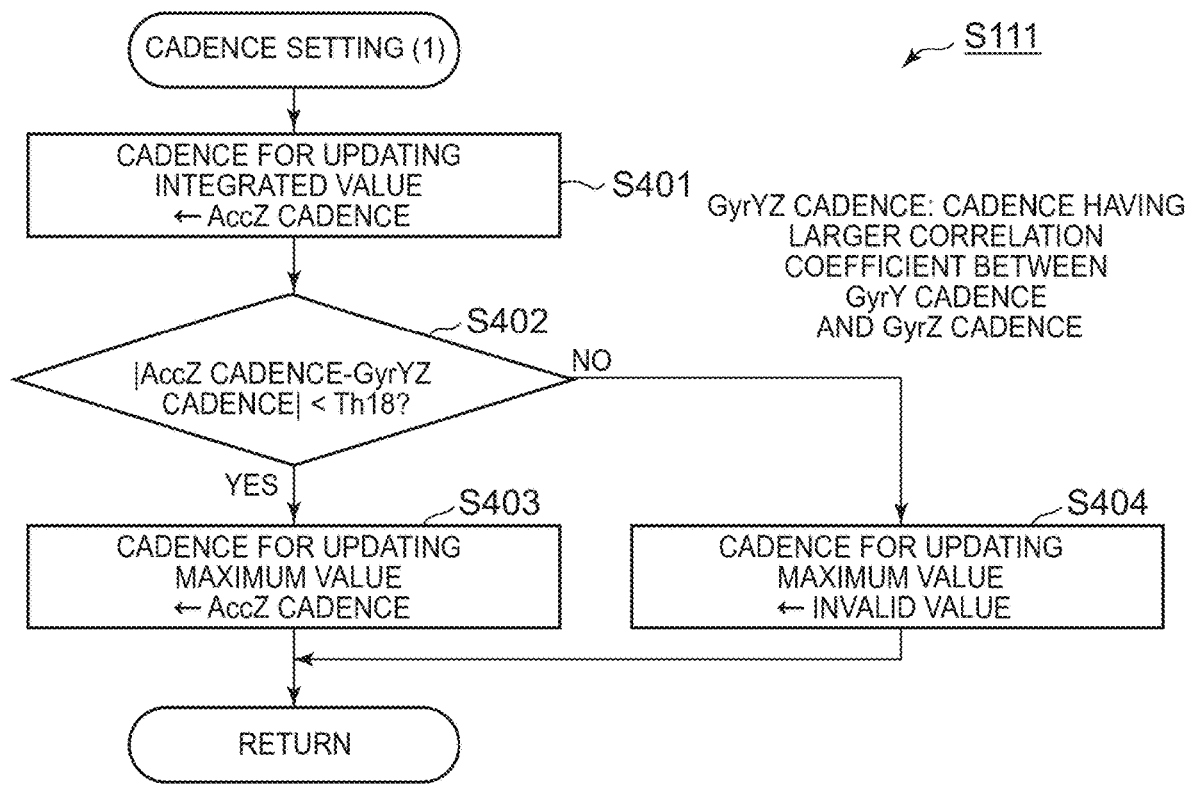
FIG. 16 is a flowchart to show a subroutine to set the first cadence value (cadence setting (1)) (S111) in FIG. 5 in details according to the embodiment.

FIG. 16 is a flowchart of a subroutine to set the first cadence value (cadence setting (1)) at Step S111 in FIG. 5 as stated above in details.

The CPU 11 firstly counts the cycle of the output AccZ of the acceleration sensor 21 in the z-axis direction as the cadence value, and sets this as cadence for updating integrated value (Step S401).

After that, the CPU 11 uses the cadence value GyrYZ having a larger autocorrelation coefficient that is any one of the cadence value based on the output GyrY of the gyroscope sensor 22 in the y-axis direction and the output GyrZ of the gyroscope sensor in the z-axis direction, and determines whether the cadence value of the output AccZ of the acceleration sensor 21 in the z-axis direction is reliable or not (Step S402). This determination is made based on whether an absolute value of the difference of the cadence value GyrYZ from the cadence value of the output AccZ of the acceleration sensor 21 in the z-axis direction is smaller than an eighteenth threshold Th18, e.g., 10 or not.

When the CPU 11 determines that the absolute value of the difference of the cadence value GyrYZ from the cadence value of the output AccZ is smaller than the eighteenth threshold Th18, and so the cadence value of the output AccZ of the acceleration sensor 21 in the z-axis direction is reliable (Yes at Step S402), the CPU 11 uses the cadence value of the output AccZ of the acceleration sensor 21 in the z-axis direction as the cadence for updating maximum value (Step S403). Then the CPU 11 ends setting of the first cadence value.

When the CPU 11 determines at Step S402 that the absolute value of the difference of the cadence value GyrYZ from the cadence value of the output AccZ is the eighteenth threshold Th18 or larger, and so the cadence value of the output AccZ of the acceleration sensor 21 in the z-axis direction is not reliable (No at Step S402), the CPU 11 uses an invalid value as the cadence for updating maximum value (Step S404). Then the CPU 11 ends setting of the first cadence value.

Such a comparison between the absolute value of the difference of the cadence value GyrYZ from the cadence value of the output AccZ and the eighteenth threshold Th18 is to remove counting of an extremely large cadence value due to noise, which may appear when the action is walking or standing. When the absolute value of the difference between these two cadence value is the threshold Th18 or smaller and so these values are substantially similar cadence values, the CPU 11 determines that the cadence value is highly reliable.

Next the following describes how to calculate cadence when the action is seated.

Figure 17:
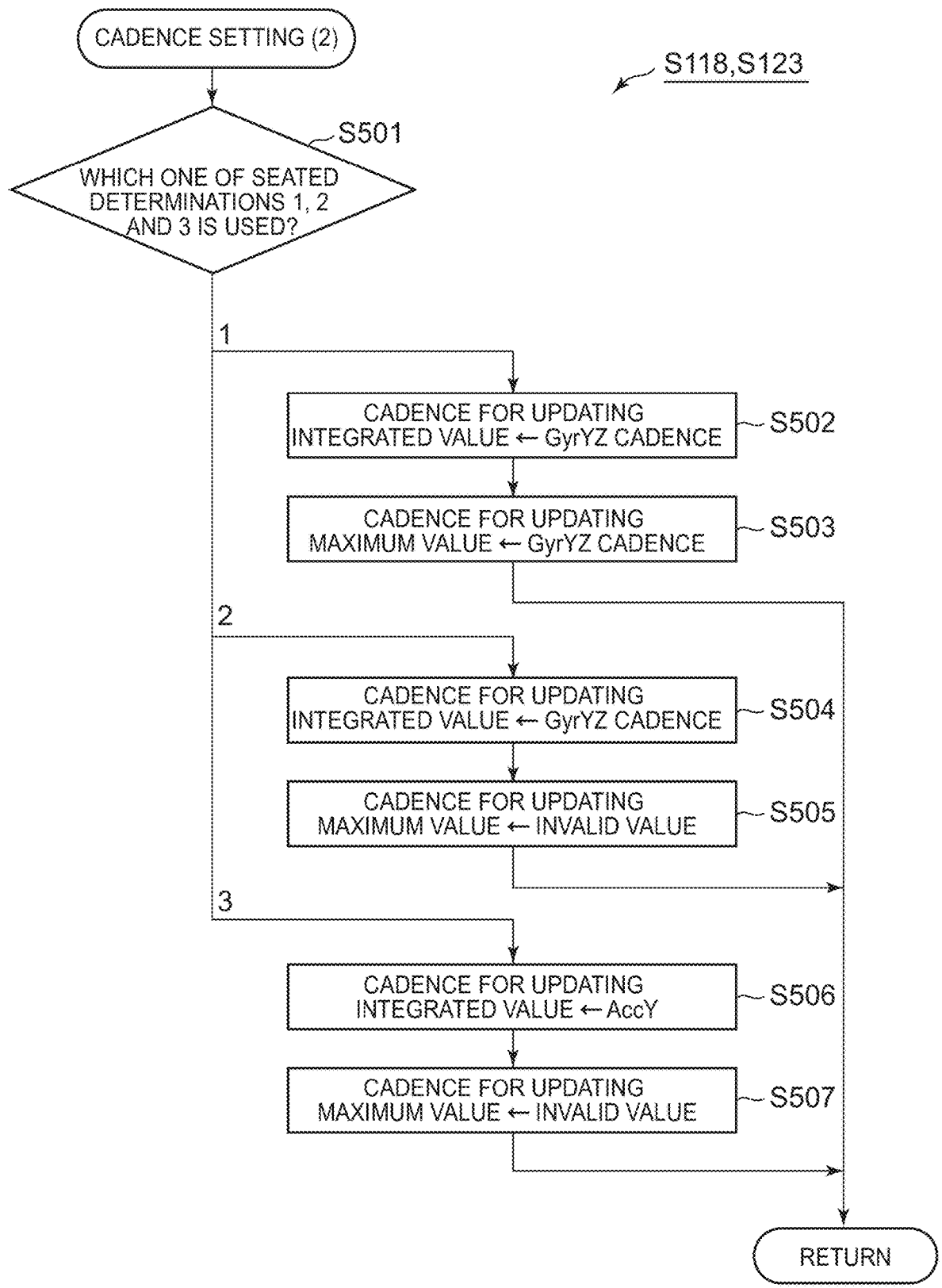
FIG. 17 is a flowchart to show a subroutine to set the second cadence value (S118, S123) in FIG. 5 in details according to the embodiment.

FIG. 17 is a flowchart of a subroutine to set the second cadence value (cadence setting (2)) at Steps S118 and S123 in FIG. 5 as stated above in details.

At the beginning of this processing, the CPU 11 determines which one of seated determination 1, seated determination 2, and seated determination 3 in FIG. 6 is used for determination of seated (Step S501).

When the CPU 11 determines that seated determination 1 is used, the CPU 11 sets the cadence value obtained by counting the cycle of the output GyrYZ of the gyroscope sensor 22 in the y-axis or z-axis direction as the cadence value for updating integrated value (Step S502) because the output GyrY, GyrZ is reliable and stable.

The CPU 11 then sets the cadence value GyrYZ as the cadence value for updating maximum value (Step S503), and ends the processing of FIG. 17.

When the CPU 11 determines at Step S501 that seated determination 2 is used, the CPU 11 sets, based on the output GyrY, GyrZ subjected to correction of local extrema, the cadence value GyrYZ as the cadence value for updating integrated value (Step S504).

The CPU 11 then sets an invalid value as the cadence value for updating maximum value (Step S505), and ends the processing of FIG. 17.

This is because, as shown in FIG. 11B-1 and FIG. 11B-2, the correction of local extrema may emphasize noise, which leads to the risk of generating high-frequency waves.

When the CPU 11 determines at Step S501 that seated determination 3 is used, this is the case where the action is determined as seated based on the output AccY of the acceleration sensor 21 in the y-axis direction. The CPU 11 therefore sets the cadence value obtained by counting the cycle of the output AccY as the cadence value for updating integrated value (Step S506).

The CPU 11 then sets an invalid value as the cadence value for updating maximum value (Step S507), and ends the processing of FIG. 17.

This is because, as shown in FIG. 13B, a signal of the output AccY tends to include a lot of noise, which leads to the risk of generating high-frequency waves.

In this way, stable periodicity is determined first, and then somewhat instable periodicity is determined later. Thereby stable cadence and less stable cadence can be clearly separated in the processing.

In FIG. 5 as stated above, after executing the processing of action determination 1 to action determination 4, the CPU 11 executes updating of the cadence (Step S127).

Figure 18:
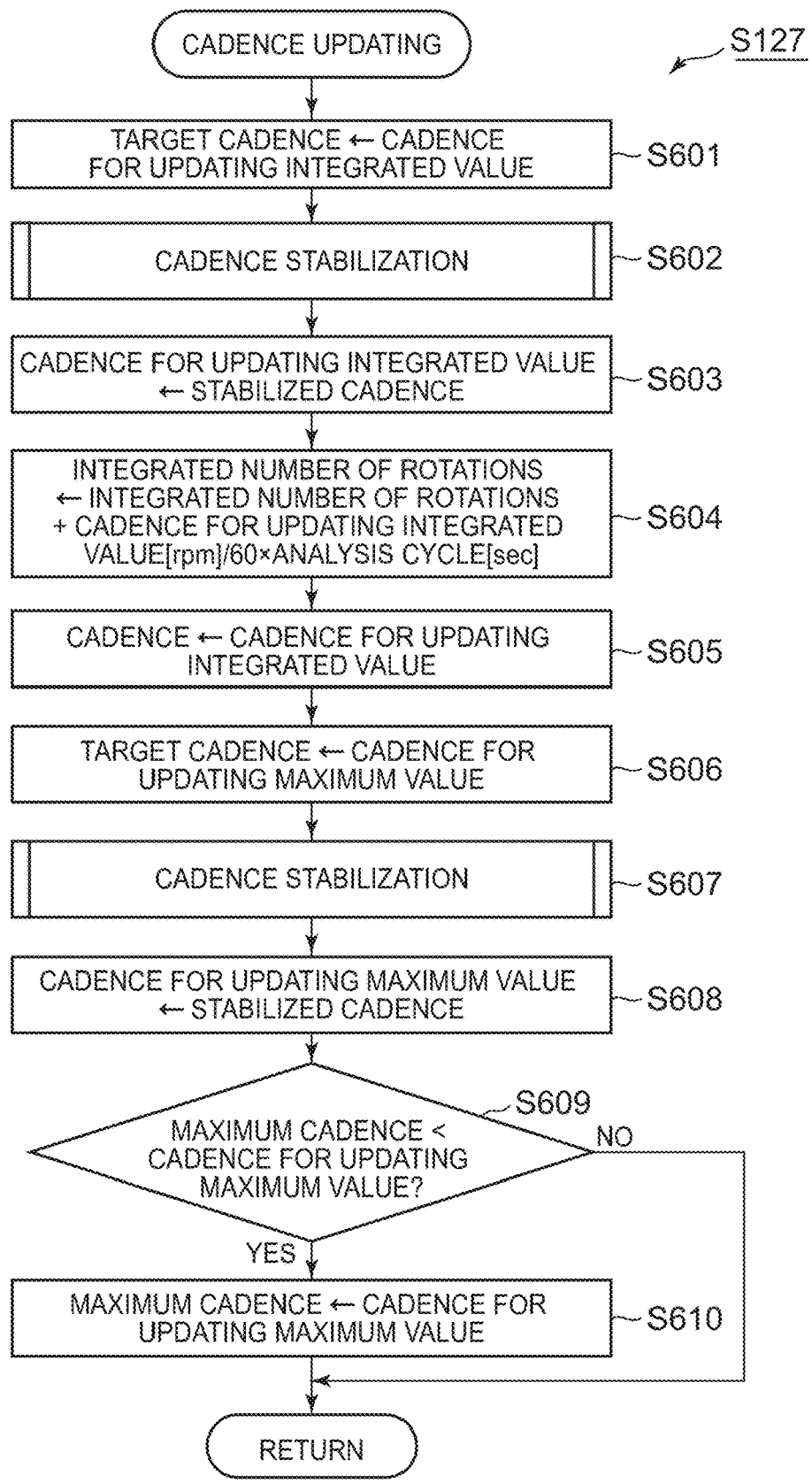
FIG. 18 is a flowchart to show a subroutine to update the cadence value (cadence setting (2)) (S127) in FIG. 5 in details according to the embodiment.

FIG. 18 is a flowchart to show a subroutine of the updating of cadence as stated above in details.

The CPU 11 firstly sets a value of the cadence for updating integrated value at that time as target cadence (Step S601), and stabilizes the cadence (Step S602).

Figure 19:
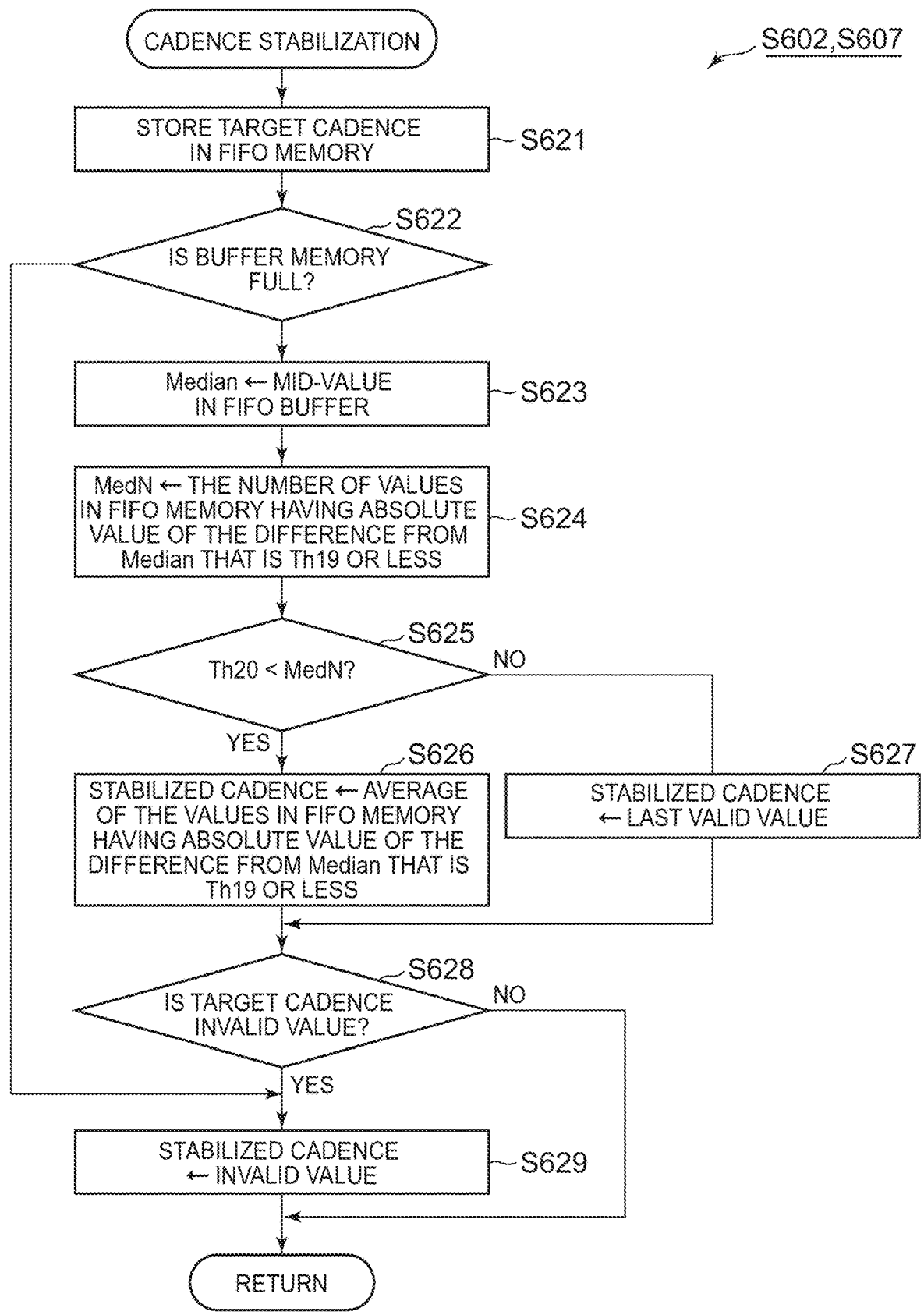
FIG. 19 is a flowchart to show a subroutine to stabilize cadence (S602) in FIG. 18 in details according to the embodiment.

FIG. 19 is a flowchart to show a subroutine of the stabilizing of cadence as stated above in details.

The CPU 11 firstly stores the target cadence in a buffer memory as a FIFO memory configured in the main memory 12 (Step S621). The buffer memory has a capacity corresponding to five values of cadence, for example.

The CPU 11 determines whether the buffer memory is completely full or not (Step S622). When the CPU 11 determines that the memory is not full (No at Step S622), the CPU 11 holds or sets an invalid value as stabilizing cadence value in the buffer memory (Step S629), and ends the processing of FIG. 19. For setting of such an invalid value, the following processing counts an invalid value as data also when the buffer memory holds the invalid value.

When the CPU 11 determines at Step S622 that the memory is full, including an invalid value (Yes at Step S622), the CPU 11 selects a mid-value of the five cadence values, for example, that are held in the buffer memory and sets this as variable Median (Step S623).

Next the CPU 11 obtains the number of cadence values in the buffer memory whose absolute value of the difference from the variable Median is a nineteenth threshold Th19, e.g., 20 or less, and sets this as variable MedN (Step S624).

The CPU 11 determines whether the stability of the cadence values stored in the buffer memory is high or not (Step S625). This determination is made based on whether the number of the cadence values set as this MedN is larger than a twentieth threshold TH20, e.g., 3 or not.

When the CPU 11 determines that the stability of the cadence values stored in the buffer memory is high because the number of the cadence values set as this Med-N is larger than the twentieth threshold TH20 (Yes at Step S625), the CPU 11 calculates the average of the cadence values whose absolute value of the difference from the variable Median is the nineteenth threshold TH19 or less based on the contents stored in the buffer memory, and newly sets the calculated average of the cadence values as a stabilized cadence value (Step S626).

When the CPU 11 determines at Step S625 that the stability of the cadence values stored in the buffer memory is not so high because the number of the cadence values set as this MedN is the twentieth threshold TH20 or less (No at Step S625), the CPU 11 reads out a last-held cadence value among the cadence values whose absolute value of the difference from the variable Median is the nineteenth threshold TH19 or less from the contents stored in the buffer memory, and sets the read-out cadence value as a stabilized cadence value (Step S627).

After the processing at Step S626 or Step S627, the CPU 11 determines whether the cadence value as a target is an invalid value or not (Step S628).

Only when the CPU 11 determines that the cadence value as a target, the value of cadence for updating integrated value in this case, is an invalid value (Yes at Step S628), the CPU 11 sets an invalid value as a stabilizing cadence value (Step S629). Then the CPU 11 ends the processing of FIG. 19, and returns to the processing in FIG. 18 as stated above.

When the CPU 11 determines at Step S628 that the cadence value as a target, the value of cadence for updating integrated value in this case, is not an invalid value, the CPU 11 does not execute the processing at Step S629.

In this way, when the cadence value as a target is an invalid value, the buffer memory may hold another valid cadence value. In that case, such a valid cadence value may be set as a stabilized cadence value. To avoid this, when the cadence value as a target is an invalid value, the CPU 11 sets an invalid value as the stabilized cadence value similarly in the final processing.

In FIG. 18, the CPU 11 sets the stabilized cadence value set at Step S602 as cadence for updating integrated value (Step S603).

After that, the CPU 11 divides the stabilized cadence value for updating integrated value by 60, multiplies this by the analysis cycle, and adds the integrated number of rotations last time to this. The CPU 11 sets such a calculated value as the integrated number of rotations (Step S604).

After that, the CPU 11 sets the value of cadence for updating integrated value as the current cadence value (Step S605).

Then the CPU 11 ends the updating of cadence for updating integrated value. Next, the CPU 11 sets the value of cadence for updating maximum value as a target cadence (Step S606) and stabilizes the cadence (Step S607).

Since this stabilizing of cadence (Step S607) is similar to FIG. 19 executed at Step S602, their detailed description is omitted.

In this case, since cadence for updating maximum value is a target, 20 is used, for example, for the nineteenth threshold TH19, and 4 is used, for example, for the twentieth threshold TH20.

The CPU 11 sets the stabilized cadence value set at Step S607 as cadence for updating maximum value (Step S608).

After that, the CPU 11 determines whether the cadence for updating maximum value set at the preceding Step S608 is larger than the maximum cadence before that or not (Step S609).

Only when the CPU 11 determines that the cadence for updating maximum value is the maximum cadence in the past (Yes at Step S609), the CPU 11 updates the maximum cadence with the value of the cadence for updating maximum value (Step S610). Then the CPU 11 ends the processing of FIG. 18 as well as the processing of FIG. 5, and returns to the main routine of FIG. 3 as stated above.

When the CPU 11 determines at Step S609 that the cadence for updating maximum value is the maximum cadence in the past or less (No at Step S609), the CPU 11 considers that updating of the maximum cadence is not necessary, and so does not execute Step S610 as stated above.

Returning to the main routine of FIG. 3, the CPU 11 next estimates the gradient (Step M106). The CPU 11 calculates the current gradient in a unit distance from a variation of the altitude information that varies per the latest 30 [m] in the past, for example. When a result of the calculation is positive, the CPU 11 defines it as an ascending slope. When the result is negative, the CPU 11 defines it as a descending slope.

For the variation of the altitude information used to know the gradient, when the GPS positioning information acquired at the GPS receiver 15 is determined reliable, such GPS positioning information may be used. When the GPS positioning information is determined not reliable, the detection output of the pneumatic sensor 24 may be used.

After this gradient estimation, the CPU 11 estimates the track of the travelling before that (Step M107).

Figure 20:
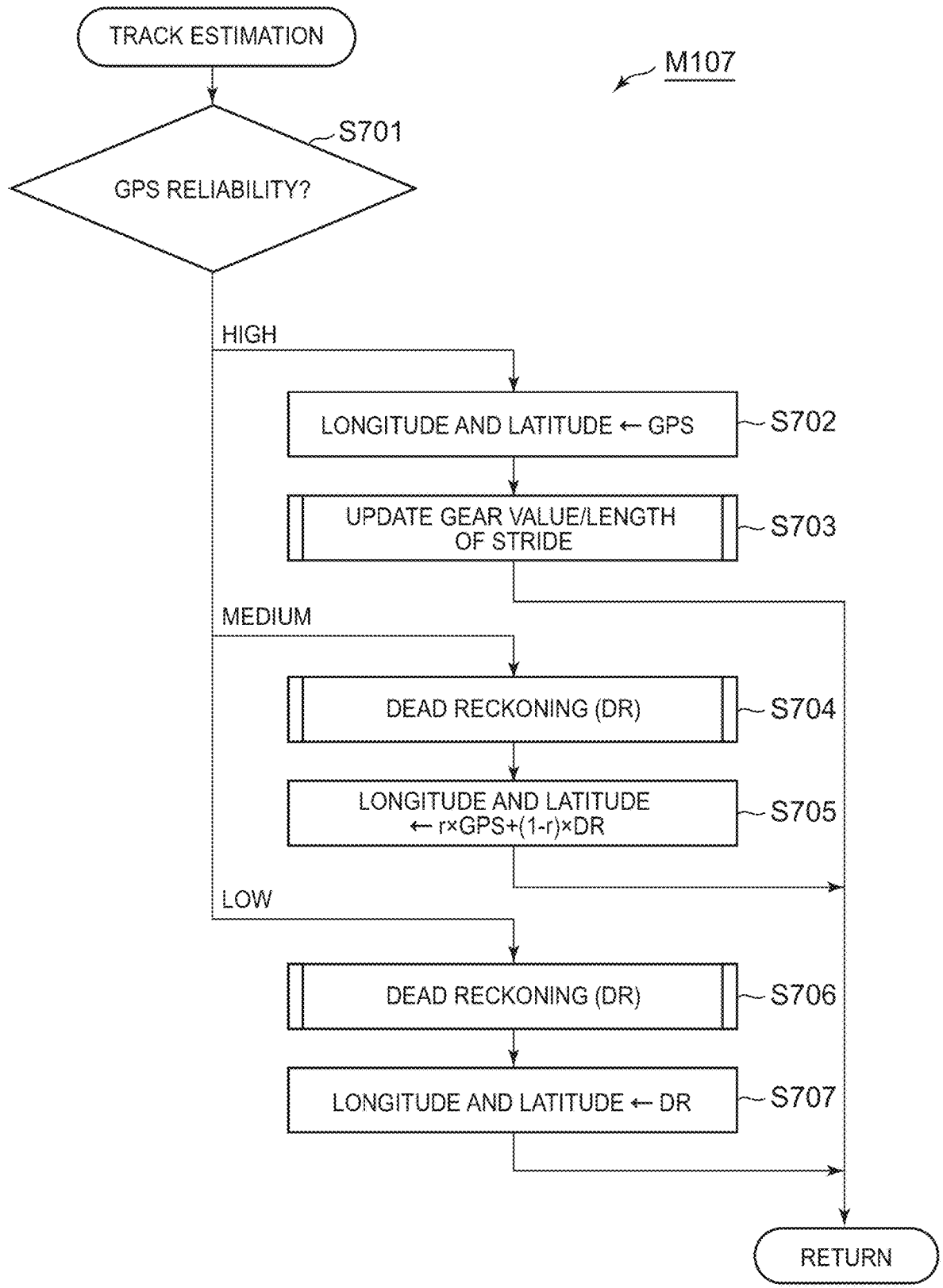
FIG. 20 is a flowchart to show a subroutine of track estimation (M107) in FIG. 3 in details according to the embodiment.

FIG. 20 is a flowchart to show a subroutine of the track estimation at Step M107 as stated above in details.

Firstly the CPU 11 determines the reliability of the GPS positioning information obtained from the GPS receiver 15 at that time with three levels of "high", "medium" and "low" (Step S701).

The CPU 11 determines the reliability of GPS positioning information based on a value of DOP (Dilution Of Precision) indicating the precision lowering rate of the GPS, which can be acquired during the positioning, for example. For instance, when the DOP value is relatively small, the CPU 11 determines that the reliability of GPS positioning information is high. When the DOP value is at a medium level, the CPU 11 determines that the reliability of GPS positioning information is at a medium level. When the DOP value is relatively large, the CPU 11 determines that the reliability of GPS positioning information is low.

When the CPU 11 determines at Step S701 that the GPS positioning information is reliable, the CPU 11 uses such GPS positioning information to set the longitude and latitude of the current position (Step S702).

The CPU 11 then updates the gear value of the bicycle BC used at that time (when the action is seated or standing) or the length of stride (when the action is walking) (Step S703). Such a gear value and a length of stride are used for the dead reckoning described later. This updating of gear value/length of stride is executed only when the GPS positioning information is reliable.

The gear value indicates the distance of the bicycle BC travelling during one rotation of the crank pedal, and varies every time the cyclist CL changes gears.

In order to associate the length of stride with the gear value, the length of stride is set as the distance of the cyclist CL travelling with two steps. This also varies with the degree of fatigue of the cyclist CL or other situations.

Figure 21:
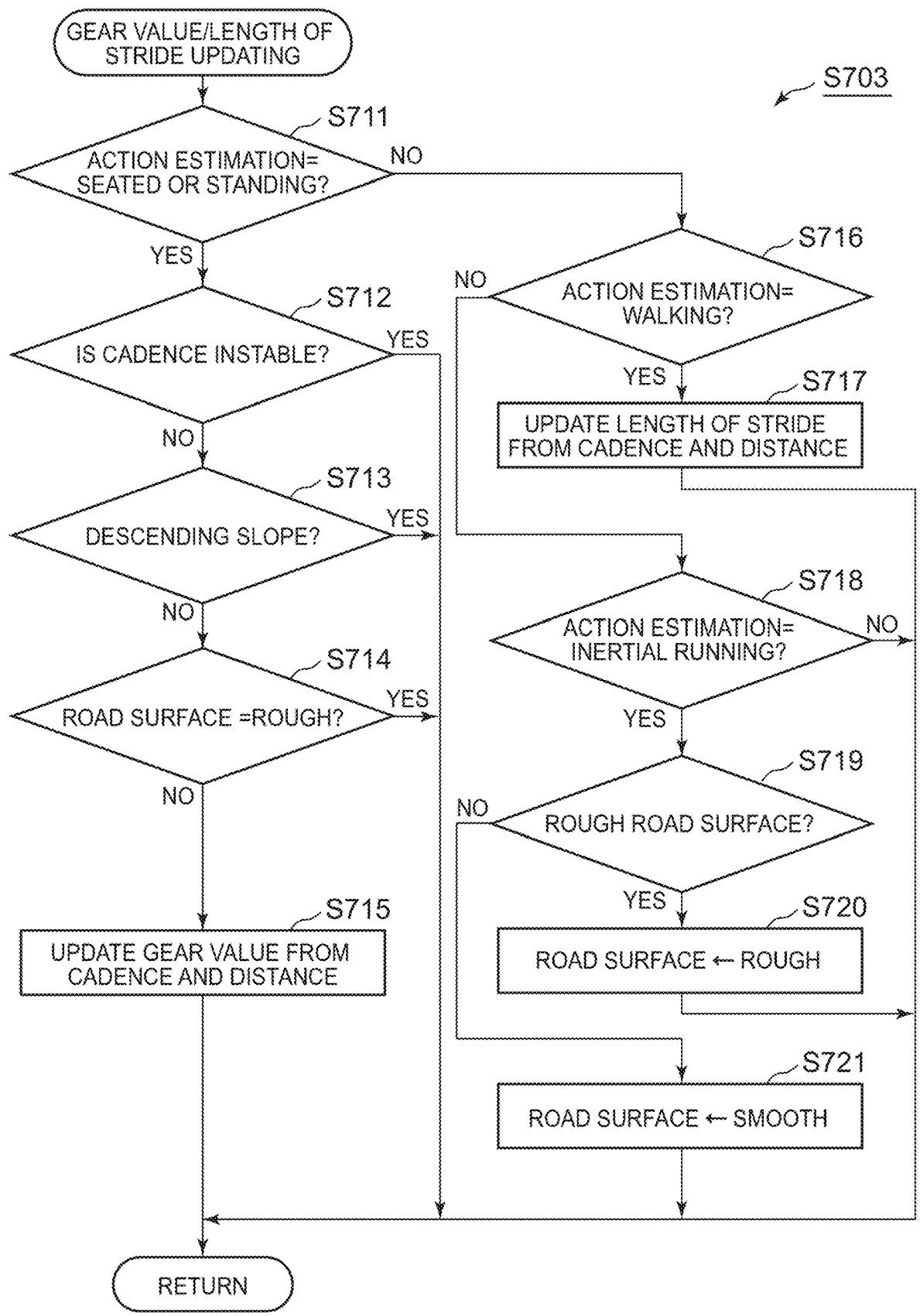
FIG. 21 is a flowchart to show a subroutine to update gear value/length of strider (S703) in FIG. 20 in details according to the embodiment.

FIG. 21 is a flowchart to show a subroutine of this updating of gear value/length of stride in details.

Firstly the CPU 11 determines whether the action estimated is seated or standing. Based on this determination, the CPU 11 determines whether the target of updating is a gear value or not (Step S711).

When the CPU 11 determines that the action estimated is seated or standing and so the target of updating is a gear value (Yes at Step S711), the CPU 11 makes a plurality of determinations on the factor to disturb the proportional relationship between the travelling distance in the travelling direction and the cadence, whereby the gear value is to be updated or not.

Specifically for a first determination, the CPU 11 determines whether the cadence is instable or not (Step S712). This is to remove the case where idle pedaling of the crank pedal (the rotation of the pedal is not transferred to the gear) occurs during the gear changing or immediately after the gear changing.

When a difference in cadence between the last time and this time is 2 [rpm] or more as the criterion for determination, the CPU 11 determines that the cadence is instable (Yes at Step S712), and does not update the gear value. In this way, when the CPU 11 determines that cadence is instable, the CPU 11 does not update a gear value, and ends the processing of FIG. 21. On the contrary, when the CPU 11 determines that cadence is not instable, i.e., stable (No at Step S712), the procedure shifts to Step S713.

For a second determination, the CPU 11 determines whether the slope is a descending slope with a certain angle or more based on the result of gradient estimation obtained at the immediately preceding Step M106 (Step S713). This also is to remove the idle pedaling as stated above. When the slope is a descending slope and has an angle of −3[%] or lower (in numerical value), for example, as the criterion for determination (Yes at Step S713), the CPU 11 does not update the gear value. In this way, when the CPU 11 determines that slope is a descending slope, the CPU 11 does not update a gear value, and ends the processing of FIG. 21. On the contrary, when the CPU 11 determines that the slope is not a descending slope (No at Step S713), the procedure shifts to Step S714.

For a third determination, the CPU 11 determines whether the road is rough or not (Step S714). This is to remove, when the road is rough as in an unpaved road that is determined during the immediately preceding inertial running, the gear state of idle pedaling because the tires are floating and to remove subtle meandering to the left and right or upward of the bicycle BC, which is not calculated as the distance to travel in the travelling direction. When the CPU 11 determines that the road is rough during the preceding inertial running as the criterion for determination (Yes at Step S714), the CPU 11 does not update the gear value. In this way, when the CPU 11 determines that road is rough, the CPU 11 does not update a gear value, and ends the processing of FIG. 21. The determination of the road state is described later in details.

When the CPU 11 determines at Step S714 that the road is not rough but smooth (No at Step S714), the CPU 11 updates the gear value using the cadence and the distance by the following expression (Step S715) because the above three criteria for determination are satisfied:

gear value [m/rev]=distance [m]/(cadence [rpm]/60).

Then the CPU 11 ends the processing of FIG. 21 as well as the processing of FIG. 20.

In this way, when the result of action estimation shows seated or standing (Yes at Step S711), the CPU 11 determines whether the gear value is to be updated or not based on the determinations of the cadence stability (Step S712), the gradient of the path immediately before (Step S713) and the road roughness (Step S714). That is, only when this is not the situation corresponding to the determination criteria at these three steps, the CPU 11 updates the gear value by the above expression.

When the CPU 11 determines at Step S711 that the action estimated is neither seated nor standing (No at S711), the CPU 11 subsequently determines whether the action estimated shows walking or not (Step S716).

When the CPU 11 determines that the action estimated is walking (Yes at Step S716), the CPU 11 updates the length of stride by the following expression because the updated target is not a gear value but a length of stride (Step S717):

length of stride [m/two steps]=distance [m]/(cadence [two steps/min.]/60).

Then the CPU 11 ends the processing of FIG. 21 as well as the processing of FIG. 20.

In the above expression, since one rotation of the crank pedal of a bicycle BC corresponds to two steps of the walking in terms of the period of the motion, the unit of cadence is converted from [rpm] (revolutions per minute) to [two steps/min.].

When the CPU 11 determines at Step S716 that the action estimated is not walking (No at S716), the CPU 11 subsequently determines whether the action estimated shows inertial running or not (Step S718).

When the CPU 11 determines that the action estimated is inertial running (Yes at Step S718), the CPU 11 determines the road state that is used for determination of updating of a gear value as stated above. To this end, the CPU 11 determines whether the road is rough or not based on variance of acceleration triaxial norm obtained by removing the component of gravity acceleration from the output of the acceleration sensor 21 (Step S719).

This is because vibrations corresponding to the road state appear in the information on acceleration during inertial running where the cyclist CL is not pedaling.

Figure 22A:
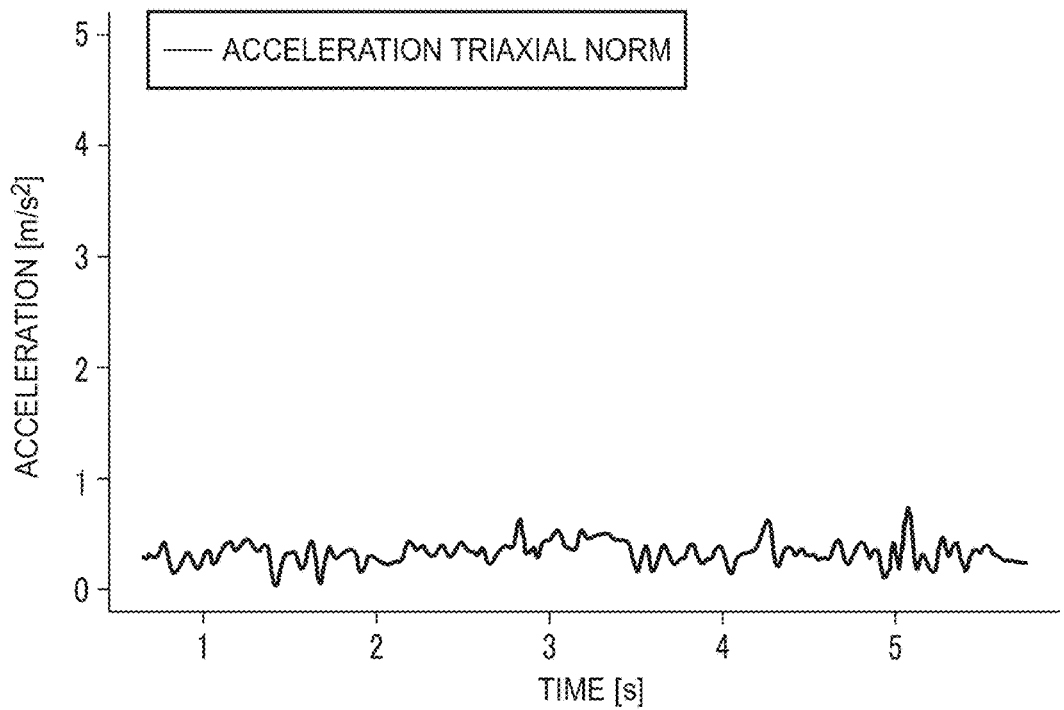
FIGS. 22A and 22B show an example of the waveform of acceleration depending on the road-surface state according to the embodiment.
Figure 22B:
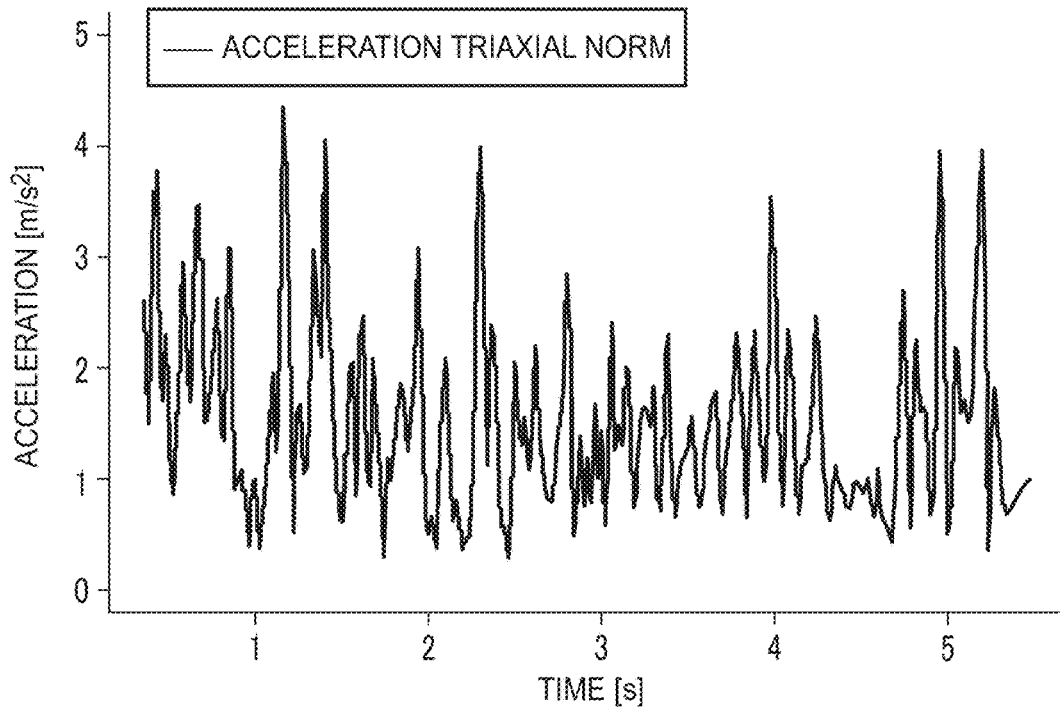

In FIGS. 22A and 22B, FIG. 22A shows the acceleration during inertial running on a smoothly paved road surface, and FIG. 22B shows the acceleration during inertial running on a rough road surface. As shown in this drawing, during inertial running on a smoothly paved road surface, temporal variation of the acceleration triaxial norm is relatively small. On the contrary, during inertial running on a rough road surface, temporal variation of the acceleration triaxial norm is relatively large because of influences from the vibrations from the road surface. Determination of the variance of the acceleration norm about the roughness depends on the precision and the responsiveness of the gear-value updating as stated above. For instance, when the variance is 0.7 or more, the road surface may be determined as rough.

Therefore when the CPU 11 determines the road surface as rough (Yes at Step S719), the CPU 11 sets a flag indicating rough in the flag register in the main memory 12 to show the road state (Step S720). Then the CPU 11 ends the processing of FIG. 21 as well as the processing of FIG. 20.

When the CPU 11 determines at Step S719 that the road surface is not rough (No at Step S719), the CPU 11 sets a flag indicating smooth in the flag register in the main memory 12 to show the road state (Step S721). Then the CPU 11 ends the processing of FIG. 21 as well as the processing of FIG. 20.

In this way, when the CPU 11 determines that the action estimated is inertial running (Yes at Step S718), the CPU 11 does not update both of the gear value and the length of stride, but sets a flag indicating roughness/smoothness of the road state.

When the CPU 11 determines at Step S718 that the action estimated is not inertial running (No at Step S718), the CPU 11 does not update both of the gear value and the length of stride, and ends the processing of FIG. 21 as well as the processing of FIG. 20. This is the case where the result of action estimation is stop.

When the CPU 11 determines at Step S701 of FIG. 20 that the reliability of GPS positioning information is medium, the CPU 11 firstly executes dead reckoning (Step S704).

Figure 23:
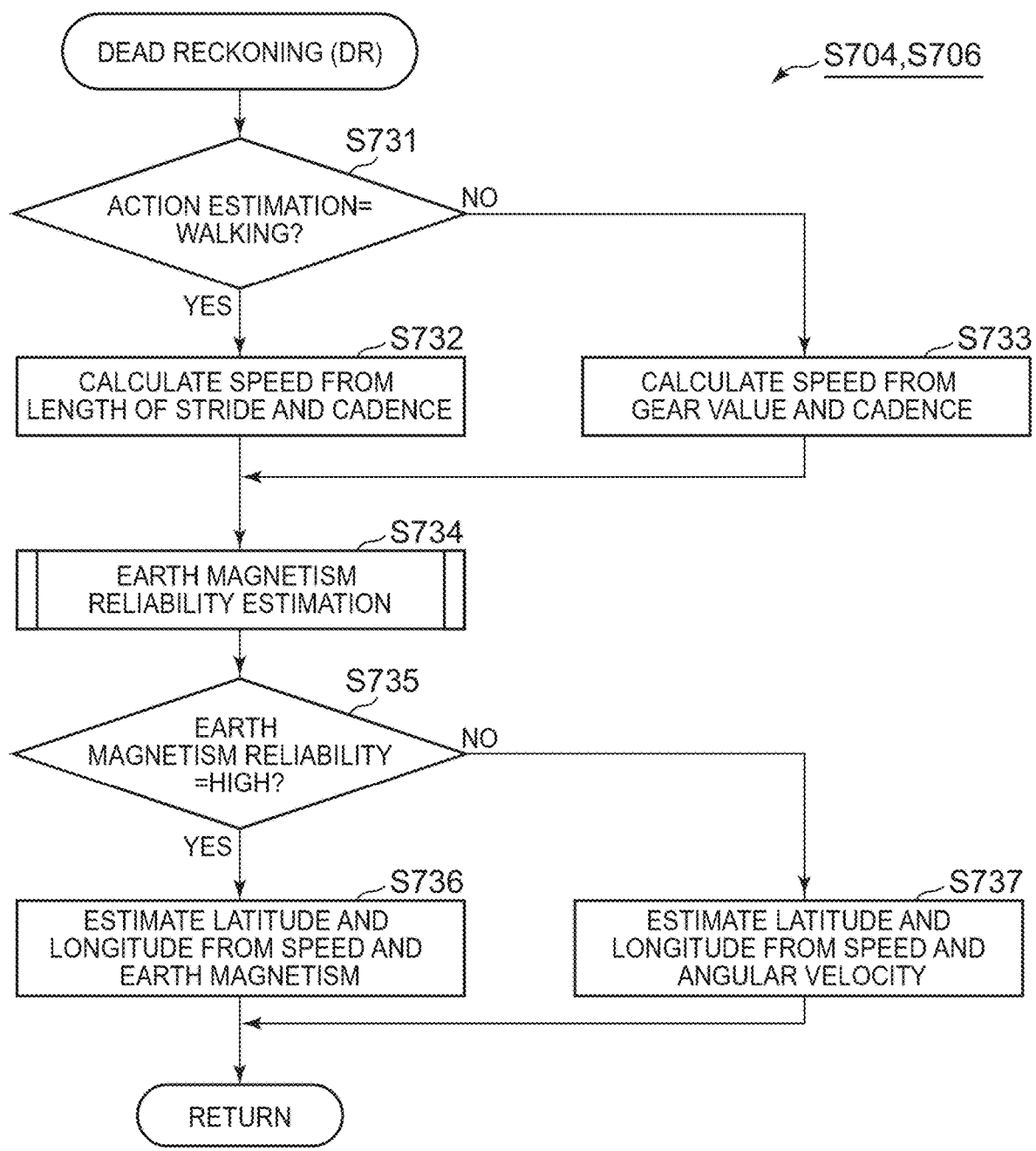
FIG. 23 is a flowchart to show a subroutine of dead reckoning (S704) in FIG. 20 in details according to the embodiment.

FIG. 23 is a flowchart to show a subroutine of the dead reckoning at Step S704 in details.

The CPU 11 firstly determines whether the action estimated at that time is walking or not (Step S731). When the CPU 11 determines that the action estimated is walking (Yes at Step S731), the CPU 11 calculates the speed of walking based on the length of stride and cadence set at that time by the following expression (Step S732):

speed [m/sec.]=length of stride [m/two steps]×(cadence [two steps/min.]/60).

When the CPU 11 determines at Step S731 that the action estimated is not walking (No at Step S731), the CPU 11 calculates the speed of travelling of the bicycle BC based on the gear value and cadence set at that time by the following expression (Step S733):

speed [m/sec.]=gear value [m/rev]×(cadence [rev/min.]/60).

Note here that when cadence is 0 during inertial running. The speed of travelling of the bicycle BC, however, is calculated by the above expression while letting that the cadence immediately before that is not 0 is kept.

After calculating the current speed in this way, the CPU 11 executes estimation of reliability of earth magnetism (Step S734).

When earth magnetism is reliable, the azimuth angle in the travelling direction can be detected directly. The reliability of earth magnetism is therefore estimated so as to remove the influences of accumulation of errors in angular velocity of the output of the gyroscope sensor 22 as much as possible also during the dead reckoning for a long time, and to enable estimation of a correct travelling direction.

Detection of bearing based on earth magnetism, however, may fail in some cases due to the influences from the disturbance. Particularly during cycling on a roadway, the travelling is easily affected from the disturbance because a car as a magnetic body passes close to the bicycle BC. Therefore it is important to estimate the reliability of earth magnetism.

Figure 24:
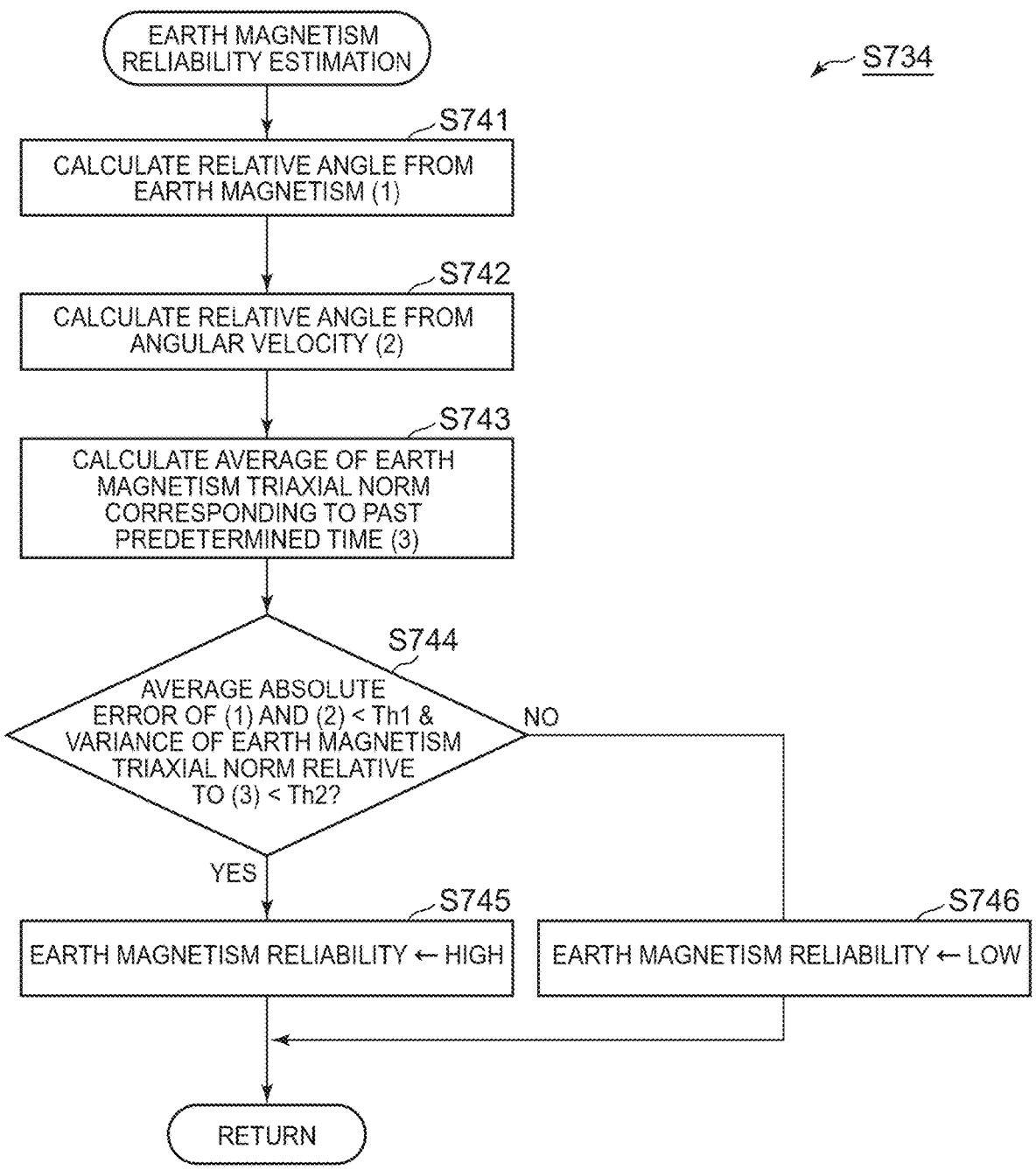
FIG. 24 is a flowchart to show a subroutine of reliability estimation of earth magnetism (S734) in FIG. 23 in details according to the embodiment.

FIG. 24 is a flowchart to show a subroutine of such estimation of the reliability of earth magnetism in details.

Firstly the CPU 11 calculates a relative angle (1) relative to the angle during the immediately preceding detection based on the output of the geomagnetic sensor 23 (Step S741).

Next the CPU 11 calculates a relative angle (2) relative to the angle during the immediately preceding detection based on the output of the gyroscope sensor 22 (Step S742).

The CPU 11 then calculates the average (3) of triaxial norm of the geomagnetic sensor 23 corresponding to the immediately preceding predetermined time, e.g., corresponding to one minute (Step S743).

The CPU 11 determines whether influences from disturbance are small and the earth magnetism is reliable or not (Step S744). This determination is made based on the condition that the absolute error of the average of the relative angle (1) obtained from the geomagnetic sensor 23 and of the relative angle (2) obtained from the gyroscope sensor 22 is smaller than a first threshold Th1, e.g., 5[°] (conditional expression 1) and the condition that variance of triaxial norm of the geomagnetic sensor 23 relative to the average (3) obtained from the triaxial norm of the geomagnetic sensor 23 is smaller than a second threshold Th2, e.g., 10 (when the unit of earth magnetism is [pT]) (conditional expression 2).

When the CPU 11 determines that both of these two conditions are satisfied and so influences from disturbance are small and the earth magnetism is reliable (Yes at Step S744), the CPU 11 sets the reliability of earth magnetism high (Step S745). Then the CPU 11 ends the processing of FIG. 24 and returns to the processing of FIG. 23 as stated above.

When the CPU 11 determines at Step S744 that at least one of these two conditions is not satisfied and so influences from disturbance are large and the earth magnetism is not reliable (No at Step S744), the CPU 11 sets the reliability of earth magnetism low (Step S746). Then the CPU 11 ends the processing of FIG. 24 and returns to the processing of FIG. 23 as stated above.

Figure 25A:
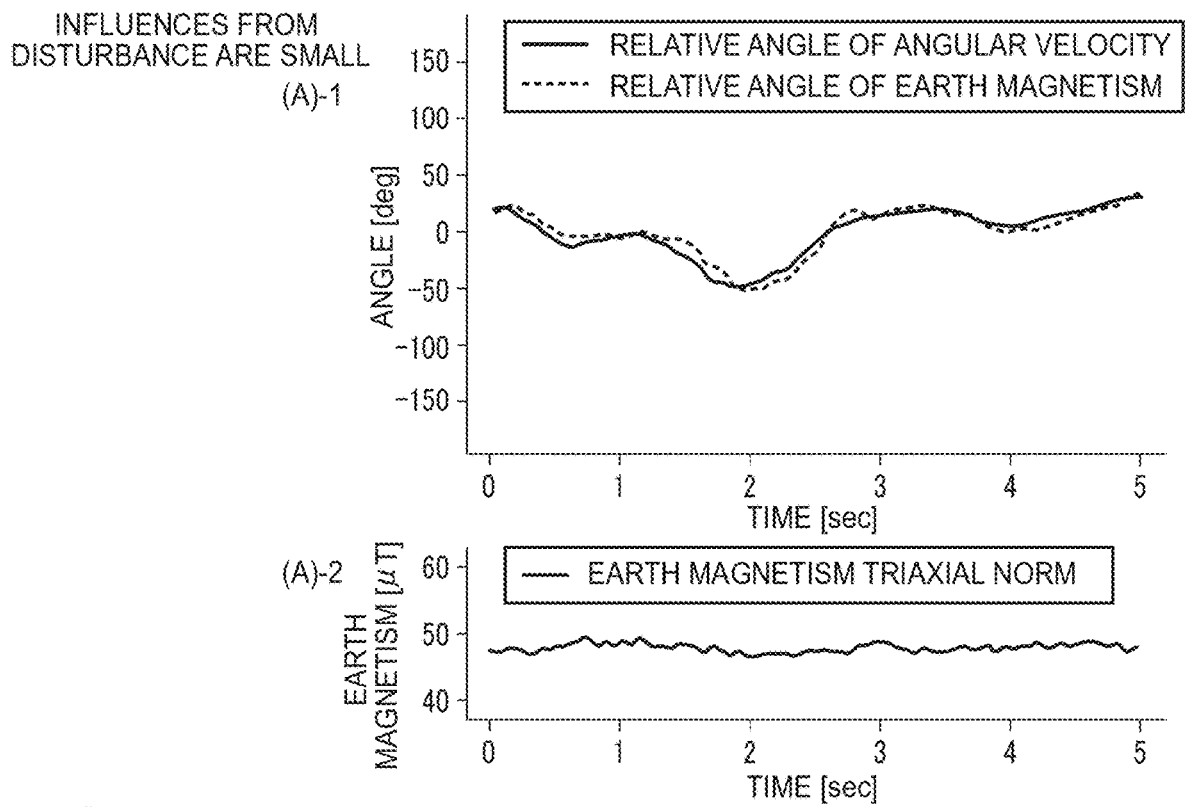
FIGS. 25A and 25B explain the influences from the disturbance on the earth magnetism according to the embodiment.
Figure 25B:
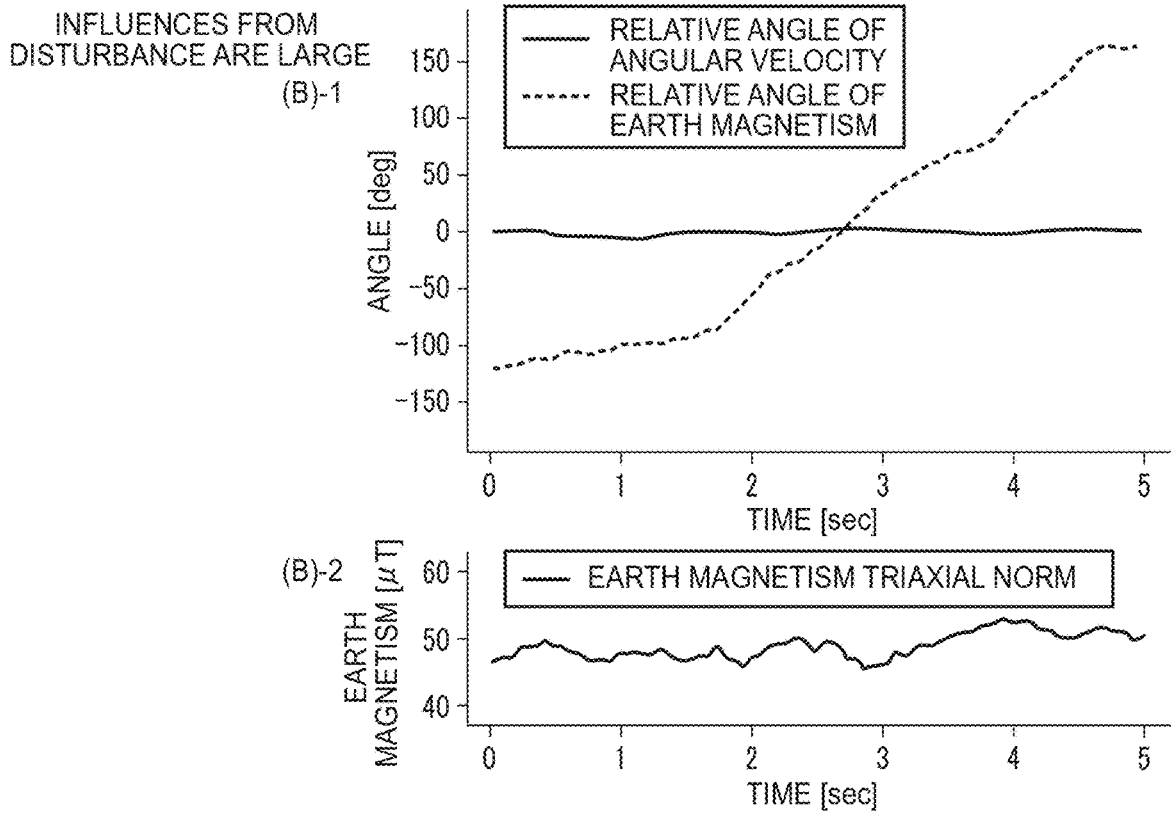

FIGS. 25A and 25B explain the influences from the disturbance on the earth magnetism. FIG. 25A shows the case of small influences from the disturbance. In this case, as shown in FIG. 25A, (A)-1, the relative angle of angular velocity and the relative angle of earth magnetism in the conditional expression (1) are substantially equal, and this means that their average absolute error has a very small value. As shown in FIG. 25A, (A)-2, the left side in the conditional expression 2 and the variance from the average of the triaxial norm of the earth magnetism also are small.

On the contrary, FIG. 25B shows the case of large influences from the disturbance on the earth magnetism. In this case, as shown in FIG. 25B, (B)-1, a difference between the relative angle of angular velocity and the relative angle of earth magnetism in the conditional expression (1) is clearly large. As shown in FIG. 25B, (B)-2, although the left side in the conditional expression 2 and the variance from the average of the triaxial norm of the earth magnetism are larger than the case of FIG. 25A, (A)-1, a very clear difference is not shown.

As in this example, the influences from disturbance cannot be determined only from the conditional expression 2. While the left side of the conditional expression 1 shows a small value, the left side of the conditional expression 2 shows a large value in some cases. Therefore only when both of these two conditional expressions hold, the CPU 11 determines that the earth magnetism is reliable. Thereby the reliability of earth magnetism can be determined more correctly.

After estimating the reliability of earth magnetism in this way, in the processing of FIG. 23, the CPU 11 determines whether the reliability of earth magnetism is set high or not (Step S735).

When the CPU 11 determines that the reliability of earth magnetism is set high (Yes at Step S735), the CPU 11 estimates the longitude and the latitude of the current position (Step S736) based on the speed calculated at Step S732 or Step S733 and the detection result of the earth magnetism by the geomagnetic sensor 23.

When the CPU 11 determines at Step S735 that the reliability of earth magnetism is not high and is set low (No at Step S735), the CPU 11 estimates the longitude and the latitude of the current position (Step S737) based on the speed calculated at Step S732 or Step S733 and the detection result of the angular velocity in the direction of the horizontal plane obtained from the gyroscope sensor 22. That is, when the CPU 11 determines that the reliability of earth magnetism is low, the CPU 11 estimates the longitude and the latitude of the current position based on the detection result of the angular velocity from the gyroscope sensor 22 instead of the detection result of earth magnetism obtained from the geomagnetic sensor 23.

After finishing the dead reckoning of FIG. 23 in this way, the procedure returns to FIG. 20 as stated above. In FIG. 20, when the reliability of GPS is at a medium level, the CPU 11 executes weighting (Step S705) so as to combine the GPS positioning information with the dead reckoning positioning information by the following expression based on a variable r ($0<r<1$) that can be set appropriately in accordance with the reliability of the GPS positioning information:

$$\text{latitude and longitude} = r \times \text{GPS} + (1-r) \times \text{DR},$$

where GPS: longitude and latitude by GPS positioning, DR: longitude and latitude by dead reckoning.

Then the CPU 11 ends the processing of track estimation of FIG. 20.

At the above Step S701, when the CPU 11 determines that the reliability of GPS positioning information is low, the CPU 11 executes dead reckoning (Step S706).

Similarly to the processing at the above Step S704, this dead reckoning is as described above in details while referring to FIG. 23.

After ending the dead reckoning, the CPU 11 updates the longitude and latitude based on the positioning information obtained from dead reckoning only (Step S707) and ends the processing of track estimation of FIG. 20.

As stated above, the present embodiment provides a track estimation device to estimate the track of a series of activity during cycling. For instance, the track estimation device includes: a reliability determination unit configured to determine the reliability of satellite positioning information obtained from a satellite positioning information receiving unit; an update timing determination unit configured to determine the timing of updating a parameter to estimate a travelling speed used for autonomous navigation based on the reliability of satellite positioning information and estimation information on action during the series of activity that is obtained from a cycling recorder; and a track estimation unit configured to, when the reliability determination unit determines that the reliability is low, estimate the track by autonomous navigation. The wearable device 10 has a function as the track estimation device, and the CPU 11 of the wearable device 10 has a function as the reliability determination unit, the update timing determination unit and the track estimation unit.

The present embodiment introduces parameters of cadence and a gear value (a length of stride during walking) to calculate the travelling speed. This means that the speed can be calculated stably simply by obtaining cadence as long as the cyclist CL does not change the gear.

The present embodiment provides the track estimation device to estimate the track of a series of activity during cycling. The track estimation device includes: a reliability determination unit configured to determine the reliability of satellite positioning information obtained from a satellite positioning information receiving unit; an earth magnetism reliability determination unit configured to determine which one of angular velocity and earth magnetism is used to designate the direction based on values calculated from the angular velocity and the earth magnetism; and a track estimation unit configured to, when the reliability determination unit determines that the reliability is low, estimate the track by autonomous navigation. The wearable device 10 has a function as the track estimation device, and the CPU 11 of the wearable device 10 has a function as the reliability determination unit, the earth magnetism reliability determination unit and the track estimation unit.

For the travelling direction, earth magnetism is desirably used because the earth magnetism originally does not have accumulated inaccuracy. In the case of cycling, however, the earth magnetism is often disturbed due to the disturbance when a car approaches the bicycle BC, and therefore the present embodiment estimates the reliability of earth magnetism and then selectively uses the detection by the geomagnetic sensor 23 or the detection by the gyroscope sensor 22.

According to the present embodiment, even when the environment for observation by GPS is bad, the travelling track during cycling, for example, can be calculated precisely.

In the main routine of FIG. 3, after the track estimation at Step S107, the CPU 11 executes speed estimation (Step M108). For the speed, when the GPS positioning information is reliable, the CPU 11 acquires the information on travelling speed with the accuracy of 0.1 [m/sec.] or less based on a Doppler shift value obtained by the GPS positioning.

When the GPS positioning information is not reliable, the CPU 11 calculates the speed based on the distance and time of the track obtained from the track estimation as stated above.

After that, the CPU 11 executes calorie estimation (Step M109).

During the calorie estimation, the present embodiment estimates calorie consumption based on "Table of "METs of physical activities" revised version" published by National Institute of Health and Nutrition in Japan while considering the information analyzed by the wearable device 10. METs (METabolic equivalents) are the units of exercise intensity, where 1 MET represents the exercise intensity during at rest. The intensity of an activity is represented by evaluating how many times the activity consumes energy than during at rest.

Figure 26:
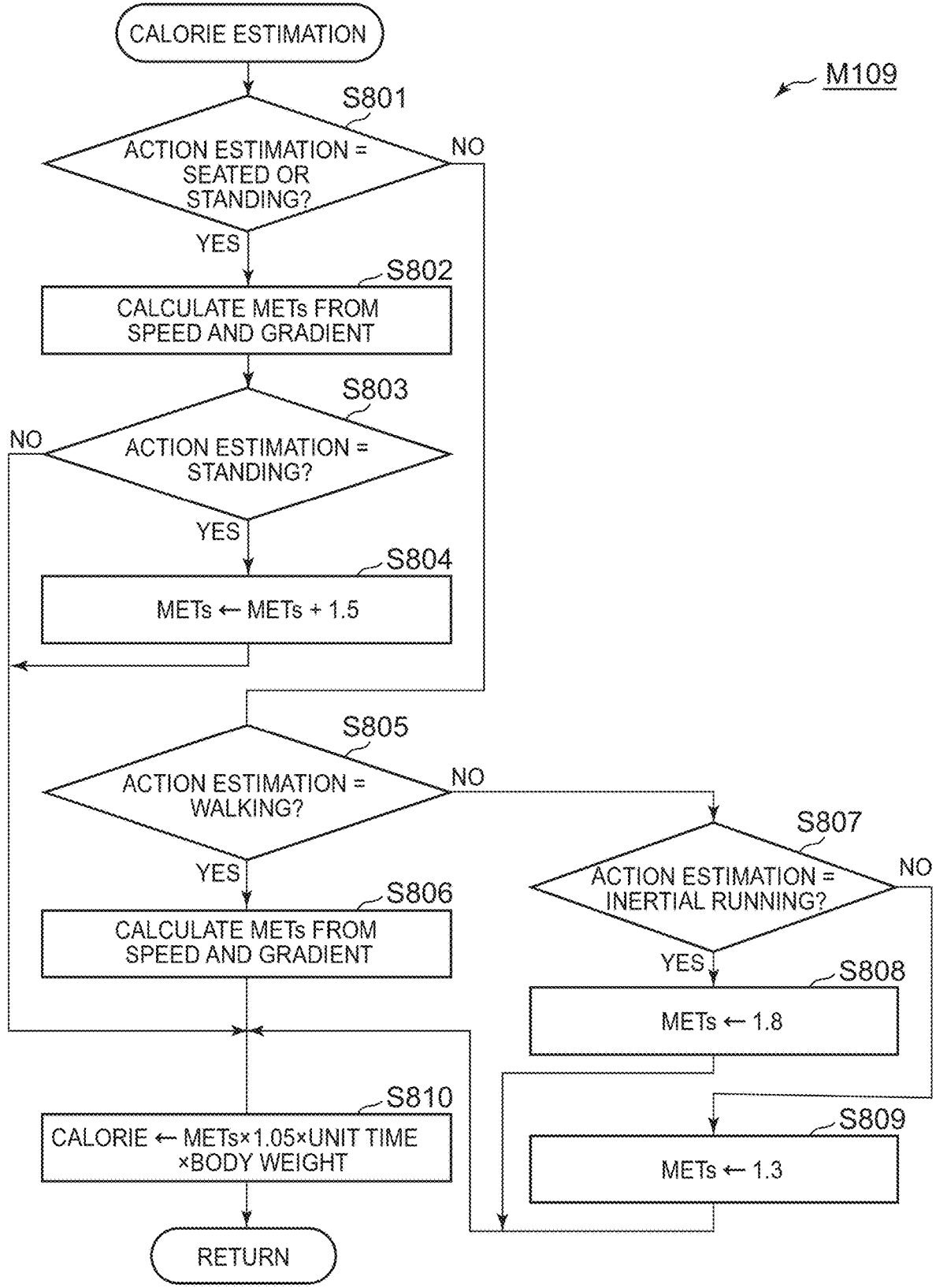
FIG. 26 is a flowchart to show a subroutine of calorie estimation (M109) in FIG. 3 in details according to the embodiment.

FIG. 26 is a flowchart to show a subroutine of the calorie estimation in details. Firstly the CPU 11 determines whether the action estimated is seated or standing (Step S801).

When the CPU 11 determines that the action estimation is seated or standing (Yes at Step S801), the CPU 11 calculates METs from the speed and the gradient (Step S802).

FIG. 27A explains the METS for seated/standing. FIG. 27A, (A)-1 shows the speed METs and FIG. 27A, (A)-2 shows the gradient METs. The CPU 11 finds the sum of these speed METs and gradient METs.

As shown in FIG. 27A, (A)-1, the speed METs has:
a fixed value 1.8 METs at less than the speed of 7.23 [km/h];

$$METs=0.47\times speed[km/h]-1.63 \quad (1)$$

at the speed of 7.23 [km/h] or more and less than the speed of 36.76 [km/h]; and
a fixed value 15.8 METs at the speed of 36.76 [km/h] or more.

As shown in FIG. 27A, (A)-2, the gradient METs for the gradient of 0[%] or more are $$METs=0.55\times gradient[\%] \quad (2).$$

Then the gradient METs are added to the speed METs.

The CPU 11 then determines whether the action estimated is standing or not (Step S803). Only when the CPU 11 determines that the action estimation is standing (Yes at Step S803), the CPU 11 adds a fixed value 1.5 METs to the calculated METs for updating (Step S804).

The above expression (1) is obtained by extracting the items (codes: 01018, 01019, 01020, 01030, 01040, 01050) about the travelling speed of a bicycle from the table of METs, setting the value of METs at their intermediate speeds (see the plotted positions in FIG. 27A, (A)-1), and obtaining a modeled expression by linear regression.

For the speed less than 7.23 [km/h], the METs are a fixed value that is set as a lower limit because the METs during inertial running described later is defined as 1.8 METs.

For the speed of 36.76 [km/h] or more, the METs are set as stated above so as not to exceed the upper limit of 15.8 METs that is defined in the table of METs for the speed of bicycles.

For the gradient METs of expression (2), the METs of an ascending slope during travelling on a bicycle are calculated as 5.5 METS based on the code: 01003 and the code: 01009 in the table of METs, and a modeled expression about an increase of METs due to the gradient is obtained as a model by linear regression while assuming the gradient of the slope as 10[%].

An increased amount during standing described above for Step S804 is obtained by calculating such an increased amount during standing based on the code: 01066 in the table of METs and the calculated value of METs at the speed of 19.3 [km/h] by the above expression (1).

When the CPU 11 determines at Step S801 that the action estimated is neither seated nor standing (No at Step S801), the CPU 11 subsequently determines whether the action estimated is walking or not (Step S805).

When the CPU 11 determines that the action estimation is walking (Yes at Step S805), the CPU 11 calculates METs from the speed METs and the gradient METs (Step S806).

FIG. 27B explains the METS for walking. FIG. 27B, (B)-1 shows the speed METs and FIG. 27B, (B)-2 shows the gradient METs. The CPU 11 finds the sum of these speed METs and gradient METs.

As shown in FIG. 27B, (B)-1, the speed METs has:
for the speed less than 3.2 [km/h], $$METs=0.47\times speed[km/h]+1.3 \qquad (3);$$

for the speed of 3.2 [km/h] or more and the speed less than 8.0 [km/h];

$$METs=0.24\times speed^2-1.5\times speed+5.2 \qquad (4);$$

and for the speed of 8.0 [km/h] or more, a fixed value of 8.4 METs.

As shown in FIG. 27B, (B)-2, the gradient METs for the gradient of 0[%] or more are $$METs=0.42\times gradient[\%] \qquad (5).$$

Then the gradient METs are added to the speed METs.

The CPU 11 then adds a fixed value of 0.8 METs for general walking for updating.

The above expression (3) is obtained by finding a model by linear regression based on the METs at the speed of 0 [km/h] that is 1.3 because the METS during stop described later is defined as 1.3, and the lower limit 3.2 [km/h] of the walking speed defined in the table of METs and the value of METs of 2.8 at this time.

The above expression (4) is obtained by extracting the items (codes: 17152, 17170, 17190, 17200, 17220, 17230, 17231) about the walking speed from the table of METs (see the plotted positions in FIG. 27B, (B)-1), and obtaining a modeled expression by linear regression.

For the speed of 8.0 [km/h] or more, the speed is limited to 8.0 [km/h] that is the upper limit defined as the walking speed, and the METs corresponding to the speed are calculated by the expression (4).

The above expression (5) for gradient METs is obtained by extracting the items (codes: 17210, 17211, 17235) about the speed and gradient during walking from the table of METs, subtracting the METs corresponding to the speed from the expression (4) and obtaining a modeled expression of an increased amount due to the gradient during walking by linear regression.

For the general walking, the fixed value 0.8 METs are added, and this is calculated as an increased amount due to the walking while pushing a bicycle forward because walking as a main target of the present embodiment is likely the walking while pushing the bicycle forward. That is, the items referring to the situation relatively close to the walking while pushing the bicycle forward and the speed are extracted from the table of METs (code: 17100), and the METs corresponding to speed are subtracted from the above expression (4) to calculate such an increased amount due to the walking while pushing a bicycle forward.

When the CPU 11 determines at Step S805 that the action estimated is not walking (No at Step S805), the CPU 11 subsequently determines whether the action estimated is inertial running or not (Step S807).

When the CPU 11 determines that the action estimation is inertial running (Yes at Step S807), the CPU 11 sets the value of METs at a fixed value of 1.8 (Step S808).

More specifically, although inertial running is close to a resting state, the cyclist CL has to keep balance mainly with the upper body against air resistance or vibrations from the road surface during the travelling on a bicycle BC, and so consumes calorie. Based on such assumption, the items relatively close to such a situation (code: 15408) are extracted from the table of METs, and the result is a fixed value of 1.8 METs.

When the CPU 11 determines at Step S807 that the action estimated is not inertial running (No at Step S807), the action estimated results in at rest automatically. Then the CPU 11 set the value of METs as a fixed value of 1.3 (Step S809).

This results from the extraction of the corresponding item (code: 07021) from the table of METs.

The values of METs are calculated for the action estimated that is seated or standing, walking, inertial running, or at rest as stated above. After that, the CPU 11 calculates the calorie consumption by the following expression (Step S810):

$$calorie=METs\ value\times 1.05\times unit\ time[sec.]\times body\ weight[kg].$$

Then the CPU 11 ends the calorie estimation of FIG. 26.

In the main routine of FIG. 3, the CPU 11 subsequently executes the forward-tilting angle estimation (Step M110). The forward-tilting angle represents the tilt of the wearable device 10 attached to the lower back of the cyclist CL toward the travelling direction relative to the vertical direction as the gravity axis.

This is important to represent the activity with a bicycle especially when the bicycle BC is of a road racing type, because the position of hands holding the drop handle (drop position, bracket position, upright position and the like) changes depending on the geographic features of the section where the cyclist CL is pedaling with the bicycle BC or the type of the sport. Especially when the bicycle BC is a road bike, such a position reflects a section where the cyclist CL is pedaling energetically or a section where they are pedaling in a relaxed way. Therefore the forward-tilting angle is important to understand a series of activity with the bicycle BC.

Figure 28:
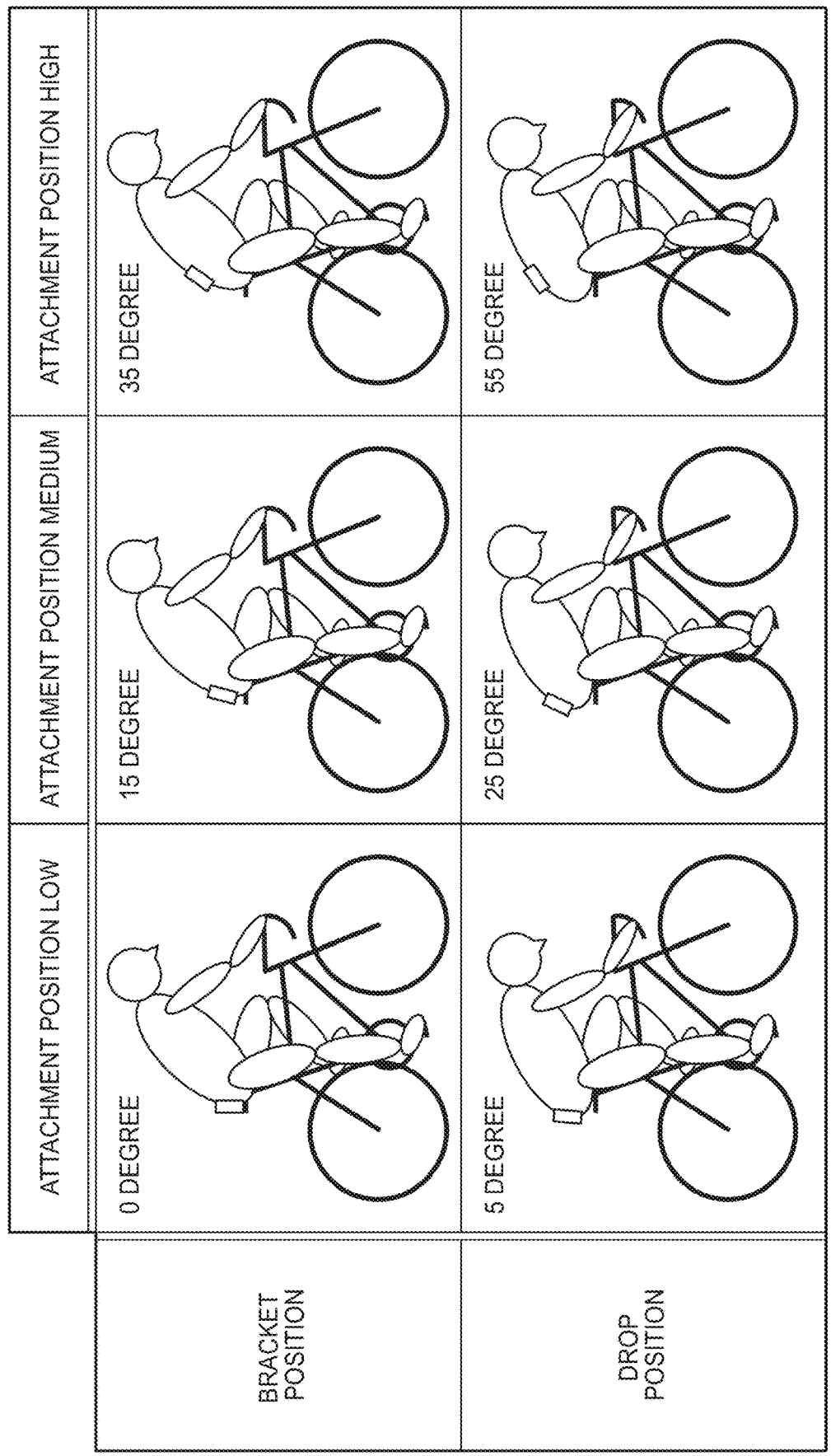
FIG. 28 shows examples of the estimation for forward-tilting angle in association with the positions of the cyclist CL and the height of the attachment position of the wearable device according to the embodiment.

FIG. 28 shows examples of the estimation for forward-tilting angle of the wearable device 10 in association with the bracket position/drop position of the cyclist CL and the height of the position where the wearable device 10 is attached to the cyclist CL (low/medium/high).

The CPU 11 calculates the angle around the x-axis in the gravity direction from the output of the acceleration sensor 21 by Kalman filter processing that is the Infinite impulse response filter to estimate the forward-tilting angle. As shown in FIG. 28, when the attachment position is low, the forward-tilting angle estimated is 0[°] for the bracket position and 5[°] for the drop position, for example. When the attachment position is medium, the forward-tilting angle estimated is 15[°] for the bracket position and 25[°] for the drop position, for example. When the attachment position is high, the forward-tilting angle estimated is 35[°] for the bracket position and 55[°] for the drop position, for example.

After finishing the estimation of the forward-tilting angle, the CPU 11 records the analysis results of the measurement and estimation as stated above collectively in the memory card 17 for storage. When any external device 30 paired with this wearable device 10 is configured, the CPU 11 transmits the analysis results to the external device 30 via the communication interface 14 (Step M111).

The CPU 11 then ends a series of measurement processing to be performed at a constant cycle, e.g., per one [sec.] during activity, and returns to the processing from Step M101 to be ready for the next measurement.

In this way, the CPU 11 repeats the processing between Steps M101 to M111 to execute the measurement by various types of sensors during the activity and store the analysis result sequentially.

After that, when the CPU 11 receives a key operation of the operation unit 16 to instruct start/end of the measurement, and determines at Step M101 that the measurement is not continued (No at Step M101), the CPU 11 subsequently executes clustering of the data stored during the activity (Step M112).

The clustering may be executed by the CPU 11 of the wearable device 10 or by the CPU 31 of the external device 30 that receives the analysis result from the wearable device 10. That is, an activity recording data processor to execute the clustering may be the wearable device 10 or the external device 30, such as a smartphone or a PC.

The clustering is processing to represent any analysis items correctly and present them to the user. For instance, the speed may have a greatly different average or range of the values depending on the physical ability of the user or the purpose of the activity of the user. When the speed is displayed in different colors as in the heat map, if color-coding is performed based on uniform absolute values, a result may be different from the desired one. This is because the colors include substantially one color in spite of the user's intention to give a variety of speeds, for example. To avoid this, clustering is performed so as to correctly represent a relative change in the target item as described later, such as the speed, in the same activity.

The clustering has another object of giving suitable meaning to the analysis result that is difficult for a user to judge the meaning based on the absolute values of the item or the analysis result that the user cannot understand the meaning. The following describes the forward-tilting angle and the gear value as examples.

As stated above referring to FIG. 28, the forward-tilting angle easily has different detection results with a change in the position where the wearable device 10 is attached to the cyclist CL or a change in the position of the cyclist CL. When the wearable device 10 is attached to the clothing of the cyclist CL with a clip, the attachment position of the wearable device 10 easily changes due to the type of the clothing that the cyclist CL is wearing at that day. Therefore it is difficult to determine the degree of forward tilting to show the position of the cyclist CL only based on the absolute value of the forward-tilting angle obtained from the wearable device 10. Then the clustering is performed, whereby the degree of forward tilting to show the position in the same activity can be correctly represented.

The gear value in the present embodiment shows the distance of travelling by a bicycle BC during one rotation of the crank pedal. According to a typical sense of users, this corresponds to the index showing the load of a gear. Since this gear value changes with the diameter of tires or the gear ratio of the bicycle BC, it is difficult to determine the gear value only based on the absolute values. Then the clustering is performed, whereby the load of a gear in the same activity can be categorized and shown correctly.

In the present embodiment, prior to the clustering, the user of the wearable device 10 is requested to select any analysis item beforehand as a target of the clustering. The number of clusters and the width of values are unknown, and the size of clusters are relatively imbalanced.

Figure 29:
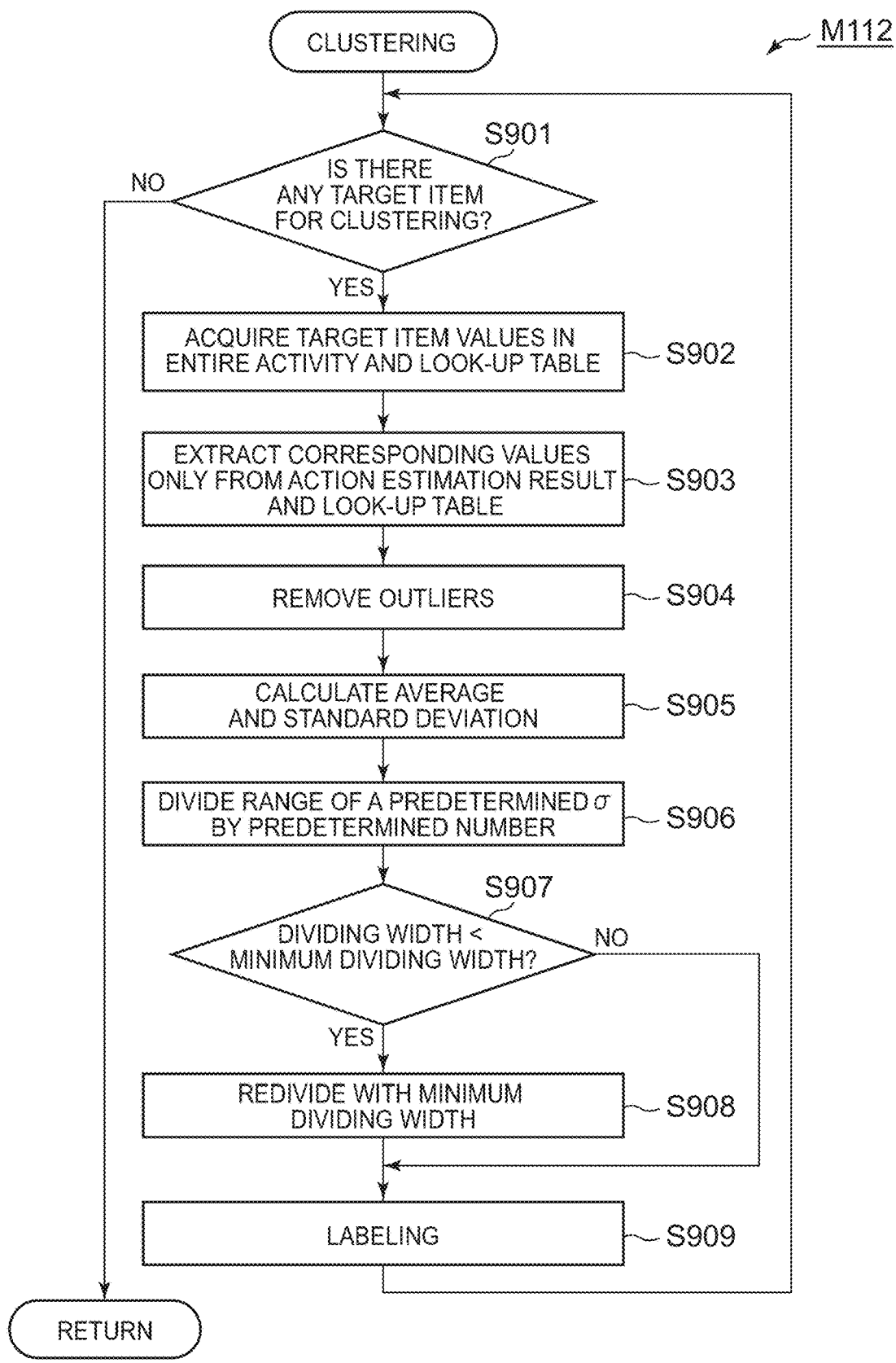
FIG. 29 is a flowchart to show a subroutine of clustering (M112) in FIG. 3 in details according to the embodiment.

FIG. 29 is a flowchart to show a subroutine of the clustering executed by the CPU 11 in details. Firstly the CPU 11 determines whether there is any target item set for the clustering or not (Step S901).

When the CPU 11 determines that there is a target item (Yes at Step S901), the CPU 11 reads out the data of the target item in the entire activity from the memory card 17 and reads out and acquires the corresponding look-up table from the program memory 13 (Step S902).

FIG. 30 shows an example of the look-up table stored in the program memory 13. In this example, the table defines the category of actions about two activities including "cycling" and "trekking". Additionally each activity has suitable items defined, and for each item, the target actions and the basic unit as the minimum dividing width are defined. The minimum dividing width may be appropriately set for the physical ability of the cyclist or the trekker or for the purpose of the activity of them.

The cycling has five categories of action, including seated, standing, inertial running, walking and stop as stated above. The cycling has eight items as the target of clustering, including speed, forward-tilting angle, gear value, cadence, altitude, temperature, gradient and lateral-tilting angle. The speed, forward-tilting angle, gear value, cadence, altitude, temperature and gradient are as mentioned in the above. The lateral-tilting angle is an angle of the tilt of the cyclist's CL body relative to the vertical direction. This is a value obtained from the ratio of the centrifugal force to the gravity, and the centrifugal force is calculated from the angular velocity calculated from the output GyrZ of the gyroscope sensor 22 in the z-axis direction (excluding the body motion) and the speed. Each item has the target actions and the minimum dividing width. For instance, for the item of speed, the target actions include seated, standing and inertial running, and the minimum dividing width is 2 [km/h], for example.

In addition to the cycling, the wearable device 10 can be used for activity recording during other activities, such as trekking. The trekking has four categories of action, including walking, running, vehicles, and stop. That is, walking: the trekker travels at a speed of a predetermined travelling speed or more, running: the trekker travels at a speed of a predetermined travelling or more that is larger than the speed during walking, vehicles: the trekker rides on vehicles, such as a train, a car, and ropeway for travelling, and stop: actions other than the above. This is mainly assumed as a stopping state.

These four actions are obtained as a result of the action estimation performed for a series of trekking activity record that is analogous to the present embodiment.

The clustering for the trekking has four items as the target of clustering, including speed, altitude, temperature, and slope angle. Each item has the target actions and the minimum dividing width. For instance, for the item of speed, the target actions include walking and running, and the minimum dividing width is 0.5 [km/h], for example.

Next the CPU 11 extracts, based on the acquired look-up table and the target items at that time, only the data at corresponding time value from the result of action estimation (Step S903).

For instance, when the target item is the forward-tilting angle, the target actions are seated, standing and inertial running based on the acquired look-up table. That is, when the result of action estimation is walking or stop, the data on forward-tilting angle at that time is not important for the activity with a bicycle and is a noise component. Therefore such data is removed by this extraction processing. In this way, the result of action estimation is used so as to remove noise.

Next the CPU 11 removes a value extremely deviating from the extracted data as the noise component (Step S904).

After that the CPU 11 calculates the average and the standard deviation based on the normal distribution of the remaining data (Step S905). Based on the calculated average and standard deviation, the CPU 11 divides a range of a predetermined σ by a predetermined number (Step S906).

The predetermined σ is decided based on the degree of dispersion in the data distribution that the user wants to focus on. For instance, the target may be the range within ±3σ from the average.

The predetermine number for division is set beforehand depending on the maximum dividing number to be defined or the desired resolution of the divided width. For instance, when this is set as a division into thirds, then the range of a predetermined σ is divided into thirds. Therefore the result includes five divided parts additionally including the parts other than the predetermined σ, i.e., the predetermined σ or more and the predetermined σ or less. In this way, the maximum number of clusters is specified.

The CPU 11 determines whether the dividing width specified by the division is small or not than the minimum dividing width defined in the look-up table (Step S907).

Only when the CPU 11 determines that the dividing width specified by the division is smaller than the minimum dividing width (Yes at Step S907), the CPU 11 performs redivision with the defined minimum dividing width (Step S908).

For the target item that is the forward-tilting angle, for example, when the cyclist CL keeps the same position during the same activity, meaning that the angle hardly changes, this case is desirably output as one cluster. The minimum dividing width, e.g., 2[°] for the forward-tilting angle, for example, is defined beforehand so as to avoid excessive division, and the redivision with the minimum dividing width is performed for such a purpose.

When the CPU 11 determines at Step S907 that the dividing width specified by the division is the minimum dividing width or more (No at Step S907), the CPU 11 does not perform redivision at Step S908.

Finally the CPU 11 performs labeling for each divided region (Step S909). At this step, the CPU 11 may perform corresponding labeling depending on the purpose also for a region of the action estimation result that is not extracted at Step S903 or for an outlier removed at Step S904. This considers the case where, when the target item is speed, for example, the user wants to remove the speed during walking from the calculation of clustering, but wants to include such speed in the color-coding for final categorization because of the continuity of the display, for example. In this way, the CPU 11 can perform continuous labeling for the entire speed during the same activity, including the speed during walking that is excluded from the calculation of clustering.

In this way, the CPU 11 performs a series of clustering processing of one target item until labeling. Then the CPU 11 returns to Step S901 to execute similar processing for each of the target items.

After executing the clustering processing for all of the target items, when the CPU 11 determines at Step S901 that there is not target item to be processed (No at Step S901), the CPU 11 ends the clustering processing in FIG. 29.

After ending the clustering processing, data on the processed target items are presented to the user, such as a cyclist. For example, when the CPU 11 of the wearable device 10 executes the clustering processing (See FIG. 2A), color-coded data on the processed target items may be displayed on a not-illustrated display of the wearable device 10 via the bus B, or such data may be transmitted to an external device from the bus B via the communication interface 14 and the antenna 19, and may be displayed on a display of the external device. Alternatively when the CPU 31 of the external device 30 executes the clustering processing (See FIG. 2B), for example, color-coded data on the processed target items may be displayed on the display 34 of the external device 30 via the bus B1. When the target item is speed, for example, the color-coded speed data is overlapped with the series of track of the activity that is measured and analyzed on the display.

The processing from Steps S905 to S908 may be changed for each of the action (action estimation result) in the target item of clustering processing. For instance, when the target item is cadence, the look-up table of FIG. 30 shows that the target actions of clustering are seated, standing and walking. Then cadence may be greatly different between the seated or standing and the walking. Then, these actions may be processed with different minimum dividing widths for the number of clusters corresponding to the actions, whereby clustering can be performed more suitably.

As stated above, the present embodiment can provide an activity recording data processor having an operation unit configured to extract target activity data as a target from a series of activity based on estimation information on the actions in the series of activity obtained from an activity data analyzer configured to acquire a plurality of types of activity data obtained during the series of activity, and perform clustering of the target activity data. The CPU 11 of the wearable device 10 or the CPU 31 of the external device 30 may have a function as the operation unit in this activity recording data processor.

In the clustering processing of the present embodiment, even when the number of clusters in each item is unknown or the clusters are greatly different in size, the CPU 11 can perform suitable clustering processing for each item based on the basic method, such as using average or standard deviation.

Particularly such clustering processing is not limited to recording of activity during outdoor sports, such as cycling, trekking, running, paddling, and surfing, and is effective to present a series of data having the unknown number of clusters or having different sizes of clusters while emphasizing a relative change of the data correctly or to present data in an understandable manner when the meaning of the data in the form of a simple absolute values is difficult to understand.

The present embodiment enables clustering processing for each of a plurality of items (speed, forward-tilting angle, gear value and the like) independently included in a series of activity record. This allows the user to have appropriate presentation on various items that the wearable device 10 can acquire.

Following the clustering processing, the CPU 11 executes power estimation in the main routine of FIG. 3 (Step M113).

Figure 31:
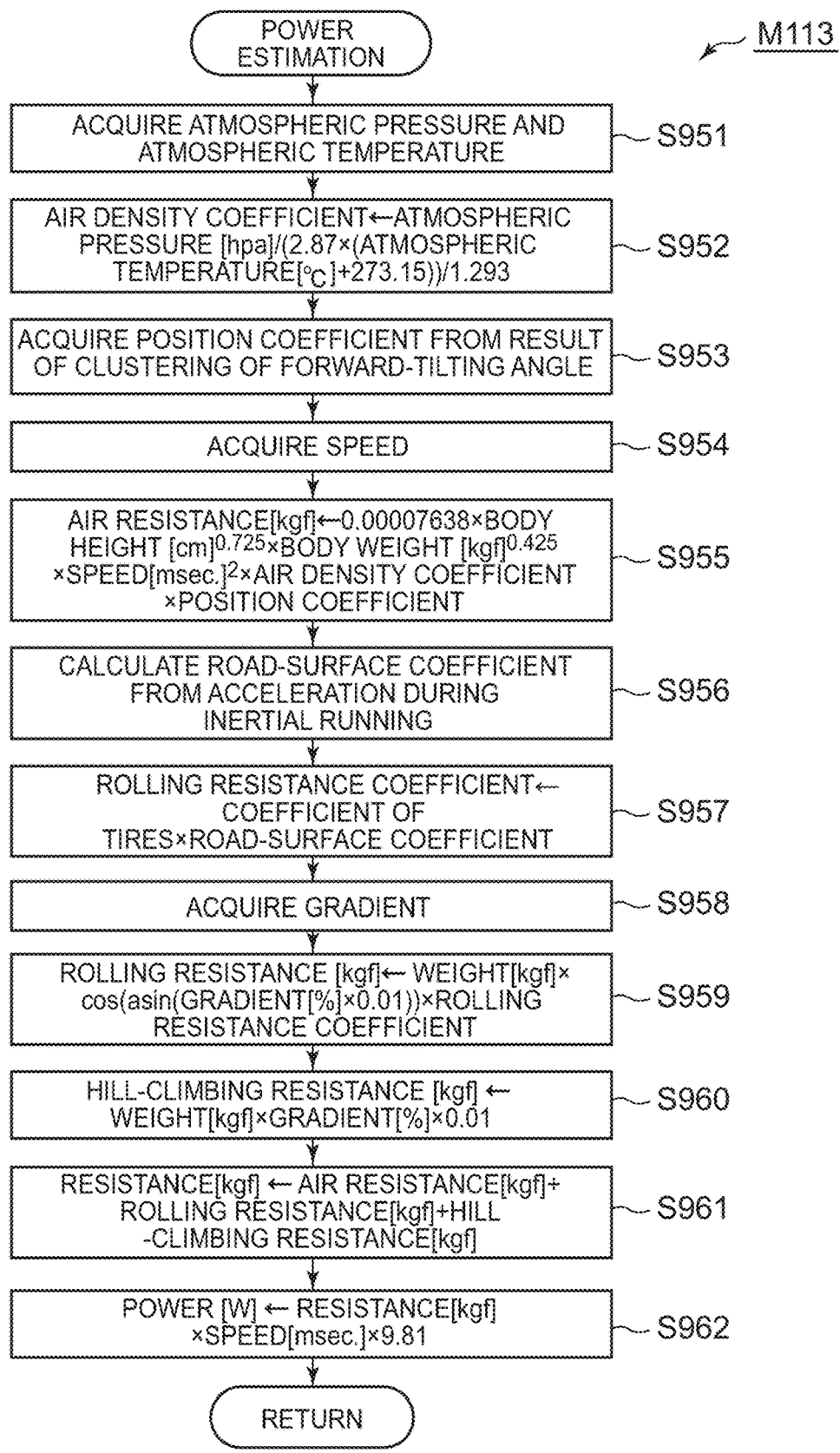
FIG. 31 is a flowchart to show a subroutine of power estimation (M113) in FIG. 3 in details according to the embodiment.

FIG. 31 is a flowchart to show a subroutine of the power estimation in details. The CPU 11 performs the following power estimation for data at each time during activity.

Firstly the CPU 11 acquires data on atmospheric pressure and atmospheric temperature at that time (Step S951).

Next, the CPU 11 calculates the air density coefficient by the following expression (Step S952):

air density coefficient=atmospheric pressure [hPa]/
(2.87×(atmospheric temperature[° C.]+273.15))/
1.293.

Then the CPU 11 acquires the position coefficient from the result of clustering at Step M112 of the forward-tilting angle as stated above (Step S953). Note here that the position coefficient may be drop position: position coefficient=1.0,
bracket position: position coefficient=1.25,
upright position: position coefficient=1.375, and
standing: position coefficient=1.725.

For the drop position, the bracket position, and the upright position, they may be determined from the result obtained by dividing the action estimation corresponding to seated that is obtained by the clustering as stated above into three clusters. For the standing, this may be determined from the result of action estimation.

Next the CPU 11 acquires data on speed (Step S954).

Based on the obtained result, the CPU 11 calculates air resistance by the following expression (Step S955):

air resistance[kgf]=0.00007638×body height [cm]$^{0.725}$×body weight [kgf]$^{0.425}$×speed[m/sec.]$^2$×air density coefficient×position coefficient.

Note here that, in addition to the data acquired and analyzed by the wearable device 10, other data, such as the body height and the body weight of the cyclist CL as the user of the wearable device 10 and the total weight of the body weight, the weight of the bicycle BC and a not-illustrated luggage, is set beforehand in the wearable device 10.

Next the CPU 11 calculates the road-surface coefficient at that time from the variance of acceleration triaxial norm that is obtained by removing the gravity acceleration component from the acceleration obtained at the section during the immediately preceding inertial running (Step S956).

As described above referring to FIGS. 22A and 22B, the acceleration during inertial running differs with the road-surface state. The road-surface coefficient is obtained by setting the state of a smoothly paved road at 1.0 and setting the state of an unpaved road at about 5.0, and by normalizing the values so that the coefficient varies between these values in accordance with the value of the acceleration triaxial norm.

The CPU 11 calculates the rolling resistance coefficient using the obtained road-surface coefficient by the following expression (Step S957):

rolling resistance coefficient=coefficient of tires×
road-surface coefficient.

The coefficient of tires is about 0.004 for a typical road racing type, and is about 0.008 for a typical mountain bike. In this way, the coefficient of tires may be specified within the range about 0.003 to 0.010 for the tires used, and a known value is used in this example.

Next the CPU 11 acquires data on gradient at that time (Step S958).

The CPU 11 calculates the rolling resistance using the obtained data on gradient by the following expression (Step S959):

rolling resistance [kgf]=weight[kgf]×cos(asin(gradient[%]×0.01))×rolling resistance coefficient.

The CPU 11 further calculates the hill-climbing resistance by the following expression (Step S960):

hill-climbing resistance [kgf]=weight[kgf]×gradient
[%]×0.01.

Based on the calculated air resistance, rolling resistance and hill-climbing resistance, the CPU 11 calculates the overall resistance by the following expression (Step S961):

resistance[kgf]=air resistance[kgf]+rolling resistance [kgf]+hill-climbing resistance[kgf]. Finally the CPU 11 calculates the power at that time by the following expression (Step S962):

power [W]=resistance[kgf]×speed[m/sec.]×9.81.

The CPU 11 can repeat the processing of a series of power estimation as stated above at the recording time during the activity so as to calculate the total output value [kWh] of the power used during the activity as a whole.

In the main routine of FIG. 3, the CPU 11 ends a series of the operation with the power estimation at Step M113.

Note here that the operations of the clustering and the power estimation at Step M112 or later in FIG. 3 may not be executed in the wearable device 10, but the external device 30, such as a smartphone or a personal computer, that receives the data from the wearable device 10 for storage may execute these operations in accordance with a preinstalled application program.

As stated above in details, the present embodiment can analyze the activity state during cycling without the need of a plurality of sensors attached to various parts of a bicycle.

In the above embodiments, the wearable device 10 includes the GPS antenna 20 and the GPS receiver 15 so as to calculate absolute values of latitude/longitude/altitude in the three-dimensional space as needed, and these values are used for determination and analysis of the activity state together with information on the reliability of the values. With this configuration, the activity state can be determined more precisely and objectively under the environment where radio waves coming from a positioning satellite are available.

In the present embodiment, the wearable device 10 alone that the cyclist CL is wearing on the body can determine the activity state as one of seated, standing, inertial running, walking and stop, and can record the result with information on the details. With this configuration, the detailed information can be recorded with a more simple operation than a typical cycle computer.

Especially for standing (pedaling while standing up) and walking after dismounting from the bicycle during cycling, their states can be determined more correctly based on the periodicity in vertical motion of the body.

Additionally for the seated (pedaling while sitting on the saddle) during cycling as well, the state can be determined correctly based on the change rate over time in the angular velocity output from the gyroscope sensor and in the acceleration output from the acceleration sensor.

For the determination of the seated, the data is determined at a plurality of levels in accordance with the reliability of the angular velocity output from the gyroscope sensor and the acceleration output from the acceleration sensor, and then based on a result of the determination, the data is determined whether it can be used or not for calculation of cadence executed later. In this way, data can be used as a more reliable result of the determination.

Additionally, in the above embodiments, a value of cadence also is calculated for seated, standing and walking during cycling. Thereby the state during cycling can be determined more specifically.

To calculate the cadence, a precise value can be calculated based on a change over time of the acceleration sensor and the gyroscope sensor.

In the above embodiments, a determination is made while considering the speed and the gradient together during the activity. Thereby the state during various types of activity can be analyzed in details for recording.

Additionally in the present embodiment, calorie consumption is calculated by estimation based on the determination result of the activity state, and the calculated estimation value of the calorie consumption is recorded together with the result of activity determination. Thereby, the user can get the calorie consumption at each time during the activity and the calorie consumption through the entire activity, and therefore can tell a suitable timing for nutritional support, for example.

Similarly in the present embodiment, output power is calculated by estimation based on the determination result of the activity state, and the calculated estimation value of the output power is recorded together with the result of activity determination. Thereby, the user can get the output power at each time during the activity and the output power through the entire activity, and therefore can tell suitable pacing during the activity, for example.

The above embodiments describe the case of determining the activity state during cycling. The present invention does not limit the activity to cycling. For outdoor sports other than cycling, such as trekking, trail running, canoeing, and surfing and various types of ball sports, which may be outdoors or indoors, the present invention can determine the activity state by setting a suitable threshold for the detection output from the sensors.

The present invention is not limited to the above embodiments, and may be modified variously for implementation without departing from the scope of the invention. The embodiments may be combined for implementation as needed, and the combined effect can be obtained in this case. The embodiments include various aspects of the invention, and various aspects of the invention can be extracted by selecting and combining a plurality of constituent elements in the disclosure. For example, some elements may be deleted from the constituent elements disclosed in the embodiments. Such a configuration after deletion also can be extracted as the invention as long as the configuration can solve the problems and have the advantageous effects as mentioned above.

What is claimed is:

1. An activity recording data processing apparatus comprising:
    a processor; and
    a storage unit configured to store a program that the processor executes,
    wherein the processor implements processing including the following processing in accordance with the program stored in the storage unit:
    acquisition processing of acquiring data obtained for a series of activity and action estimation information on the series of activity, the action estimation information being associated with the data;
    extraction processing of extracting partial data of the data based on the action estimation information; and
    clustering processing of performing clustering of the partial data by calculating average and standard deviation of the partial data, dividing the partial data by a predetermined number and performing labeling of the divided partial data.

2. The activity recording data processing apparatus according to claim 1, wherein:
    the data is associated with information on a minimum dividing width, and
    the clustering sets a dividing width to divide by the predetermined number, and the dividing width is the minimum dividing width or more.

3. The activity recording data processing apparatus according to claim 1, wherein the series of activity is cycling, and the data comprises at least one of speed, forward-tilting angle, a gear value, cadence, altitude, temperature, gradient, and lateral-tilting angle.

4. The activity recording data processing apparatus according to claim 3, wherein the action estimation information on the series of activity associated with the data comprises at least one of seated, standing, inertial running, walking and stop.

5. The activity recording data processing apparatus according to claim 1, wherein the series of activity is trekking, and the data comprises at least one of speed, altitude, temperature and slope angle.

6. The activity recording data processing apparatus according to claim 5, wherein the action estimation information on the series of activity associated with the data comprises at least one of walking, running, vehicles, and stop.

7. A method for processing activity recording data implemented with an activity recording data processing apparatus, the method comprising:
    acquiring data obtained for a series of activity and action estimation information on the series of activity, the action estimation information being associated with the data;
    extracting partial data of the data based on the action estimation information; and
    performing clustering of the partial data by calculating average and standard deviation of the partial data, dividing the partial data by a predetermined number and performing labeling of the divided partial data.

8. The method for processing activity recording data according to claim 7, wherein:
    the data is associated with information on a minimum dividing width, and
    the clustering sets a dividing width to divide by the predetermined number, and the dividing width is the minimum dividing width or more.

9. The method for processing activity recording data according to claim 7, wherein the series of activity is cycling, and the data comprises at least one of speed, forward-tilting angle, a gear value, cadence, altitude, temperature, gradient, and lateral-tilting angle.

10. The method for processing activity recording data according to claim 9, wherein the action estimation information on the series of activity associated with the data comprises at least one of seated, standing, inertial running, walking and stop.

11. The method for processing activity recording data according to claim 7, wherein the series of activity is trekking, and the data comprises at least one of speed, altitude, temperature and slope angle.

12. The method for processing activity recording data according to claim 11, wherein the action estimation information on the series of activity associated with the data comprises at least one of walking, running, vehicles, and stop.

13. A non-transitory computer readable recording medium having stored thereon a program that makes a computer of an activity recording data processing apparatus function as:
   an acquisition unit configured to acquire data obtained for a series of activity and action estimation information on the series of activity, the action estimation information being associated with the data;
   an extraction unit configured to extract partial data of the data based on the action estimation information; and
   a clustering unit configured to perform clustering of the partial data by calculating average and standard deviation of the partial data, dividing the partial data by a predetermined number and performing labeling of the divided partial data.

* * * * *